US008431395B2

(12) United States Patent
Ying et al.

(10) Patent No.: US 8,431,395 B2
(45) Date of Patent: Apr. 30, 2013

(54) PLURIPOTENT CELLS FROM RAT AND OTHER SPECIES

(75) Inventors: Qi-Long Ying, Los Angeles, CA (US); Austin Gerard Smith, Cambridge (GB)

(73) Assignee: The University Court of the University of Edinburgh, Edinburgh (GB)

( * ) Notice: Subject to any disclaimer, the term of this patent is extended or adjusted under 35 U.S.C. 154(b) by 1413 days.

(21) Appl. No.: 11/832,317

(22) Filed: Aug. 1, 2007

(65) Prior Publication Data

US 2008/0066197 A1    Mar. 13, 2008

(30) Foreign Application Priority Data

Aug. 1, 2006  (GB) .................................. 0615327.4
Jan. 10, 2007  (GB) .................................. 0700479.9

(51) Int. Cl.
*C12N 5/071*  (2010.01)
*C12N 5/0735*  (2010.01)

(52) U.S. Cl.
USPC ......................................... 435/353; 435/377

(58) Field of Classification Search ........................ None
See application file for complete search history.

(56) References Cited

U.S. PATENT DOCUMENTS

| 6,214,795 | B1 | 4/2001 | Benjamin et al. |
| 6,271,436 | B1 | 8/2001 | Piedrahita et al. |
| 2002/0045260 | A1 | 4/2002 | Hung et al. |
| 2002/0188963 | A1 | 12/2002 | Loring |
| 2005/0037492 | A1 | 2/2005 | Xu et al. |
| 2006/0083711 | A1 | 4/2006 | Berry et al. |
| 2008/0014638 | A1 | 1/2008 | Smith et al. |

FOREIGN PATENT DOCUMENTS

| EP | 0 695 351 B1 | 12/1999 |
| EP | 1 726 640 A1 | 11/2006 |
| EP | 1726640 | 11/2006 |
| GB | 2 436 737 A | 10/2007 |
| JP | 2002-176973 | 6/2002 |
| WO | WO 95/06716 | 3/1995 |
| WO | WO 98/30679 | 7/1998 |
| WO | WO 99/27076 | 6/1999 |
| WO | WO 00/15764 | 3/2000 |
| WO | WO 03/073843 | 9/2003 |
| WO | WO 03/095628 A2 | 11/2003 |
| WO | WO 2005/039486 A2 | 5/2005 |
| WO | WO 2005/085427 | 9/2005 |
| WO | WO 2005/094830 A1 | 10/2005 |
| WO | WO 2006/026473 | 3/2006 |
| WO | WO 2006/135824 | 12/2006 |
| WO | WO 2007/062243 | 5/2007 |
| WO | WO 2007/136465 A2 | 11/2007 |

OTHER PUBLICATIONS

Ying, Q. et al., "The ground state of embryonic stem cell self-renewal", May 2008, Nature, vol. 453: pp. 519-524.*

Alonso et al., "GSK-3 Inhibitors: Discoveries and Developments", Current Medical Chemistry, 2004, 11:755-763.
English et al., "Pharmacological Inhibitors of MAPK Pathways", Trends in Pharmacological Sciences, 2002, 23:40-45.
Hetman et al., "ERK1/2 Antagonizes Glycogen Synthase Kinase-3β-Induced Apoptosis in Corical Neurons", The Journal of Biological Chemistry, 2002, 277:49577-49584.
Quevedo et al:, "Two Different Signal Transduction Pathways Are Implicated in the Regulation of Initiation Factor 2B Activity in Insulin-Like Growth Factor-1-Stimulated Neuronal Cells", The Journal of Biological Chemistry, 2000, 275:19192-19197.
Wan et al., "Synthesis and Target Identification of Hymenialdisine Analogs", Chemistry and Biology, 2004, 11:247-259.
Wang et al., "Glycogen Synthase Kinase-3 Is a Negative Regulator of Extracellular Signal-Regulate Kinase ", Oncogene, 2006, 25:43-50.
Great Britain Search Report for GB0606392.9, dated Jul. 18, 2006.
Great Britain Search Report for GB0615327.4, dated Nov. 29, 2006.
Great Britain Search Report for GB0706239.1, dated Jul. 30, 2007.
PCT International Search Report for PCT/GB2007/00116, dated Sep. 27, 2007.
Brenin et al., "Rat Embryonic Stem Cells: A Progress Report", Transplantation Proceedings, 29:1761-1765 (1997).
Jiang et al., "Pluripotency of Mesenchymal Stem Cells Derived from Adult Marrow", Nature, 418:41-49 (2002).
Office Action dated Apr. 15, 2010, in co-pending U.S. Appl. No. 11/694,351.
Baharvand et al., *Develop. Growth Differ.* 48:117-128 (2006).
Bennett et al., *J. Biol. Chem.* 277(34):30998-31004 (2002).
Bertrand et al., *J. Mol. Biol.* 333:393-407 (2003).
Bradley et al., *Nature* 309:255-256 (1984).
Brenin et al., *Transplant. Proc.* 29:1761-1765 (1997).
Brons et al., *Nature Letters* p. 1-6 (2007).
Buehr et al., *Biol. Reprod.* 68:222-229 (2003).
Buehr et al., *Phil. Trans. R. Soc. Lond.* B 358:1397-1402 (2003).
Chambers et al., *Cell* 113:643-655 (2003).
Charreau et al., *Transgenic Research* 5:223-234 (1996).
Dattena et al., *Mol Reprod Dev.* 74(1):42-47 (2007).
Davies et al., *Biochem J.* 351:95-105 (2000).
Doetschman et al., *Dev. Biol.* 127(1):224-227 (1988).
Downey et al., *J. Biol. Chem.* 271(35):21005-21011 (1996).
Duesbery et al., *J. Appl. Microbiol.* 87(2):289-293 (1999).
Dvorak et al., *Int. J. Dev. Biol.* 39: 645-652 (1995).
Evans et al., *Nature* 292:154-156 (1981).
Fandrich et al., *Nat Med* 8(2):171-178(2002).
Fowler et al., Practical Statistics for Field Biology, 2$^{nd}$ Ed., John Wiley and Sons, New York; Chapter 13, pp. 111-122 (1998).
Gardner et al., *Int. J. Dev. Biol.* 41:235-243 (1997).
Gordon et al., *Proc. Natl. Acad. Sci. USA*, 77(12):7380-7384 (1980).
Gu et al., *Mol. Cell. Biol.* 25(19):8507-8519 (2005).
Holm et al., *Theriogenology* 52(4):683-700 (1999).
Huang et al., *Cell Biol. Int.* 31:1079-1088 (2007).
Iannaccone et al., *Dev. Biol.* 163:288-292 (1994).
Iannaccone et al., *Dev. Biol.* Correction 185:124-125 (1997).
Kozlova et al., Proceedings of the 5$^{th}$ Annual Meeting of the International Society for Stem Cell Research, Abstract MON-255, p. 130-131 (2007).

(Continued)

*Primary Examiner* — Michael Burkhart

(74) *Attorney, Agent, or Firm* — Finnegan, Henderson, Farabow, Garrett & Dunner, L.L.P.

(57) ABSTRACT

Pluripotent cells are derived and maintained in a self-renewing state in serum-free culture medium comprising a MEK inhibitor, a GSK3 inhibitor and an antagonist of an FGF receptor.

39 Claims, 25 Drawing Sheets

OTHER PUBLICATIONS

Li et al., *Mol. Repr. Dev.* 72:152-160 (2005).
Lonergan et al., *Theriogenology* 51(8):1565-1576 (1999).
Mak et al., *Science* 303:666-669 (2004).
Martin, *Proc. Natl. Acad. Sci. USA* 78(12):7634-7638 (1981).
Matsuda et al., *EMBO J.* 18(15):4261-4269 (1999).
Mitsui et al., *Cell* 113:631-642 (2003).
Nichols et al., *Cell* 95:379-391 (1998).
Nichols et al., *Reprod. Fertil. Dev.* 10:517-525 (1998).
Niwa et al., *Cell* 123:917-929 (2005).
Niwa et al., *Genes Dev.* 12:2048-2060 (1990).
Niwa, *Development* 134:635-646 (2007).
Notarianni et al., *J. Reprod. Fertil. Suppl.* 43:255-260 (1991).
Okamoto et al., *Science* 303:644-649 (2004).
Pashai et al., Proceedings of the 5th Annual Meeting of the International Society for Stem Cell Research, Abstract TUE-248, p. 220 (2007).
Prelle et al., *Cells Tissues Organs* 165:220-236 (1999).
Rastan et al., *J. Embryol. Exp. Morph.* 90:379-388 (1985).
Rathjen et al., *Cell* 62:1105-1114 (1990).
Richings et al., Proceedings of the 5th Annual Meeting of the International Society for Stem Cell Research, Abstract TUE-247, p. 220 (2007).
Ring et al., *Diabetes* 52:588-595 (2003).
Rodriguez et al., *Theriogenology* 67:1092-1095 (2007).
Ruhnke et al., *Stem Cells* 21:428-436 (2003).
Saito et al., *Roux's Arch Dev. Biol.* 201:134-141 (1992).
Sato et al., *Nat. Med.* 10(1):55-63 (2004).
Schaffer et al., *Gene* 302:73-81 (2003).
Schulze et al., *Methods Mol. Biol.* 329:45-58 (2006).
Silva et al., *Dev Cell* 4:481-495 (2003).
Smith et al., *Nature* 336:688-690 (1988).
Smith, *Annu. Rev. Cell Dev. Biol.* 17:435-462 (2001).
Smith, Stem Cell Biology Chapter 10, pp. 205-230 (Cold Spring Harbor Laboratory Press, New York) (2001).
Sukoyan et al., *Mol. Reprod. Dev.* 33(4):418-31 (1992).
Sumner, *Cancer Genet Cytogenet.* 6:59-87 (1982).
Tervit et al., *J. Reprod. Fertil.* 30(3):493-497 (1972).
Tesar et al., *Nature Letters* 448:196-199 (2007).
Vassilieva et al., *Exp. Cell Res.* 258(2):361-373 (2000).
Verma et al., Proceedings of the 5th Annual Meeting of the International Society for Stem Cell Research, Abstract WED-236, p. 309 (2007).
Watanabe et al., *Nature Biotechnology* 25(6):681-686 (2007).
Wiles et al., *Exp. Cell Res.* 247:241-248 (1999).
Yamamura et al., *Dev. Genet.* 2:131-146 (1981).
Ying et al., *Cell* 115:281-292 (2003).
Ying et al., *Methods Enzymol.* 365:327-341 (2003).
Zar, Biostatistical Analysis, IE 4th Ed., Prentice Hall International, Inc., Upper Saddle River, New Jersey; pp. 487-489 (1999).
Zhan et al., *Cell Biochem. Biophys.* 43:379-405 (2005).
Zhang et al., *Bioorg. Med. Chem. Lett.* 10:2825-2828 (2000).
Zwaka et al., *Development* 132:227-233 (2005).
Brook et al., "The Origin and Efficient Derivation of Embryonic Stem Cells in the Mouse", Proc. Natl. Acad. Sci., USA vol. 94, pp. 5709-5712 (1997).
Buehr et al., "Genesis of Embryonic Stem Cells", Phil. Trans. R. Soc. Lon. B vol. 358, pp. 1397-1402 (2003).
Cline et al., "Effects of a Novel Glycogen Synthase Kinase-3 Inhibitor on Insulin-Stimulated Glucose Metabolism in Zucker Diabetic Fatty (fa/fa) Rats", Diabetes, vol. 51, pp. 2903-2910 (2002).
Force et al., "Inhibitors of Protein Kinase Signaling Pathways: Emerging Therapies for Cardiovascular Disease", Circulation, vol. 109, pp. 1196-1205 (2004).
Kobayashi et al., "Lithium Activates Mammalian Na+/H+ Exchangers: Isoform Specificity and Inhibition by Genistein", Eur. J. Physiol., vol. 439, pp. 455-462 (2000).
McWhir et al., "Selective Ablation of Differentiated Cells Permits Isloation of Embryonic Stem Cell Lines From Murine Embryos With Anon-Permissive Genetic Background", Nat. Genetics, vol. 14, pp. 223-226 (1996).
Meijer et al., "GSK-3-Selective Inhibitors Derived From Tyrian Purple Indirubins", Chemistry and Biology, vol. 10, pp. 1255-1266 (2003).
Ryves et al., "Glycogen Synthase Kinase-3 Inhibition by Lithium and Beryllium Suggests the Presence of Two Magnesium Binding Sites", Biochem. Biophys. Res. Commun., vol. 290, pp. 967-972 (2002).
Voigt et al., "Pluripotent Stem Cells and Other Technologies Will Eventually Open the Door for Straightforward Gene Targeting in the Rat", Disease Models & Mechanisms, vol. 2, pp. 341-343 (2009).
Office Action dated Nov. 16, 2009, in co-pending U.S. Appl. No. 11/694,351.
Office Action dated Aug. 5, 2009, in co-pending U.S. Appl. No. 11/694,351.
Office Action dated Oct. 27, 2008, in co-pending U.S. Appl. No. 11/694,351.
Chen et al., Proc. Natl. Acad. Sci USA 103(46):17266-17271 (2006).
Durcova-Hills et al., Stem Cells 24:1441-1449 (2006).
Frame et al., Biochem. J. 359:1-16 (2001).
Gabay et al., Neuron 40:485-499 (2003).
Kunath et al., Development 134:2895-2902 (2007).
Matsui et al., Cell 70:841-847 (1992).
Meijer et al., Trends Pharmacol. Sci. 25(9):471-480 (2004).
Murray et al., Biochem J. 384:477-488 (2004).
Niwa et al., Nat. Genet. 24:372-376 (2000).
Paling et al., J. Biol. Chem. 279(46):48063-48070 (2004).
Resnick et al., Nature 359:550-551 (1992).
Stavridis et al, Development 134:2889-2894 (2007).
Thomson et al., Science 282:1145-1147 (1998).
Vallier et al., J. Cell Sci. 118:4495-4509 (2005).
Wutz et al., Mol. Cell 5:695-705 (2000).
Xu et al., Nat. Methods 2(3):185-190 (2005).
Ying et al., Nat. Biotechnol. 21:183-186 (2003).
Buehr et al., "Capture of Authentic Embryonic Stem Cells from Rat Blastocysts," *Cell*, 135: 1287-1298 (2008).
Cao et al., "In vitro differentiation of rat embryonic stem cells into functional cardiomyocytes," *Cell Research*, 21: 1316-1331 (2011).
Cohen et al., "GSK3 Inhibitors: Development and Therapeutic Potential," Nature Reviews, 3: 479-487 (2004).
Hamanaka et al., "Generation of Germline-Competent Rat Induced Pluripotent Stem Cells," *PLoS ONE*, 6(7)e22008: 1-9 (2011).
Hanna et al., "Human embryonic stem cells with biological and epigenetic characteristics similar to those of mouse ESCs," *PNAS*, 107(20): 9222-9227 (2010).
Hirabayashi et al., "Establishment of Rat Embryonic Stem Cell Lines That Can Participate in Germline Chimerae at High Efficiency," *Mol. Reprod. Dev.*, 77: 94 (2010).
Kawamata et al., "Establishment of Embryonic Stem Cells from Rat Blastocysts," *Rat Genomics: Methods and Protocols*, Methods in Molecular Biology, 597: 169-177 (2010).
Kawamata et al, "Generation of genetically modified rats from embryonic stem cells," *PNAS*, 107 (32): 14223-14228 (2010).
Leitch et al., "Embryonic germ cells from mice and rats exhibit properties consistent with a generic pluripotent ground state," *Development*, 137: 2279-2287 (2010).
Li et al., "Germline Competent Embryonic Stem Cells Derived from Rat Blastocysts," *Cell*, 135: 1299-1310 (2008).
Li et al., "Generation of Rat and Human Induced Pluripotent Stem Cells by Combining Genetic Reprogramming and Chemical Inhibitors," *Cell Stem Cell*, 4:16-19 (2009).
Liskovykh et al., "Derivation, Characterization, and Stable Transfection of Induced Pluripotent Stem Cells from Fischer344 Rats," *PLoS ONE*, 6(11):e27345: 1-9 (2011).
Meek et al., "Efficient Gene Targeting by Homologous Recombination in Rat Embryonic Stem Cells," *PLoS ONE*, 5(12)e14225: 1-6 (2010).
Wang et al., "Rapid and efficient reprogramming of somatic cells to induced pluripotent stem cells by retinoic acid receptor gamma and liver receptor homolog 1," *PNAS*, 108(45): 18283-18288 (2011).
Office Action mailed Nov. 29, 2011, in U.S. App. No. 12/581,981.
*Ex parte Malnoe*, No. 2011-003041 (B.P.A.I. Jul. 11, 2011) (U.S. Appl. No. 10/180,773), Admin. Pat. Judge Walsh.

Takahama et al, "Molecular cloning and functional analysis of cDNA encoding a rat leukemia inhibitory factor: towards generation of pluripotent rat embryonic stem cells," *Oncogene*, 16(24): 3189-3196 (1998).

Amendment and Response under 37 C.F.R. § 1.114 filed Oct. 15, 2010, in U.S. Appl. No. 11/694,351.

Amendment and Reply to Office action filed May 29, 2012, in U.S. Appl. No. 12/581,981.

Final Office Action mailed Jun. 26, 2012, in U.S. Appl. No. 12/581,981.

\* cited by examiner colony of rat ES cells

Expression of Nanog demonstrated
by immunohistochemistry

Expression of Oct4 demonstrated
by immunohistochemistry

Expression of Cdx-2 demonstrated
by immunohistochemistry

Expression of alkaline phosphatase
(histochemical stain)

RT-PCR characterisation of 4 lines of rat ES cells. mESC indicates results from mouse ES cells. (Primers used for Nanog RT-PCR are specific for rat Nanog and do not amplify the mouse sequence).

Rat 3l cell tumour histological sections

| Medium | Time in culture | Mean no. oct4 positive cells in outgrowth | Mean no. cdx2 positive cells in outgrowth |
|---|---|---|---|
| GMEM+serum +LIF | 1 day | 9.25 (n=6) | <1 (n=6) |
| 3i | 1 day | 9.35 (n=14) | <1 (n=14) |
| GMEM+serum +LIF | 3 days | 7.8 (n=26) | 14.0 (n=26) |
| 3i | 3 days | 42.2 (n=23) | <1 (n=23) |

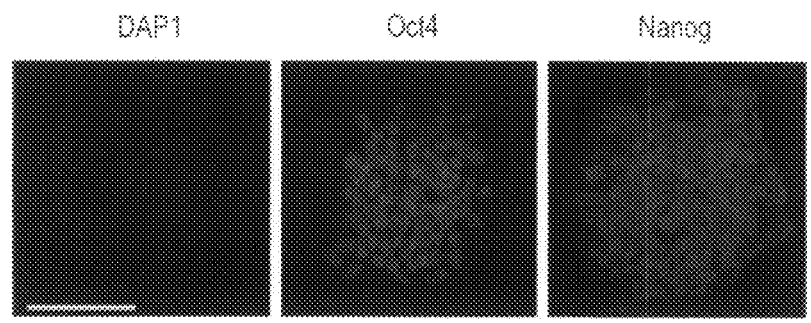
Fig.11c
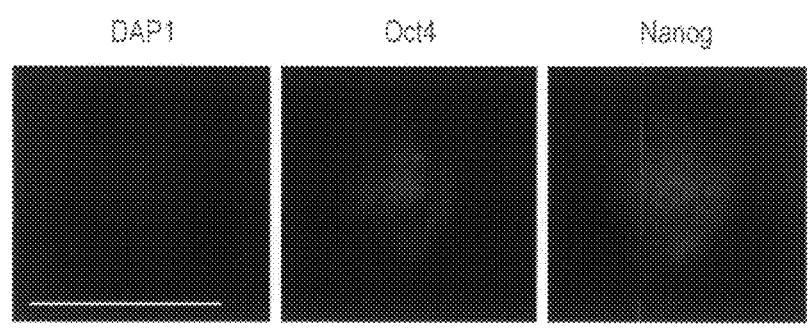
Fig.11d
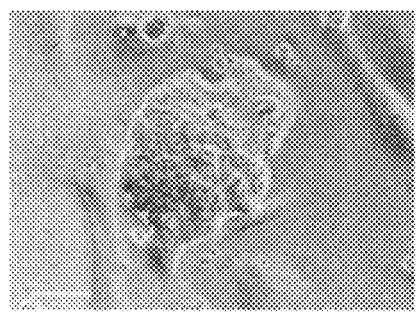 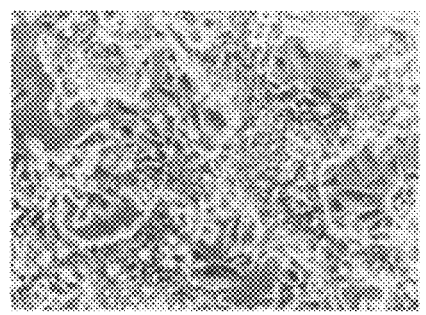
Fig.12a     Fig.12b

PLURIPOTENT CELLS FROM RAT AND OTHER SPECIES

This application claims the benefit under 35 U.S.C. §119 of Great Britain Application No. 0615327.4, filed Aug. 1, 2006, and Great Britain Application No. 0700479.9, filed Jan. 10, 2007, all of which are incorporated herein by reference.

The present invention relates to maintenance of a self renewing phenotype in pluripotent stem cells. The methods and compositions provided are suitable for culturing and isolating pluripotent stem cells such as embryonic stem (ES) cells, especially mammalian, including rat, mouse, bovine, ovine, porcine and human, stem cells. In particular this invention relates to self-renewing cultures of rat, mouse and human pluripotent cells and to methods and compositions therefor.

The establishment and maintenance of in vitro pluripotent stem cell cultures in the presence of medium containing serum and Leukaemia Inhibitory Factor (LIF) is well known (Smith et al. (1988) Nature 336: 688-90). Such methods have been used to maintain pluripotent embryonic stem (ES) cells from "permissive" strains of mice over many passages. Maintenance and self renewal of pluripotent stem cell cultures is further supported where the stem cells are cultured in the presence of feeder cells or extracts thereof, usually mouse fibroblast cells. Under such conditions it is possible to maintain human ES cells in a pluripotent state over many passages in culture.

In many cases ES cells can only be maintained, or are best maintained, using medium that contains serum or serum extract, and hence is undefined, or using cell culture conditions that require the presence of other cells, such as the fibroblast feeder cells used to maintain human ES cells. But any undefined component, whether in the medium or produced by e.g. the feeder cells, potentially interferes with or hinders research into ES cell propagation and differentiation. This prevents development of good manufacturing practices for therapeutic and other applications of ES cells and their progeny. Some defined ES cell media are known but alternative and preferably improved defined media are needed.

In prior applications by the applicants, WO-A-03/095628 and a later as yet unpublished application, culturing pluripotent stem cells, such as ES cells, in serum-free media comprising (1) agonists of gp130 (e.g. LIF) and (2) agonists of the TGF-β superfamily (e.g. BMP4) or Id signalling pathways is used to promote self renewal of the stem cells for multiple passages. In the presence of gp130 signalling, an agonist of the TGF-β superfamily or the Id signalling pathway surprisingly provided a self renewal stimulus rather than a pro-differentiation signal. Nevertheless, ever improved efficiencies in maintaining pluripotent cells in a self renewing state and media for transferring pluripotent cells away from feeder cells or away from feeder-conditioned medium is desired.

Sato N, et al, Nat. Med. Jan. 10, 2004(1) pp 55-63 describe the effects of a Glycogen Synthase Kinase 3 (GSK3) inhibitor, 6-bromoindirubin-3'-oxime, on mouse and human ES cells in serum containing medium. These effects, however, were observed only over a very short time frame, too short for firm conclusions to be drawn, and the influence of unknown factors in the undefined media used in that study may be significant. The inventors of the present invention have tried but failed to repeat the results, and have in fact found effects opposite to those described.

For preparation of ES cell culture media it is desired to provide individual media components in as pure a form as possible. However, most media components are cytokines the purity of which is compromised by the need to manufacture them in cellular systems and then remove potential contaminants from the production broth. Another problem with some cytokines is that they have a narrow range of concentration over which they are effective and non-toxic. Media components which have a broader range and/or are less toxic at higher concentrations would be highly useful. Cytokines can also have limited stability in storage, and more stable media components are sought.

An object of the invention is to overcome or at least ameliorate problems in the art, preferably to provide alternative, more preferably improved, methods of culturing and culture media suitable for pluripotent stem cells, which are capable of supporting self-renewal of said stem cells for many passages. A further object of the invention is to provide an alternative culturing system that permits maintenance of a pluripotent stem cell culture in vitro until differentiation of the cells can be induced in a controlled manner. A still further object of the invention is to provide methods and compositions that enhance the derivation and isolation of pluripotent stem cells and facilitate their derivation and isolation from organisms refractory to ES cell isolation or from which pluripotent stem cells have not yet been isolated. A further, related, object of the invention is to provide pluripotent stem cells from such organisms.

BRIEF DESCRIPTION OF THE DRAWINGS

FIGS. 11A-D show rat ICM outgrowths and primary colonies retain expression of Oct4 and Nanog in 3i. Figure A shows immunofluorescence stainings of ICMs for Oct4 and Cdx2 after 3 days in culture in the presence of serum and LIF, or in 3i. Figure aaB shows quantification of Oct4 and Cdx2 immunopositive cells in cultured rat ICMs. FIG. 11C shows Oct4 and Nanog immunostaining of ICMs after 4 days culture in 3i. FIG. 11D shows primary colony in 3i 4 days after disaggregation of ICM outgrowth.

FIGS. 12A-12E shows the morphology, clonal expansion, and chromosome complement of rat embryo derived cells propagated in 3i. FIG. 12A shows representative colony of cells passaged on 3i on feeders. FIG. 12B shows cells passaged without feeders on fibronectin in 3i. FIG. 12C shows immunofluorescent staining of 3i colonies for Oct4 and Nanog. FIG. 12D shows RT-PCR analysis of marker expression in rat embryo derived 3i cells compared with E14Tg2a mouse ES cells (mES), rat ExS cells (rExS) and rat ExS cells expressing mouse Oct and mouse Nanog (rExS+mO/mN) transgenes. FIG. 12E shows metaphase chromosomes from 3i rat ES cells (line C).

FIG. 13A shows phase contrast and immunofluorescence images of cells following exposure to serum plus LIF on feeders. FIG. 13B shows differentiated cells after 8 days culture on gelatine in serum-free medium without 3i. FIG. 13C shows characterization of the X-chromosome status in XX rat ES cells. Immunofluorescence for H3K27me3 (green) in undifferentiated and 6 days differentiated XX rat 3i cells and in XX rat neural stem (NS) cells. Undifferentiated cells show diffuse staining (lack of inactive X) while differentiated cells and somatic stem cells exhibit the presence of a H3K27me3 nuclear body (inactive X). Cells were counterstained with Dapi (blue).

FIG. 14A shows histological sections of teratomas. Keratinised epithelium (line C), striated muscle (line B), gut epithelium (line C). FIG. 14B shows images of intact embryo and head to tail transverse sections (i-x) of E10.5 chimaera generated using GFP expressing line D 3i cells. GFP fluorescence in green, DAPI nuclear staining in blue. FIG. 14C shows coat colour chimaeras derived from cells of line C. Albino snouts denote the recipient Fischer strain (hooded albino), body pigmentation the introduced DA strain cells. FIGS. 14 D to 14F show microsatellite analyses of genomic DNA in adult coat colour chimaeras. Polymorphic microsatellite regions D1Rat122 and D3Rat17 were amplified by PCR from genomic DNA of tail, ear and blood and analysed by agarose gel and fluorescent detection methods, as shown in FIG. 14D and FIGS. 14E to 14F, respectively.

Figure 1:
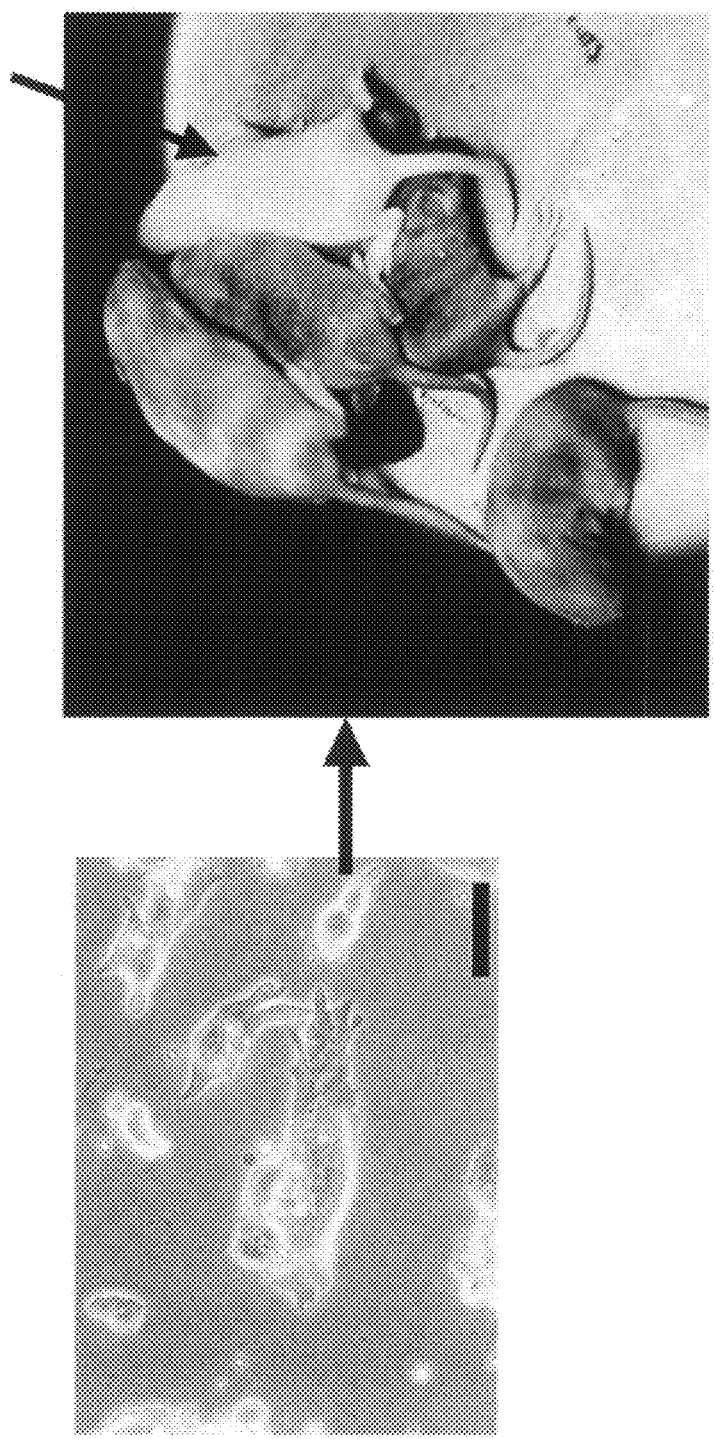
FIG. 1 shows mouse ES cells derived and maintained according to the invention and shows high efficiency of chimera contribution by these ES cells.
Figure 2:
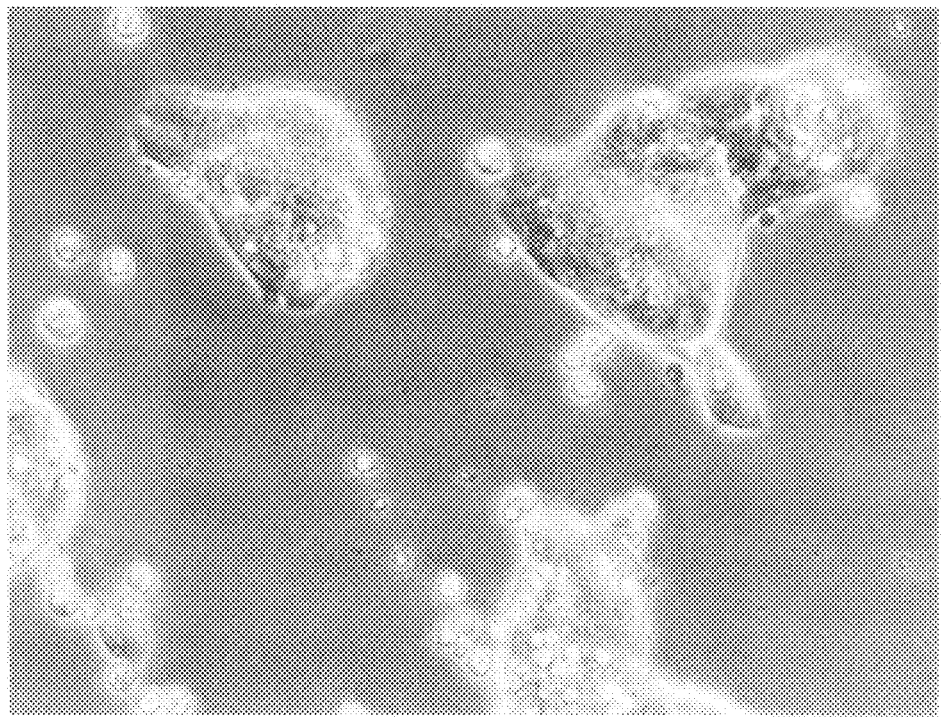
FIG. 2 shows passage 4 mouse ES cells grown in accordance with the invention.

According to a first aspect of the present invention, inhibition of all of GSK3 and MEK and a FGF receptor in a pluripotent cell is used to promote self-renewal of the cell.

In accordance with the present invention, pluripotent stem cells, such as ES cells, are cultured in medium, preferably serum-free, comprising a MEK inhibitor, a GSK3 inhibitor and an antagonist of a FGF receptor (e.g. a small molecule GSK3 inhibitor and a small molecule MEK inhibitor and a small molecule FGFR antagonist). Self renewal of the stem cells for multiple passages is thereby promoted. Hence, inhibition of GSK3, MEK and FGF receptor signalling in the pluripotent cells provides a self renewal stimulus.

The invention has a number of applications. A combination of GSK3 and MEK, MEK and FGFR or GSK3, MEK and FGFR inhibition can be used to grow pluripotent cells, especially ES cells, and, where they have been derived or grown on feeders, to adapt pluripotent cells, especially ES cells, to grow without feeder cells or a layer of feeder cells, often referred to as feeders or feeder cells. A method of expanding stem cells in culture comprises culturing the cells in the presence of a GSK3 inhibitor and a MEK inhibitor, in the presence of a MEK inhibitor and an antagonist of an FGF receptor, or preferably in the presence of a GSK3 inhibitor, a MEK inhibitor and an antagonist of a FGF receptor. Culture medium can be prepared containing one or more GSK3 inhibitors and MEK inhibitors, one or more MEK inhibitors and FGFR antagonists and, optionally, one or more MEK inhibitors, GSK3 inhibitors and FGFR antagonists. ES cells can be derived using GSK3 inhibitors and MEK inhibitors, using MEK inhibitors and FGFR antagonists, or using GSK3 inhibitors, MEK inhibitors and FGFR antagonists, including ES cells from organisms from which ES cells have not hitherto been isolated.

DETAILED DESCRIPTION OF THE INVENTION

Reference to pluripotent cells includes but is not limited to reference to embryonic stem (ES) cells. Characteristic properties of pluripotent cells, including ES cells, include the expression of multiple genes associated with the pluripotent stage of development, the ability to differentiate into cells representative of any and all tissue types present in the source animal, the ability to contribute to chimeras and, particularly, the ability to contribute to the germ line of chimeras. For example true pluripotent cells, such as ES cells, would be expected to express many, if not all, of the pluripotency-associated genes Nanog, Oct4, FGF4, Sox-2 and alkaline phosphatase. In particular, expression of Nanog, Oct4 and Sox-2 is widely regarded as providing a definitive initial indication that a cell is an ES cell. Germ line transmission in chimeras and the ability to generate teratomas or teratocarcinomas comprising differentiated cells from all three primary germ layers (i.e. endoderm, mesoderm and ectoderm) are also widely regarded as definitive indications of a cell being an ES cell.

Reference to GSK3 inhibition refers to inhibition of one or more GSK3 enzymes. Thus a GSK3 inhibitor can inhibit one member, several members or all members of the family of GSK3 enzymes. The family of GSK3 enzymes is well-known and includes but is not limited to GSK3-α and GSK3-β. A number of variants have been described (see e.g. Schaffer et al.; Gene 2003; 302(1-2): 73-81). In specific embodiments GSK3-β is inhibited. GSK3-α inhibitors are also suitable, and in general inhibitors for use in the invention inhibit both. A wide range of GSK3 inhibitors are known, by way of example, the inhibitors CHIR 98014, CHIR 99021, AR-AO144-18, TDZD-8, SB216763 and SB415286. Other inhibitors are known and useful in the invention. In addition, the structure of the active site of GSK3-β has been characterised and key residues that interact with specific and non-specific inhibitors have been identified (Bertrand et al.; J Mol Biol. 2003; 333(2): 393-407). This structural characterisation allows additional GSK inhibitors to be readily identified.

The inhibitors of certain embodiments are specific for GSK3-β and GSK3-α, substantially do not inhibit erk2 and substantially do not inhibit cdc2. Preferably the inhibitors have at least 100 fold, more preferably at least 200 fold, very preferably at least 400 fold selectivity for human GSK3 over mouse erk2 and/or human cdc2, measured as ratio of $IC_{50}$ values; here, reference to GSK3 $IC_{50}$ values refers to the mean values for human GSK3-β and GSK3-α. Good results have been obtained with CHIR 99021 and CHIR 98014, which are both specific for GSK3. Examples of GSK3 inhibitors are described in Bennett C, et al, J. Biol. Chem., vol. 277, no. 34, Aug. 23, 2002, pp 30998-31004 and in Ring D B, et al, Diabetes, vol. 52, March 2003, pp 588-595. Suitable concentrations for use of CHIR 99021 are in the range 0.01 to 100, preferably 0.1 to 20, more preferably 0.3 to 10 micromolar.

GSK3 inhibition can also be conveniently achieved using RNA mediated interference (RNAi). Typically, a double-stranded RNA molecule complementary to all or part of a GSK3 gene is introduced into pluripotent cells, thus promoting specific degradation of GSK3-encoding mRNA molecules. This post-transcriptional mechanism results in reduced or abolished expression of the targeted GSK3 gene. Suitable techniques and protocols for achieving GSK3 inhibition using RNAi are known.

Reference to a MEK inhibitor herein refers to MEK inhibitors in general. Thus, reference to a MEK inhibitor refers to any inhibitor a member of the MEK family of protein kinases, including MEK1, MEK2 and MEK3. Reference is also made to MEK1, MEK2 and MEK3 inhibitors. A MEK inhibitor can inhibit one member, several members or all members of the family of MEK kinases. Examples of suitable MEK inhibitors, already known in the art, include but are not limited to the MEK1 inhibitors PD184352 and PD98059, inhibitors of MEK1 and MEK2 U0126 and SL327, and those discussed in Davies et al (2000) (Davies S P, Reddy H, Caivano M, Cohen P. Specificity and mechanism of action of some commonly used protein kinase inhibitors. Biochem J. 351, 95-105). In particular, PD184352 has been found to have a high degree of specificity and potency when compared to other known MEK inhibitors. Other MEK inhibitors and classes of MEK inhibitors are described in Zhang et al. (2000) Bioorganic & Medicinal Chemistry Letters; 10:2825-2828. Anthrax lethal factor has also been found to exhibit an MAPKK inhibitory profile similar to that of PD098059 (Duesbery et al, 1999). Further suitable MEK inhibitors include PD032509, U0126, SL327 and CI-1055.

Inhibition of MEK kinases can also be conveniently achieved using RNA-mediated interference (RNAi). Typically, a double-stranded RNA molecule complementary to all or part of a MEK gene is introduced into pluripotent cells, thus promoting specific degradation of MEK-encoding mRNA molecules. This post-transcriptional mechanism results in reduced or abolished expression of the targeted MEK gene. Suitable techniques and protocols for achieving MEK inhibition using RNAi are known.

Other approaches for achieving MEK inhibition include using a compound that inhibits or reduces activity of a component of the ras/MAPK cascade. For example, the compound inhibits one or more mitogen activated protein kinases, for example ERK1 and ERK2. Alternatively, the compound inhibits SHP-2, for example by inhibiting binding of the enzyme to gp130, having a similar effect. In a further embodiment, the inhibitor inhibits MEK.

Inhibition of MEK may alternatively be achieved by down-regulation of a component of the ras/MAPK cascade. MKP-3 is an example of a MAP kinase phosphatase and a known downregulator of the ERKs, and has been introduced into an ES cell by way of a transgene.

A number of assays for identifying kinase inhibitors, including GSK3 inhibitors and MEK inhibitors, are known. For example, Davies et al (2000) describe kinase assays in which a kinase is incubated in the presence of a peptide substrate and radiolabelled ATP. Phosphorylation of the substrate by the kinase results in incorporation of the label into the substrate. Aliquots of each reaction are immobilised on phosphocellulose paper and washed in phosphoric acid to remove free ATP. The activity of the substrate following incubation is then measured and provides an indication of kinase activity. The relative kinase activity in the presence and absence of candidate kinase inhibitors can be readily determined using such an assay. Downey et al. (1996) J Biol Chem.; 271(35): 21005-21011 also describes assays for kinase activity which can be used to identify kinase inhibitors.

Reference to an antagonist of fibroblast growth factor (FGF) receptor (FGFR) refers to a polypeptide or small molecule or other antagonist of a FGF receptor, typically inhibiting FGFR1 and/or FGFR2. Thus, a FGF receptor antagonist can be an antagonist of one, several or all members of the FGF receptor family, including but not limited to FGFR1, FGFR2, FGFR3 and FGFR4. Members of the FGF receptor family typically comprise three immunoglobulin-like domains and present a region of acidic amino acids (the acidic box) which can participate in the binding of a member of the FGF family to a FGF receptor. In some cases, molecules comprising only two immunoglobulin-like domains can also function as FGF receptors. A number of FGFR antagonists are known, including but not limited to SU5402 and PD173074. Suitable concentrations of SU5402 are in the micromolar range, such as from 0.1-20 µM, preferably 0.5-10 µM, especially in the range 1-5 µM. We have found that PD173074 can substitute for SU5402 and is fully effective at about 100-fold lower concentrations, consistent with its higher affinity for the FGF receptor. Thus, suitable concentrations for PD173074 are in the range 1-200 nM, preferably from 5-100 nM, especially in the range 10-50 nM. It is also known to inhibit FGR receptor signalling by transgene expression of a dominant negative mutant FGF receptor. In embodiments of the invention, however, it is preferred to use a small molecule antagonist and not a transgenic based antagonism.

Suitable assays for identifying antagonists of FGF receptors are known. For example, a cell line in which signalling via a FGF receptor activates expression of a reporter gene can be used to assess the activity of a potential antagonist.

It has advantageously been found that the use of a MEK inhibitor in combination with a GSK3 inhibitor and an antagonist of the FGF receptor improves the propagation of ES cells.

In preferred embodiments between around 0.1 µM and around 25 µM MEK inhibitor are used. Further preferably, between around 0.1 µM and around 5 µM MEK inhibitor are used, more preferably from 0.2 µM to 2 µM.

Particularly preferred media according to the invention comprise 0.8 µM PD184352, 3 µM CHIR99021 and/or 3 µM SU5402. A particularly preferred medium comprises 0.8 µM PD184352, 3 µM CHIR99021 and 3 µM SU5402, preferably in N2B27 medium. The concentration of SU5402 can be optimized to suit different pluripotent cell lines, typically in the range 1-5 µM (e.g. 2 µM).

In examples below, we have cultured mouse ES cells in the presence of a GSK3 inhibitor together with a MEK inhibitor and, in a specific example, an antagonist of the FGF receptor to promote self renewal. In other specific examples, a method of promoting self-renewal of mouse pluripotent cells in culture comprises inhibiting GSK3 and MEK or inhibiting GSK3, MEK and an FGF receptor.

Optionally, activating gp130 downstream signalling can also be employed to further enhance the promotion of self renewal by inhibiting GSK3 and MEK. Molecules that activate gp130 downstream signalling are sometimes referred to as gp130 activators or gp130 agonists. Activation of one or more gp130 downstream signalling pathways can be achieved by use of a cytokine acting through gp130, for example a cytokine or other agonist of the LIF receptor. Cytokines capable of acting through gp130, and thus of activating gp130 signal transduction, include but are not limited to LIF, ciliary neurotrophic factor (CNTF), cardiotrophin, oncostatin M, IL-6 plus sIL-6 receptor, hyper IL-6 and IL-11. Suitable cytokines include mimetics, fusion proteins or chimaeras that can bind to and/or activate signalling though gp130. The role of cytokines acting through gp130 in the presence of serum is well established, but the capacity of those cytokines to sustain undifferentiated cells in the absence of serum is limited.

An advantage of the invention is that in the presence of a GSK3 inhibitor, a MEK inhibitor and, optionally, an antagonist of the FGF receptor, pluripotent cells can be grown in defined medium. A particular advantage associated with using the combination of a GSK3 inhibitor, a MEK inhibitor and an antagonist of the FGF receptor is that it is not necessary for the medium to contain other growth factors, such as insulin, N2B27, or a gp130 agonist (e.g. LIF). The present invention therefore enables alternative and/or improved culture of ES cells in medium that is free of serum, serum extract, feeder cells and feeder cell extract.

Purported embryonic stem cells have been reported from a number of mammalian sources including mouse (Bradley et al (1984) Nature 309: 255-56), American mink (Mol Reprod Dev (1992) December; 33(4):418-31), pig and sheep (J Reprod Fertil Suppl (1991); 43:255-60), hamster (Dev Biol (1988) May; 127(1):224-7) and cow (Roux Arch Dev Biol (1992); 201: 134-141). It is noted, however, that in some instances multipotent or pluripotent cells have been designated "ES cells" or "ES-like cells" in the absence of complete characterization. ES cell status has sometimes been assigned based on cell morphology, the observation of some spontaneous differentiation in culture, the formation of cystic embryoid bodies, or the expression of a gene associated with the pluripotent stage of development. However, more rigorous characterization of purported ES cells is desirable in order to establish whether the cells are indeed ES cells. This is confirmed in U.S. Pat. No. 6,271,436, which indicates that many previous attempts to derive ES cells, e.g. porcine ES cells, have failed to demonstrate conclusively that the reported cells were pluripotent ES cells.

Characteristic properties of ES cells include the expression of multiple genes associated with the pluripotent stage of development, the ability to differentiate into cells representative of any and all tissue types present in the source animal, the ability to contribute to chimeras and, particularly, the ability to contribute to the germ line of chimeras. For example true ES cells would be expected to express many, if not all, of the pluripotency-associated genes Nanog, Oct4, FGF4, Sox-2 and alkaline phosphatase. In particular, expression of Nanog, Oct4 and Sox-2 is widely regarded as providing a definitive initial indication that a cell is an ES cell. Germ line transmission in chimeras and the ability to generate teratomas or teratocarcinomas comprising differentiated cells from all three primary germ layers (i.e. endoderm, mesoderm and ectoderm) are also widely regarded as definitive indications of a cell being an ES cell.

Specific examples herein use mouse and human ES cells and also rat cells from primary outgrowths. It will be appreciated that the methods and compositions of the present invention are suitable for adaptation to culturing of other mammalian or avian pluripotent cell cultures, including primate, especially human, rodent, especially mouse and rat, bovine, ovine, and porcine pluripotent stem cells, especially ES cells. In other embodiments, the methods and compositions of the invention can be used to culture pluripotent cells from primary outgrowths of bovine, ovine and porcine embryos.

The methods and compositions of the present invention are particularly suitable for culturing pluripotent cells, including ES cells, that express one or more, preferably any two or more, of Nanog, Oct4, FGF4, Sox-2 and alkaline phosphatase. In preferred embodiments, the pluripotent cells express Nanog, Oct4, and Sox-2. Typically the pluripotent cells are morphologically undifferentiated in culture and can be maintained in culture for a prolonged period, typically in excess of at least 10, 20 or 50 passages, without significant differentiation or loss of viability or loss of pluripotent cell characteristics. It is envisaged that pluripotent cells isolated or cultured in the media or using the methods of the invention will be capable of being maintained in culture for about two weeks or longer. For example, the cells may be capable of being maintained in culture for four, six, eight, ten, twelve or more weeks and still substantially retain their original characteristics, including the specific characteristics of pluripotent cells described herein. By way of example, rat pluripotent cells isolated using the procedures described herein have been subjected to continuous culture for six months with no deterioration in growth rate and no significant differentiation.

Such characteristics include the ability to contribute to a chimera, including contributing to the germ line of the chimera. For example mouse ES cells can contribute to a chimera, for example when injected into a mouse blastocyst. Similarly, rat pluripotent and ES cells, provided for the first time herein, can contribute to a chimera in which all cells of the chimera are rat cells. ES cells derived from other mammals, e.g. as described herein, are similarly able to contribute to a chimera. The ES cells will also be capable of forming a teratoma or teratocarcinoma, for example following injection of ES cells into immunodeficient mice. Typically the teratoma or teratocarcinoma will comprise differentiated cells from all three germ layers, although in some cases cells from only one or two of the germ layers may be observed.

A second aspect of the invention provides a method of culture of pluripotent cells, especially ES cells, so as to promote self renewal, comprising maintaining the cells in medium containing:—
(1) an inhibitor of GSK3;
(2) an inhibitor of MEK; and, optionally,
(3) an antagonist of an FGF receptor.

Methods of the invention can be used generally for growing pluripotent cells, including growing ES cells in medium which is free of serum and free of serum extract, which cells have previously been passaged in the presence of serum or serum extract. Preferably, such methods are also carried out in the absence of feeder cells and/or feeder cell extracts. For example, culture of ES cells can be carried out comprising the steps of:—
maintaining the ES cells in a pluripotent state in culture, optionally on feeders;
passaging the ES cells at least once;
withdrawing the serum or the serum extract from the medium and withdrawing the feeders (if present), so that the medium is free of feeders, serum and serum extract; and
subsequently maintaining ES cells in a pluripotent state in the presence of an inhibitor of GSK3, a MEK inhibitor and, optionally, an FGFR antagonist.

The present invention also provides a method of obtaining a transfected population of ES cells, comprising:—
transfecting ES cells with a construct encoding a selectable marker;
plating the ES cells;
culturing the ES cells in the presence of a MEK inhibitor, a GSK3 inhibitor and, optionally, an FGFR antagonist; and
selecting for cells that express the selectable marker.

Further optionally, the cells are cultured in the presence of a MEK inhibitor, a GSK3 inhibitor and an activator of a gp130 downstream signalling pathway.

The selectable marker may encode antibiotic resistance, a cell surface marker or another selectable marker as described e.g. in EP-A-0695351, and preferably comprises a nucleotide sequence encoding the selectable marker operatively linked to a promoter which preferentially expresses the selectable marker in desired cells.

In a further embodiment, the present invention provides a method of culture of pluripotent, especially ES, cells, comprising the steps of transferring an individual cell to a culture vessel, such as an individual well on a plate, and culturing the cell in the presence of a GSK3 inhibitor, a MEK inhibitor and, optionally, an FGFR antagonist, so as to obtain a clonal population of pluripotent, especially ES, cells, all of which are progeny of a single cell. Optionally, the cells may also be cultured in the presence of an activator of gp130 downstream signalling pathways.

Once a stable, homogenous culture of ES cells is obtained, the culture conditions can be altered to direct differentiation of the cells into one or more cell types selected from ectodermal, mesodermal or endodermal cell fates. Addition of, or withdrawal of cytokines and signalling factors, can enable the derivation of specific differentiated cell populations at high efficiency. Differentiation of an ES cell towards a non-neuroectodermal fate may be achieved by maintaining the ES cell in the presence of a cytokine acting through gp130, a MEK inhibitor and a GSK3 inhibitor and then withdrawing the cytokine whilst maintaining the GSK3 inhibitor and MEK inhibitor and/or adding a further signalling molecule capable of directing differentiation. Alternatively, the cells may be maintained in the presence of a MEK inhibitor and a GSK3 inhibitor and then differentiation directed by withdrawing one or both of the inhibitors and/or adding a signalling molecule capable of directing differentiation. The methods described above all optionally include the step of obtaining and/or isolating a differentiated cell which is the product of the process.

Further aspects of the invention provide for cell culture media. One medium is for self-renewal of pluripotent, especially ES, cells, the medium comprising an inhibitor of GSK3, an inhibitor of MEK and an FGFR antagonist. The medium may also optionally comprise an activator of a gp130 downstream signalling pathway. Another medium of the invention is a stem cell culture medium, comprising an inhibitor of GSK3, a MEK inhibitor and an FGFR antagonist. All media preferably further comprises basal medium. Further, all media is preferably free of an agonist of gp130, hence is preferably free of LIF.

The invention provides medium that is free of serum and serum extract. One such medium comprises:—
basal medium;
a MEK inhibitor;
a GSK3 inhibitor; and
an iron-transporter;
wherein the medium is optionally free of serum and serum extract.

The medium preferably also comprises an FGFR antagonist. The medium may also optionally comprise an activator of a gp130 downstream signalling pathway.

Preferred medium for pluripotent stem cells, especially rat or mouse cells, may be free of serum and of gp130 agonists and comprises a MEK inhibitor, a GSK3 inhibitor, and an antagonist of an FGF receptor. Substitutions of media components can be made as described herein.

Basal medium is medium that supplies essential sources of carbon and/or vitamins and/or minerals for the cells. The basal medium is generally free of protein and incapable on its own of supporting self-renewal of cells. The iron transporter provides a source of iron or provides the ability to take up iron from the culture medium. Suitable iron transporters include transferrin and apotransferrin. It is preferred that the medium further comprises one or more of insulin or insulin-like growth factor and albumin (preferably recombinant) or albumin substitute, and is free of feeder cells and feeder cell extract. The medium may also comprise an inhibitor of apoptosis or any other component that promotes the maintenance of pluripotent cells in culture. For example, the medium can comprise a ROCK inhibitor, e.g. Y-27632 (Watanabe et al., Nature Biotechnology (2007) 25(6): 681-686).

A particular medium of the invention comprises MEK inhibitor, GSK3 inhibitor, insulin, albumin and transferrin, with or without additional basal medium. In this medium, LIF can be optionally included and can be substituted by other activators of gp130 signalling, though preferred medium comprises the gp130 receptor binding cytokine, LIF, suitable concentrations of which are generally between 10 U/ml and 1000 U/ml, more preferably between 50 U/ml and 500 U/ml, even more preferably in the region of 100 U/ml. The GSK3 and MEK inhibitors are preferably as described herein in more detail.

The invention further provides a method of deriving a pluripotent cell from a blastocyst, comprising:—
(1) obtaining a blastocyst;
(2) culturing the blastocyst in the presence of a MEK inhibitor, a GSK3 inhibitor and, optionally, an antagonist of an FGF receptor, to obtain an inner cell mass;
(3) dissociating the inner cell mass;
(4) isolating a cell or cells from the dissociated inner cell mass; and
(5) culturing the isolated cell or cells in the presence of a MEK inhibitor, a GSK3 inhibitor and an antagonist of an FGF receptor.

Optionally, the isolated cell or cells are cultured in the presence of a MEK inhibitor, a GSK3 inhibitor and an activator of gp130 downstream signalling. An antagonist of an FGF receptor may also be present.

Preferably, the method comprises culturing the blastocyst in LIF, more preferably for a period of from 2 to 4 days. The isolated cell or cells are preferably cultured in serum free medium. Typically, the cells are replated as clumps. The blastocyst is also preferably cultured in serum free medium, optionally in the absence of an agonist of the BMP receptor.

It is further preferred, according to the invention, that culture of cells is carried out in an adherent culture, which may be promoted by the inclusion of a cell adhesion protein on culture substrate. It is also preferred to culture pluripotent cells according to the invention in monolayer culture, though it is optional for cells to be grown in suspension culture or as pre-cell aggregates; cells can also be grown on beads or on other suitable scaffolds such as membranes or other 3-dimensional structures.

Surprisingly, it has been found that the compositions and methods of the present invention are particularly suitable for the derivation of pluripotent and ES cells from rats. Although some reports claim that rat pluripotent cells have been produced (Vassilieva et al. (2000) Exp Cell Res 258(2): pp 361-373; Schultze et al. (2006) Methods Mol Biol 329: pp 45-58), the evidence presented is far from conclusive. Schultze et al. acknowledge that most attempts to derive and maintain rat ES cell lines have failed and that researchers have been forced to abandon this line of research. Similarly, Vassilieva et al. observe that previous attempts to generate rat ES cells have failed as the purported ES cells could only be maintained in culture for a short time or the experiments were not repeatable. Moreover, cell lines described in the art have been demonstrated not to be pluripotent ES cells. The purported designation "ES cell" has been assigned based on the observation of limited differentiation in culture, the formation of embryoid bodies or the expression of an incomplete set of pluripotency-associated markers, often only one gene. However, such indications do not permit unambiguous identification of ES cells, and may merely indicate that multipotent, not pluripotent, cells have been isolated. Many key indicators of pluripotency have not been demonstrated, and there remains considerable doubt as to whether rat ES cells have in fact been isolated. In particular, there have been no reported rat cell lines for which (i) the ability to form teratomas or teratocarcinomas comprising differentiated tissues from all three germ layers, (ii) the ability to colonise the germ line of a chimera or (iii) the coordinated expression of multiple pluripotency-associated genes, especially coordinated expression of Nanog, Oct4 and Sox-2, have been demonstrated.

In a comparative example, set out in detail below, a report of obtaining purported rat ES cells has been reproduced without success.

However, the methods of the invention have been shown to be suitable for the derivation of rat pluripotent and ES cells, which have been isolated from dissociated primary outgrowths of the inner cell mass of rat blastocysts. Thus, the present invention provides a method of deriving a pluripotent rat cell from a blastocyst, comprising:—
(1) obtaining a blastocyst;
(2) culturing the blastocyst in the presence of a MEK inhibitor and a GSK3 inhibitor, to obtain an inner cell mass;
(3) isolating and dissociating the primary outgrowths of the inner cell mass;
(4) isolating a cell or cells from the dissociated primary outgrowths of the inner cell mass; and
(5) culturing the isolated cell or cells in the presence of a MEK inhibitor, a GSK3 inhibitor and, optionally, an antagonist of an FGF receptor.

Typically, the rat blastocyst will be cultured for a period of from 2 to 4 days, e.g. 3 days. The blastocyst may also be cultured in the presence of a MEK inhibitor, a GSK inhibitor and an antagonist of an FGF receptor. The isolated rat pluripotent cells typically have the properties of pluripotent and ES cells described herein.

In some embodiments, the method is modified such that the inner cell mass is isolated from the blastocyst by removal of the trophectoderm, and the inner cell mass is cultured in the presence of a MEK inhibitor, a GSK3 inhibitor and an antagonist of an FGF receptor The methods described herein are also suitable for deriving pluripotent cells from other animals. For example, the steps described herein have been performed on bovine and ovine blastocysts, thus allowing the derivation of pluripotent cells from bovine and ovine primary outgrowths. The methods described herein have also been used to derive human pluripotent cells from human blastocysts. The methods can also be performed on porcine blastocysts to derive pluripotent cells from porcine primary outgrowths.

The methods described herein have also been used to derive pluripotent cells from non-permissive strains of mice. Thus, the present invention also provides murine pluripotent cells from strains of mouse that have hitherto been considered to be non-permissive to the derivation of ES cells.

A further aspect of the invention provides a rat pluripotent cell obtainable by a method of the invention. The invention also provides a pluripotent rat cell expressing two or more of Nanog, Oct4, FGF4 and Sox-2. Preferably the pluripotent rat cell expresses Nanog, Oct4 and Sox-2. The pluripotent rat cell may also express alkaline phosphatase and may possess any of the characteristics of pluripotent and ES cells described herein, such as the ability to colonise the germ line of a chimera and the ability to form a teratoma or teratocarcinoma comprising differentiated tissues derived from endoderm, mesoderm and ectoderm.

Accordingly, the present invention provides a pluripotent rat cell expressing Rex1, Stella (Dppa3), FGF4 and Sox-2. The pluripotent rat cells of the invention may also express one or more additional markers of the pluripotent state and or markers associated with the inner cells mass, including Errβ, Pecam 1, Tbx3, and Gbx2. The pluripotent rat cells do not express FGF5. In addition, the rat pluripotent cells of the invention do not express, or do not express significant levels of, genes associated with the epiblast and early germ layers such as Otx2, Eomes, Foxa2, brachyury, Gata6, Sox17 and Cer1. Analysis of rat pluripotent cells of the invention has failed to detect expression of the hypoblast and definitive endoderm markers Gata6 and Sox17, the mesoderm markers brachyury and Flk1, and the neurectoderm markers Pax6 and nestin. These characteristics, and other characteristics of the rat pluripotent cells of the invention, will also be exhibited by other mammalian pluripotent cells of the invention.

Thus, the pluripotent cells of the present invention can be distinguished from the stem cells (referred to as EpiSCs) recently derived from the post-implantation egg cylinder stage epiblast (Tesar P. J. et al. Nature (2007) 448: 196-9; Brons I. G. M. et al. Nature (2007) 448: 191-5) which show little or no ability to reincorporate into the preimplantation embryo and contribute to chimaeras. In contrast to the pluripotent cells of the present invention, EpiSCs cannot be readily propagated after dissociation into single cells, do not express markers of ES cells or early epiblast, and require maintenance in FGF2 plus activin, under which conditions the pluripotent cells of the invention are induced to differentiate.

The pluripotent cells of the invention, including rat, ovine, bovine and porcine pluripotent cells, are morphologically undifferentiated in culture. The pluripotent cells of the invention are capable of being maintained in culture for about 2 weeks or longer. Preferably the pluripotent cells are capable of being maintained in culture for, four, six, eight, ten or twelve weeks or longer, more preferably for about three, six, nine or twelve months or longer. After being maintained in culture, the progeny of the pluripotent cell retain one or more, preferably all, of the characteristics of the original pluripotent cell.

The pluripotent cells of the invention are capable of contributing to a chimaera. In particular they are capable of contributing to a chimaera in which all cells of the chimaera are cells of the same species as the pluripotent cell. For example, if a pluripotent rat cell is used to produce a chimaera, all of the cells of the chimaera are rat cells. The pluripotent cells of the invention are preferably capable of contributing to the germ line of a chimaera.

The pluripotent cells of the invention are capable of forming a teratomas or teratocarcinoma in which differentiated cells from all three germ layers, i.e. endoderm, mesoderm and ectoderm, are present.

It is also preferred that the pluripotent cells of the invention have a normal karyotype, i.e. the karyotype of the pluripotent cells corresponds to the normal karyotype of cells from the same species and/or strain.

Typically, the pluripotent cells of the invention, including rat, ovine, bovine and porcine pluripotent cells, exhibit one or more, preferably two, three, four or five, and most preferably all of the following characteristics:
a) the ability to form a chimaera;
b) the capability of growth and/or proliferation as a single cell in culture;
c) expression of Rex1, Stella, FGF4 and Sox-2;
d) they are induced to differentiate or fail to grow in the presence of activin and/or FGF;
e) they are not induced to differentiate or die by activin receptor blockade; and
f) growth and/or proliferation of the pluripotent cell is supported by the presence of a MEK inhibitor, a GSK3 inhibitor and, optionally, an antagonist of an FGF receptor.

Without wishing to be bound by any particular theory, it is believed that MEK inhibition is particularly important for maintenance of the pluripotent phenotype. Thus, the invention also provides pluripotent stem cells and populations thereof maintained in the presence of a MEK inhibitor. Preferably, the pluripotent cells and populations are maintained in the presence of a MEK inhibitor and one or more additional factors suitable for maintaining the pluripotent state, including but not limited to a GSK3 inhibitor, an antagonist of an FGF receptor and a cytokine acting through gp130.

The invention also provides a population of pluripotent rat cells as described herein. The populations of rat pluripotent cells obtained by particular methods of the invention and thus provided by the invention have been found to be highly homogenous, containing at least 85%, preferably at least 90% more preferably at least 95% pluripotent cells, assessed according to the characteristics mentioned above. In specific embodiments of the invention cultures of rat pluripotent cells of 98% purity and more have been obtained. For example, the invention provides a population of pluripotent rat cells in which at least 95% of the cells retain the characteristics of pluripotent cells. Preferably at least 95% of the cells express Nanog and/or Oct4.

In another aspect, the invention provides a culture of pluripotent rat cells, comprising pluripotent rat cells and a culture medium comprising a MEK inhibitor. Preferably the medium further comprises a GSK3 inhibitor and/or an antagonist of an FGF receptor. Optionally, the medium contains one or more additional components suitable for supporting the growth of pluripotent cells, for example one or more of the components described herein.

The invention also provides pluripotent cells derived from other animals described herein, e.g. bovine, ovine and porcine pluripotent cells, obtainable by a method of the invention. Such pluripotent cells, according to the invention, will possess one or more of the characteristics of pluripotent and ES cells described herein.

Accordingly, the invention provides a pluripotent mammalian cell other than a pluripotent mouse cell expressing two or more of Nanog, Oct4, FGF4 and Sox-2. Preferably the pluripotent cell expresses Nanog, Oct4 and Sox-2. More preferably, the pluripotent cell further expresses alkaline phosphatase. In preferred embodiments, the pluripotent cell expresses Rex1, Stella, FGF4 and Sox-2. Typically, the pluripotent cell does not express FGF5. The pluripotent cells of the invention may also express one or more additional markers of the pluripotent state and or markers associated with the inner cells mass, including Errβ, Pecam 1, Tbx3, and Gbx2. In addition, the pluripotent cells of the invention do not express, or do not express significant levels of, genes associated with the epiblast and early germ layers such as Otx2, Eomes, Foxa2, brachyury, Gata6, Sox17 and Cer1.

The invention also provides populations of pluripotent cells as described herein, including populations of bovine, ovine and porcine pluripotent cells. The populations of pluripotent cells obtained by particular methods of the invention and thus provided by the invention preferably contain at least 85%, preferably at least 90% more preferably at least 95% pluripotent cells, assessed according to the characteristics mentioned above. In some specific embodiments, the invention provides populations containing 98% pluripotent cells and more. For example, the invention provides a population of pluripotent cells in which at least 95% of the cells retain the characteristics of pluripotent cells. Preferably at least 95% of the cells express Nanog and/or Oct4.

It has been found that populations of ES cells cultured in the media described herein, particularly media comprising a MEK inhibitor, a GSK3 inhibitor and an antagonist of an FGF receptor, display significantly greater homogeneity than ES cells maintained in conventional media, e.g. when assayed by immunostaining for pluripotency associated markers such as Nanog or Oct4. The maintenance of pluripotency using the media described herein provides a particular advantage in that highly homogeneous populations of pluripotent cells can be maintained for extended periods in culture without significant cell differentiation and without the need for regular selection for pluripotent cells and against differentiated cell types.

In another aspect, the invention provides a culture of pluripotent cells, comprising pluripotent cells and a culture medium comprising a MEK inhibitor. Preferably the medium further comprises a GSK3 inhibitor and/or an antagonist of an FGF receptor. Optionally, the medium contains one or more additional components suitable for supporting the growth of pluripotent cells, for example one or more of the components described herein.

Culture medium used in the examples of the invention preferably also comprises serum albumin. This can be used in purified or preferably recombinant form, and if in a recombinant form this has the advantage of absence of potential contaminating factors, cytokines etc. The culture medium does not need to contain serum albumin and this component can be omitted or replaced by another bulk protein or by a synthetic polymer (polyvinyl alcohol) as described by Wiles et al.

A particularly preferred medium of the invention is one that is fully defined. This medium does not contain any components which are undefined, that is to say components whose content is unknown or which may contain undefined or varying factors that are unspecified. An advantage of using a fully defined medium is that efficient and consistent protocols for culture and subsequent manipulation of pluripotent cells can be derived. Further, it is found that maintenance of cells in a pluripotent state is achievable with higher efficiency and greater predictability and that when differentiation is induced in cells cultured using a defined medium the response to the differentiation signal is more homogenous than when undefined medium is used.

Methods of the invention also include a method of obtaining a differentiated cell comprising culturing a pluripotent cell as described and allowing or causing the cell to differentiate, wherein the cell contains a selectable marker which is capable of differential expression in the desired differentiated cell compared with other cell types, including pluripotent stem cells, whereby differential expression of the selectable marker results in preferential isolation and/or survival and/or division of the desired differentiated cells. The selectable marker may be expressed in the desired differentiated cells but not expressed in other cell types, or the level of expression may differ between desired differentiated cells and other cell types, thereby allowing selection for expression of the selectable marker. The differentiated cell can be a tissue stem or progenitor cell, including a multipotential or a unipotential stem or progenitor cell, and may be a terminally differentiated cell. The invention also provides differentiated cells obtainable by the method and populations of such differentiated cells.

Examples of differentiated cells that can be obtained according to the invention include gonadal stem cells, somatic stem/progenitor cells, haematopoietic stem cells, epidermal stem cells and neuronal stem cells. In one embodiment, the differentiated cell is a neural cell. It will be apparent that other differentiated cell types and populations of differentiated cells can be obtained according to this method.

Generally also, the invention extends to a cell obtained by following any of the methods of the invention described herein. Cells of the invention can be used in assays for drug discovery. Cells of the invention may also be used for cell therapy, and thus a method of the invention comprises using a combination of inhibition of MEK and inhibition of GSK3 and, optionally, antagonism of FGF signalling to derive and/or maintain pluripotent cells, deriving cells for cell therapy therefrom and using those cells in cell therapy. Optionally, the combination is used in the absence of an activator of gp130 downstream signalling.

The invention further provides additional methods for deriving rat, ovine, bovine, and porcine pluripotent cells and pluripotent cells from strains of mouse considered to be non-permissive to the derivation of ES cells.

Accordingly, the invention provides a method of deriving a pluripotent rat cell from a blastocyst, comprising:—
(1) obtaining a blastocyst;
(2) culturing the blastocyst in the presence of a MEK inhibitor and a GSK3 inhibitor, to obtain an inner cell mass;
(3) isolating and dissociating the primary outgrowths of the inner cell mass;
(4) isolating a cell or cells from the dissociated primary outgrowths of the inner cell mass; and
(5) culturing the isolated cell or cells in the presence of a MEK inhibitor, a GSK3 inhibitor and an antagonist of an FGF receptor.

In a related aspect, the invention provides a method of deriving a pluripotent mammalian cell from a blastocyst, comprising:—
(1) obtaining a blastocyst;
(2) culturing the blastocyst to obtain an inner cell mass;
(3) dissociating the inner cell mass;
(4) isolating a cell or cells from the dissociated inner cell mass; and
(5) culturing the isolated cell or cells in the presence of a MEK inhibitor, a GSK3 inhibitor and an antagonist of an FGF receptor.

Optionally, the method comprises culturing the blastocyst in LIF. In preferred embodiments, the blastocyst is cultured in the presence of a MEK inhibitor, a GSK3 inhibitor and, optionally, an antagonist of an FGF receptor.

In specific embodiments, the blastocyst is a rat blastocyst, a bovine blastocyst, an ovine blastocyst, a porcine blastocyst or a murine blastocyst from a mouse strain that is non-permissive for the derivation of ES cells.

In some embodiments the cell or cells of step (4) are isolated from dissociated primary outgrowths of the inner cell mass.

The methods of deriving pluripotent cells provided by the invention preferably provide a pluripotent cell that expresses one or more of Nanog, Oct4, FGF4, Sox-2 and alkaline phosphatase, more preferably any two or more of Nanog, Oct4, FGF4, Sox-2 and alkaline phosphatase. In a preferred embodiment, the pluripotent cell expresses Nanog, Oct4 and Sox-2 and preferably the pluripotent cell further expresses alkaline phosphatase. In a particularly preferred embodiment, the pluripotent cell expresses Rex 1, Stella, FGF4 and Sox-2. It is also preferred that the pluripotent cell does not express FGF5.

The methods of the invention permit the provision of a pluripotent cell that is morphologically undifferentiated in culture. Typically, the pluripotent cell is capable of being maintained for extended periods in culture, as described herein. For example, the pluripotent cell is capable of being maintained in culture for about two weeks or longer. Preferably, the pluripotent cell is capable of being maintained in culture for about 6 months or longer. Typically, the progeny of the pluripotent mammalian cell retain the characteristics of the original pluripotent mammalian cell after being maintained in culture.

The methods of the invention provide pluripotent cells that are capable of contributing to a chimera. In particular, they are capable of contributing to a chimaera in which all cells of the chimera are cells of the same species as the pluripotent mammalian cell. Preferably, the pluripotent cells are capable of contributing to the germ line of a chimera.

The pluripotent cells produced by the methods of the invention are additionally capable of forming a teratoma or teratocarcinoma in which differentiated cells from all three germ layers are present. The pluripotent cells are capable of growth and/or proliferation as a single cell in culture, are induced to differentiate or fail to grow in the presence of activin and/or FGF and are not induced to differentiate by activin receptor blockade. Growth and/or proliferation of the pluripotent mammalian cells is supported by the presence of a MEK inhibitor, a GSK3 inhibitor and, optionally, an antagonist of an FGF receptor.

In further aspects of the invention, there are provided a rat pluripotent cell, an ovine pluripotent cell, a bovine pluripotent cell, a porcine pluripotent cell and a murine pluripotent cell from a non-permissive strain of mouse obtainable by the methods of the invention. The invention also provides populations of pluripotent cells obtainable by the methods of the invention.

In preferred embodiments of all aspects of the invention the pluripotent cell or cells are ES cells.

A further aspect of the invention provides a method of obtaining a genetically engineered rat comprising genetically modifying a rat pluripotent cell and introducing the pluripotent cell into a rat embryo to produce a genetically modified rat.

A still further aspect of the invention provides a method of obtaining a genetically engineered non-human mammal other than a mouse comprising genetically modifying a mammalian pluripotent cell and introducing the pluripotent cell into a non-human mammalian embryo to produce a genetically modified mammal.

The genetically engineered mammal may, for example, be any non-human mammal including a rat, cow, sheep or pig. In a preferred embodiment the genetically engineered mammal is homozygous null for a gene of interest. In another embodiment, the genetically modifying comprises replacing a gene in the rat or non-human mammal with a corresponding human gene. In further embodiments, the genetically modifying comprises knocking out one or more genes of interest or targeted insertion of a gene of interest. Such genetic manipulation can be carried out using techniques readily available to the person of skill in the art.

The invention also provides a genetically engineered rat and genetically engineered non-human mammal other than a mouse obtainable by the methods of the invention. Such genetically engineered mammals can be used in several applications, for example in assessing the physiological role of one or more genes of interest. Another use of a genetically engineered rat or a genetically engineered non-human mammal of the invention is in drug discovery and/or testing. This can, in some embodiments, include toxicity studies, e.g. to evaluate potential side effect of a potential drug. In further embodiments, genetically engineered rats or genetically engineered non-human mammals of the invention are used as models for human or animal disease.

The use of genetically modified rats of the invention may be particularly advantageous as the rat is the preferred model organism in many areas of biomedical research. For example, assessments of behavioural recovery and cognitive repair are considerably more sophisticated in rats than in mice.

A number of advantages of the invention are described above or apparent. Cell culture components may be identified which are relatively non-toxic and cell permeable. The MEK inhibitors, GSK3 inhibitors and FGFR antagonists used in specific embodiments of the invention can be purified easily, especially compared to, say, purification of protein cytokines. Recombinant proteins can be expensive to make and the small molecule medium components may be more cheaply produced and more stable in storage, with a wider effective concentration range. In addition, the use of MEK inhibitors, GSK3 inhibitors and/or FGFR antagonists permits the derivation and maintenance of previously unobtainable mammalian pluripotent cell types.

Specific embodiments set out below used a combination of CHIR 99021, PD184352 and SU5402 in a serum-free, fully defined medium and gave improved self renewal of mouse ES cells with very little differentiation. It is occasionally reported when culturing ES cells in the presence of BMP that there is some neurogenesis. This was not seen in the examples of the invention.

The invention is now further described in specific examples.

In the examples the term 2i medium or 2i is used to indicate medium comprising a MEK inhibitor and an antagonist of an FGF receptor. The term 3i medium or 3i is used to indicate medium comprising a MEK inhibitor, a GSK3 inhibitor and an antagonist of an FGF receptor.

EXAMPLES

Example 1

Mouse ES cells were grown in medium containing CHIR99021, PD184352 and SU5402, prepared as follows:—
Concentrations of the Three Inhibitors/Antagonist:

| Compound | Initial concentration | Dilutions | Final Concentration when added to media |
|---|---|---|---|
| CHIR99021 | 10 mM Store at −20 >1 yr | Aliquot stock in 20 µl aliquots. Initial 1:10 dilution with N2B27 media = 1 mM. | 3 µM This concentration |

-continued

| Compound | Initial concentration | Dilutions | Final Concentration when added to media |
|---|---|---|---|
| PD184352 | 10 mM Store at −20 >1 yr | Store at 4° C. Add diluted stock to media at 1:333 to make 3 µM final. Aliquot stock in 10 µl aliquots. Initial 1:100 dilution in N2B27 = 1 ml of 100 µM, store at 4° C. Add to media at 1:125 for 0.8 µM final. | was used for all cell lines 0.8 µM Some cell lines were grown in concentrations varying in the range = 0.5-1 µM |
| SU5402 | 5 mM Store at −20 >1 yr | Initial 1:10 dilution = 0.5 mM in N2B27. Add to media at 1:250 for final concentration of 2 µM | 2 µM Some cell lines may need to be optimised, range = 1-5 µM |

Media:
Preparation of DMEM/F12-N2 Medium

To 100 ml of DMEM/F12 (Gibco 42400-010) add 1 ml of N2 100× stock solution. The final concentration of each component of N2 in the DMEM/F12 medium is:

| | | |
|---|---|---|
| Insulin 25 µg/ml | Putrescine 16 µg/ml | Transferrin 100 µg/ml |
| Sodium Selenite 30 nM | Progesterone 6 ng/ml | BSA 50 µg/ml |

Preparation of Neurobasal/B27:

To 100 ml Neurobasal medium (Gibco 21103-049) add 2 ml of B27 (Gibco 17504-044) and 1-2M L-glutamine (TC stores 1:100)

Preparation of N2 B27 Medium:

Mix DMEM/F12-N2 medium with Neurobasal/B27 medium at the ration of 1:1. The media was used to dilute all compounds and grow the cells.

The medium was used for derivation and maintenance of ES cells from 129 strain mice, and also for derivation of ES cells from the non-permissive mouse strain CBA and partially permissive strain C57BL/6. The medium was used for maintenance of cells in primary outgrowths of rat embryos, indicating that pluripotent rat cells are maintained by the medium in culture.

Thus, ES cells are maintained in a combination of a GSK3 inhibitor, a MEK inhibitor and an antagonist of an FGF receptor and the invention also provides culture methods and media therefor.

Example 2

Rat embryos were collected at 4.5 dpc (E4.5), the zonas removed in acid Tyrodes, and immunosurgery performed to remove the trophectoderm. The inner cell masses were cultured in 4-well plates on feeder layers of gamma-irradiated DIA-M cells (described in Buehr et al. 2003) in the following medium (3I medium):

3 µM Chiron 99021 (a GSK inhibitor)
0.8 µM PD184352 (a MEK inhibitor)
2 µM SU5402 (an FGF receptor antagonist) in N2B27.

Penicillin and streptomycin may be added if necessary.

If desired, primary cultures of mouse embryonic fibroblasts (MEFs) can be used as feeder cells rather than DIA-M cells.

These cultures were maintained for 3 days. After that time the small outgrowths were disaggregated manually, and small clumps of cells were moved on to fresh DIA-M feeders in the same medium.

These cultures were maintained for two weeks. The medium was changed every 2-3 days and the cultures were inspected regularly. If small, clear colonies appeared, these were transferred further in similar conditions, and disaggregated if large enough.

After 2 weeks of culture, colonies of undifferentiated cells were seen in some cultures. Some of these colonies adhered to the feeders but more commonly they rounded up and lifted off the substrate. Cultures were passaged by disaggregating colonies, either with trypsin-EDTA or manually (by drawing a colony into a narrow pipette and expelling the cell clumps into a fresh well). Cultures were maintained on DIA-M feeders and in 3I medium at all times.

Figure 4:
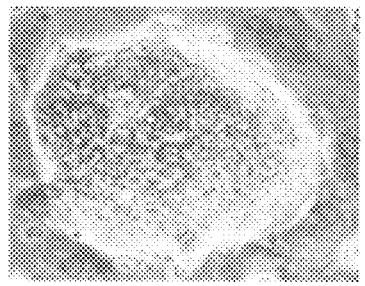
FIG. 4 shows a colony of rat ES cells isolated in accordance with the invention.
Figure 5:
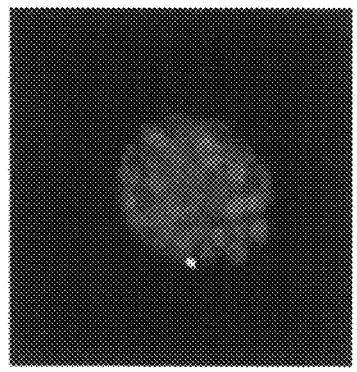
FIG. 5 shows that rat ES cells isolated in accordance with the invention express Nanog.
Figure 6:
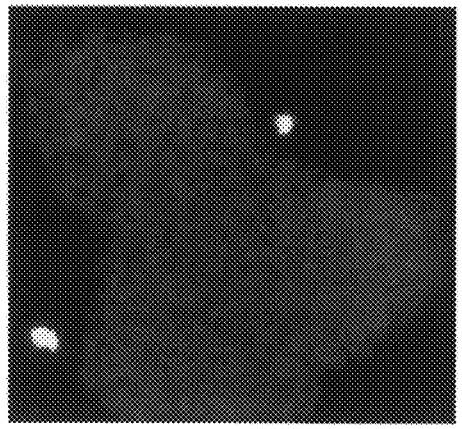
FIG. 6 shows that rat ES cells isolated in accordance with the invention express Oct4.
Figure 7:
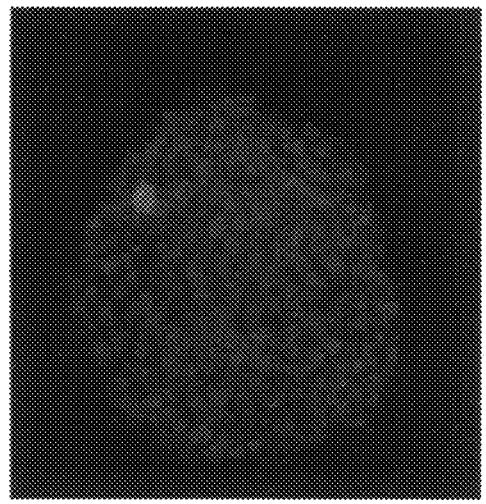
FIG. 7 shows that rat ES cells isolated in accordance with the invention express Cdx-2.
Figure 8:
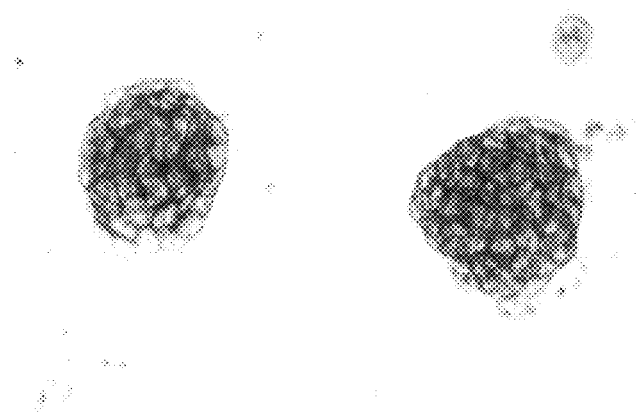
FIG. 8 shows that rat ES cells isolated in accordance with the invention are alkaline phosphatase positive.
Figure 9:
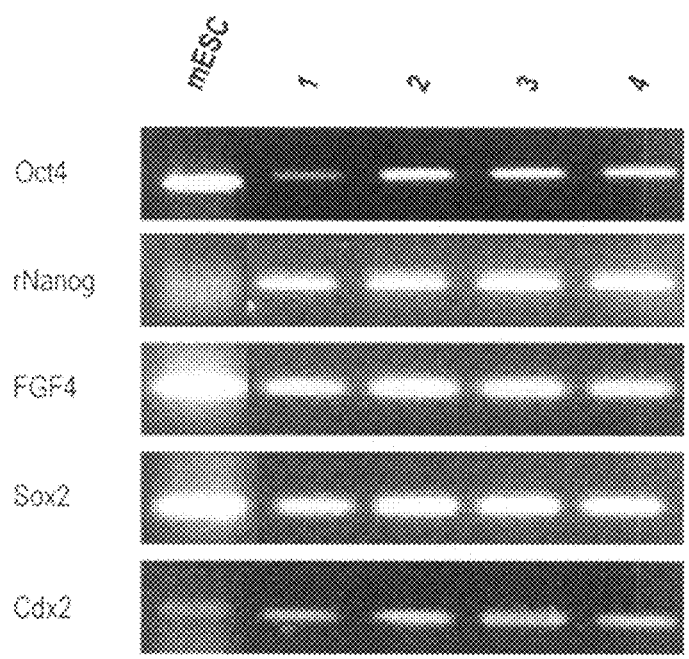
FIG. 9 shows RT-PCR expression data in four rat ES cell lines isolated in accordance with the invention.

Cells derived and cultured in this way were morphologically undifferentiated (FIG. 4) and express the pluripotency-associated genes Nanog (FIGS. 5 and 9) and Oct4 (FIGS. 6 and 9) as well as FGF4, Sox-2 (FIG. 9) and alkaline phosphatise (FIG. 8). The rat cells also expressed the trophectoderm marker Cdx2 (FIGS. 7 and 9).

Reference:
Buehr, M., Nichols, J., Stenhouse, F., Mountford, P., Greenhalgh, C. J., Kantachuvesiri, S., Brooker, G., Mullins, J. M., Smith, A. G. (2003). Rapid loss of oct-4 and pluripotency in cultured rodent blastocysts and derivative cell lines. Biol Reprod 68: 222-229.

Example 3

Figure 10:
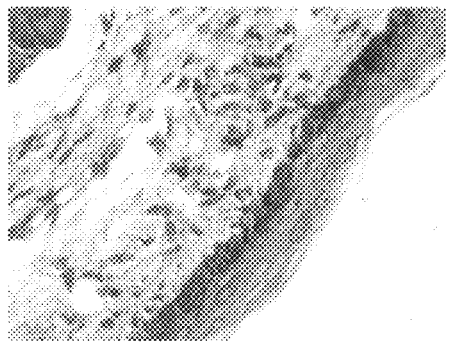
FIG. 10 shows sections of mature differentiated tissue in a teratoma generated from rat ES cells isolated in accordance with the invention.
Figure 10:
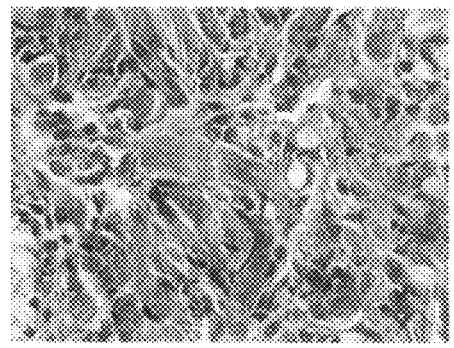
Figure 10:
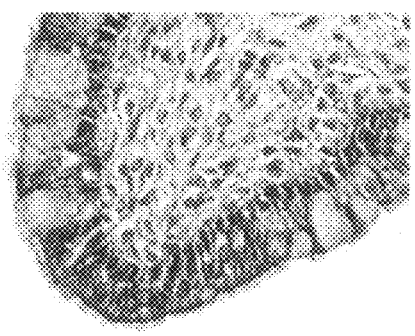

Cells from the rat 148C ES cell line, which was isolated as described in Example 2, were used to generate a teratoma using the standard methodology. In brief, rat ES cells were injected under the kidney capsule of immunodeficient SCID mice. FIG. 10 shows sections of a teratoma generated in one such experiment, in which the animal developed a large tumour and was sacrificed 33 days after the injection.

Mature differentiated tissues can clearly be seen in the sections, notably epidermis, striated muscle and gut epithelium. These tissues are derived, respectively, from ectoderm, mesoderm and endoderm. Thus, differentiated cells derived from each of the three primary germ layers are present, indicating that rat 148C ES cells are pluripotent.

Example 4

Derivation of Pluripotent Stem Cells from Rat Blastocysts

Although embryonic stem (ES) cells have been derived from inbred mice since 1981[1,2], they have not been authenticated for other species. Repeated failure to establish ES cells from other rodents, plus evidence that primate embryo-derived cells differ in key properties from mouse ES cells[3], calls into question the relationship between cultivated stem cells and pluripotent cells of the embryo[4-7]. Here we culture rat embryos in conditions designed to shield the pluripotent state of early epiblast from inductive differentiation signals. This results in reproducible establishment of cultures of cells that express the pluripotency markers Oct4[8] and Nanog[9]. These cells are morphologically undifferentiated and show stable long term expansion. They share molecular features with mouse ES cells and can be induced to differentiate in vitro and form multidifferentiated teratomas in immunocompromised adult mice. Phenotypically and functionally they are distinct from the recently described egg-cylinder derived EpiSCs[3, 10]. Most importantly, upon injection into rat blastocysts they can give extensive contributions to chimaeras. We conclude that pluripotent cells with characteristics of ES cells can be isolated from rat embryos. We suggest that ES cell derivation may be a general facility from naive epiblast cells placed in non-inductive culture.

ES cells arise from pluripotent mouse epiblast cells in the synthetic context of tissue culture[4, 6]. It is unclear whether ES cells themselves are a product of this artificial environment or represent a specific phase of ontogeny that is captured in culture[11]. Empirical experience is that ES cells can reproducibly be derived from certain inbred mouse strains using fibroblast feeders and/or the cytokine leukaemia inhibitory factor (LIF) in combination with selected batches of foetal calf serum or the growth factor bone morphogenetic protein[4, 12]. However, the same conditions do not yield ES cells from all mouse strains and not at all from the rat[13, 14]. We[7] and others[15, 16] have reported the derivation of cell lines from rat embryos that have superficial morphological similarities to ES cells but do not express meaningful levels of the key transcription factor determinants of ES cell identity, Oct4 and Nanog[17], and are not capable of definitive germlayer differentiation in vitro, in tumours or in chimaeras. In our hands such cells give rise only to extraembryonic trophectoblast and hypoblast lineages and we refer to them as extraembryonic stem (ExS) cells[7]. It is possible that repeated failures to derive true ES cells from rat embryos reflect some fundamental difference between the pluripotent epiblast of mouse and rat embryos[18]. Alternatively the culture construction may be inappropriate for maintaining pluripotency, except on particular modified genetic backgrounds produced by extensive inbreeding of laboratory mice.

Figures 11A, 11B:
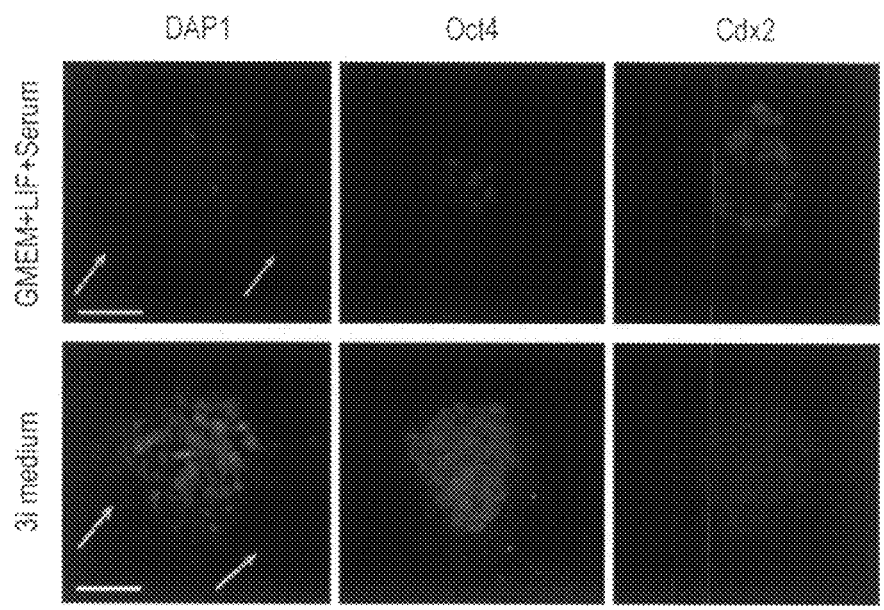

We have formulated a combination of three small molecule inhibitors (3i) to eliminate inductive stimuli for differentiation in mouse ES cell culture (Ying et al, submitted). 3i enables efficient maintenance of pluripotency both in established cell lines and during de novo derivation from mouse embryos. To determine whether this principle was restricted to mice or may be more broadly applicable, we examined the effect of 3i on rat embryo cells. Retained expression of the transcriptional determinant Oct4 can be used as a surrogate assay for presence of undifferentiated cells in primary outgrowths[7]. Oct4 is rapidly extinguished in ICMs cultured in serum containing medium[6, 7] or in serum-free medium. Inner cell masses (ICMs) were isolated from E4.5 rat blastocysts by immunosurgery and plated on feeders to facilitate attachment, and also as a source of leukaemia inhibitory factor (LIF)[7]. Cultures were fixed after 3 or 4 days and analysed by immunostaining (FIG. 11a-c). Concurrent with the previously described loss of Oct4, we observed up-regulation of Cdx2, the trophectoderm determinant and antagonist of Oct4[19]. These changes were not prevented by feeders or soluble LIF, or by culture in serum-free medium without inhibitors. In contrast, in the presence of 3i, we found that Oct4 protein is maintained by the majority of cells in the outgrowth and expression of Cdx2 was suppressed. Furthermore, a second critical marker of pluripotent status, Nanog[9], which is down-regulated in similar fashion to Oct4 in cultured ICMs, was maintained in serum-free medium supplemented with 3i. We dissociated ICMs cultured in 3i medium for 3 days into small clumps, and replated them in the same conditions. Cells remained viable and appeared to proliferate, forming colonies of morphologically undifferentiated cells that continued to express Oct4 and Nanog 4 days later (FIG. 1d).

Following on from these indications that 3i sustains the uncommitted state in primary cultures, we investigated longer term effects. A total of 35 ICMs from rat embryos of two different strains, DA and Fischer 344, were plated on feeders in 3i. After 3 days, 11 of the ICMs had attached and proliferated such that they could be mechanically broken up into small clumps and replated in fresh wells. From four of these replated ICMs, small colonies of undifferentiated morphology developed. After 10 days each of these colonies was transferred intact into a new well. Four days later all had increased appreciably in size. The colonies were then dissociated manually and replated. Further undifferentiated colonies emerged in all cases. We found that these cultures could then be passaged repeatedly, resulting in the establishment of four cell lines, two derived from the Fischer embryos and two from DA embryos. All 4 lines were similar in morphology and growth characteristics. They proliferate as three dimensional aggregates of tightly packed cells (FIG. 12a), typical of ES cells cultured in 3i (Ying et al., submitted). Individual cells have the high nucleus to cytoplasm ratio and prominent nucleoli characteristic of ES cells. They are apolar and lack processes, cytoarchitectural features, or other signs of specialization. Routinely cells were passaged every 3-4 days when colonies reached an intermediate size because they have a tendency to detach from the feeder layer if they become too large. We found that undifferentiated cells were difficult to maintain on gelatin-coated plastic in 3i. Adhesion was poor without feeders and cells tended to aggregate and detach from the substrate. However, on fibronectin-coated dishes attachment was improved and adequate for propagation of undifferentiated cells (FIG. 12b), indicating that the major contribution of feeders is to support cell adhesion rather than provide a specific self-renewal signal. The colonies can readily be dissociated manually by pipetting or enzymatically using Accutase. After dissociation, single cells isolated by micropipette can readily give rise to undifferentiated colonies that can be serially passaged (FIG. 12b). Cells can be cryopreserved and recovered by conventional procedures. Cultures have been expanded continuously for 6 months with no deterioration in growth rate and little or no overt differentiation.

Figure 12C:
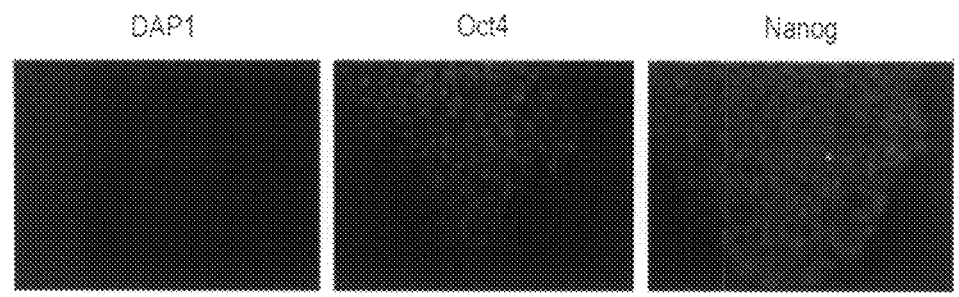
Figure 12D:
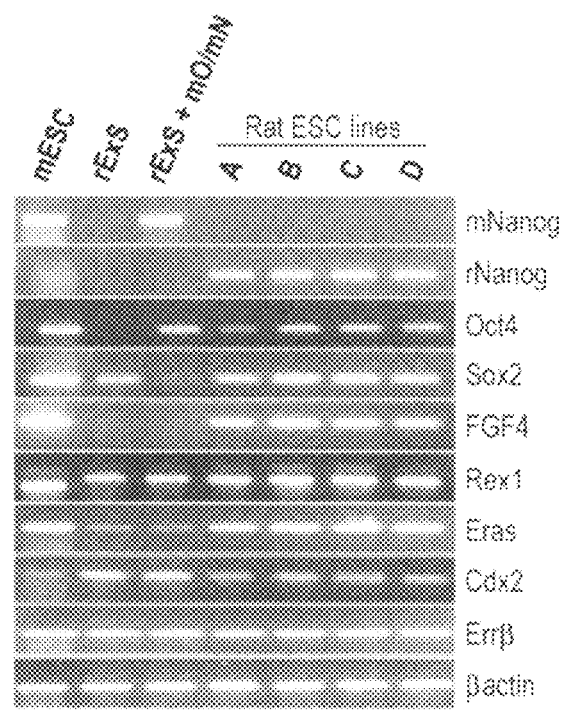
Figure 12D:
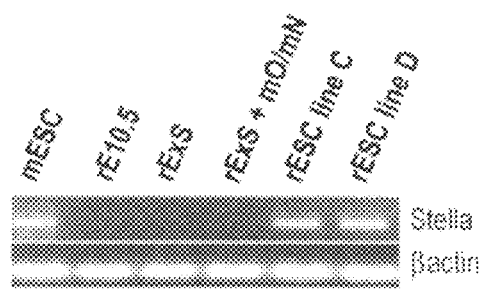
Figure 12E:
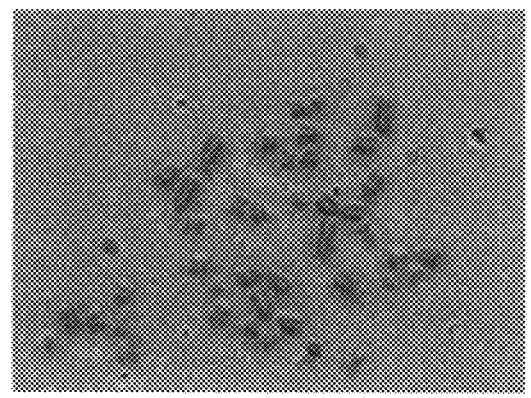

To assess the potential identity of these rat cells we examined expression of key markers of pluripotency and lineage commitment. By immunofluorescence the cells show nuclear expression of Oct-4 and Nanog (FIG. 12c). RT-PCR analysis confirmed expression of these genes along with Rex-1, Errβ, Sox2, Stella and the Oct4/Sox2 target Fgf4 (FIG. 12d). Transcripts for the hypoblast and definitive endoderm markers Gata6 and Sox17, the mesoderm markers brachyury and Flk1, or the neuroectoderm markers Pax6 and nestin were not detected. Primers for amplification of Nanog were designed against sequences specific for the rat gene. These primers consistently yielded products of anticipated size from rat cells but not from mouse ES cells. Conversely, mouse specific primers did not yield any product from the rat cells. The rat identity of the cells was confirmed by preparation of metaphase spreads (FIG. 12e). All 4 lines contained the metacentric and acrocentric chromosomes characteristic of the rat, and distinct from mouse which has only telocentric chromosomes.

In two repeat experiments a total of 41 further ICMs were cultured in 3i. Of these, 13 attached and formed cell masses. These were disaggregated after three days, and primary undifferentiated colonies subsequently appeared in 6 wells. All 6 of these cultures yielded continuously expandable undifferentiated cell lines. These cultures are indistinguishable morphologically from the original 4 lines and all express both Oct4 and Nanog. Subsequently we have derived a further 4 lines from 18 disaggregated ICMs. We conclude that the derivation procedure is reproducible and robust.

Figure 13A:
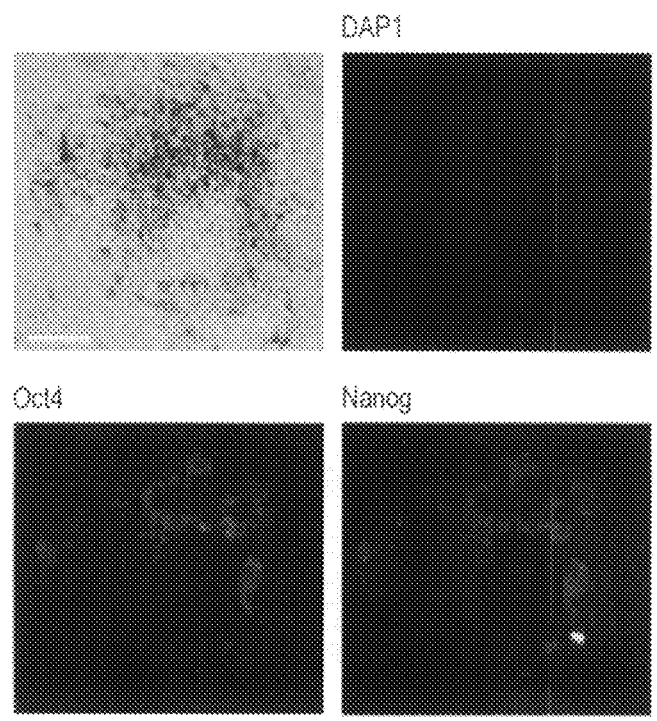
FIGS. 13A-13C show the differentiation of rat 3i cells in vitro.

We investigated the effect of altering the culture conditions on maintenance of the undifferentiated state. We found that the LIF-producing DIA-M feeders used in the derivations[7], could be replaced by standard mouse embryo fibroblasts (MEFs) with no evident compromise. LIF is not included in culture medium, consistent with the sufficiency of 3i for mouse ES cells. Rat cells transferred from 3i to medium supplemented with serum and LIF or BMP and LIF differentiated into various morphologies and lost expression of Oct4 and Nanog (FIG. 13a). These observations indicate that the 3i rat cells have reduced responsiveness to gp130/Stat3 signalling compared with mouse ES cells[20, 21]. This may be a significant contributory factor to previous failures to derive rat ES cells.

Figure 13B:
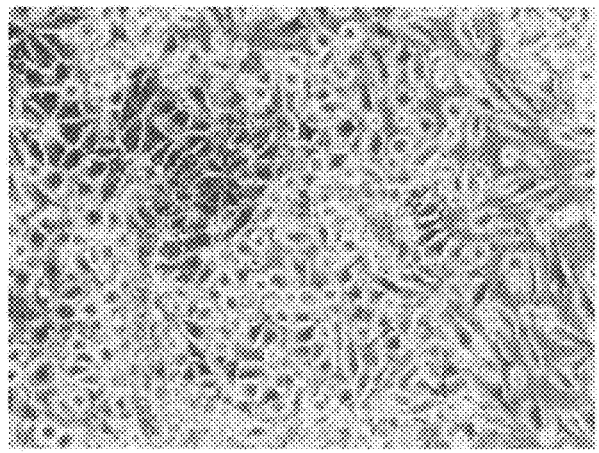

Cells cultured without inhibitors differentiated into various morphologies (FIG. 13b). Culture in Fgfr inhibitor and inhibitor of Mek activation (2i) was adequate to maintain the undifferentiated population without the GSK3 inhibitor, as also seen with mouse ES cells. These findings are consistent with the hypothesis that blockade of FGF/Erk signaling is the critical requirement to sustain the naïve pluripotent state (Ying et al., submitted).

Figure 13C:
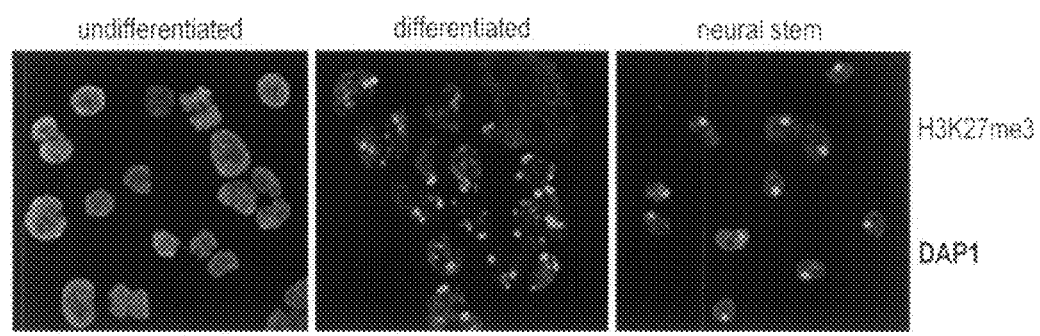

A hallmark of undifferentiated female ES cells and of naïve epiblast is that both X chromosomes are active and upon differentiation one copy is inactivated[22-24]. We stained XX 3i rat cells with an antibody against trimethylated histone 3 lysine 27 (H3K27), an epigenetic silencing mark that distinguishes the inactive X chromosome in interphase nuclei[25]. Cells maintained in 3i showed only diffuse immunoreactivity whereas cells differentiated after exposure to serum for 6 days exhibited a prominent nuclear body diagnostic of the inactive X (FIG. 13c). These data indicate that in undifferentiated XX 3i rat cells the two X chromosomes are active and that one X chromosome is inactivated during differentiation. Therefore 3i rat cells exhibit the appropriate epigenetic status of early epiblast and ES cells.

Figure 14A:
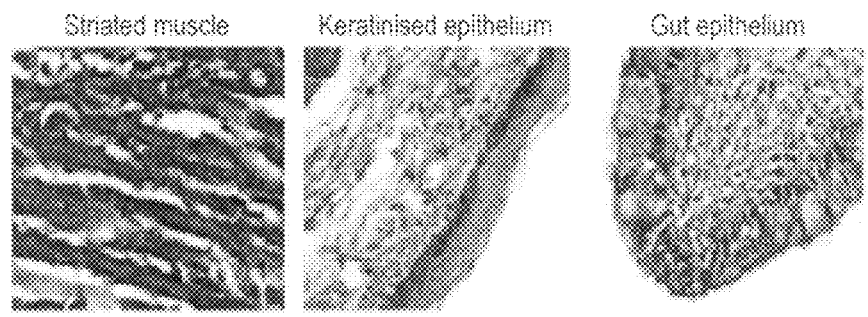
FIGS. 14A-14F show the formation of teratomas and contribution to chimaeras.

When cultured in suspension in serum-free medium without 3i cells died. However if serum or Matrigel were added, the cells aggregated into embryoid body-like structures (FIG. 13d). RT-PCR analysis of these structures revealed downregulation of Oct4 and Nanog, and appearance of endodermal and mesodermal markers (FIG. 13e). To characterize further the differentiation capacity of 3i rat cells we injected cells of both DA and Fischer derived lines under the kidney capsule of 11 immunocompromised SCID mice. After 30-55 days, animals were sacrificed. Seven exhibited a macroscopic tissue mass at the site of the injection varying in size from less than a gram to over 4 grams. Growths were obtained from both lines tested. Histological analysis of two specimens, one from each line, revealed classical features of a teratoma, with multiple differentiated cell types and structures including striated muscle, bone, cartilage, keratinised epithelia, secretory epithelia of the gut, and many others (FIG. 14a). We conclude that 3i rat cell lines are capable of producing teratomas and are competent for mature multilineage differentiation.

Figure 14B:
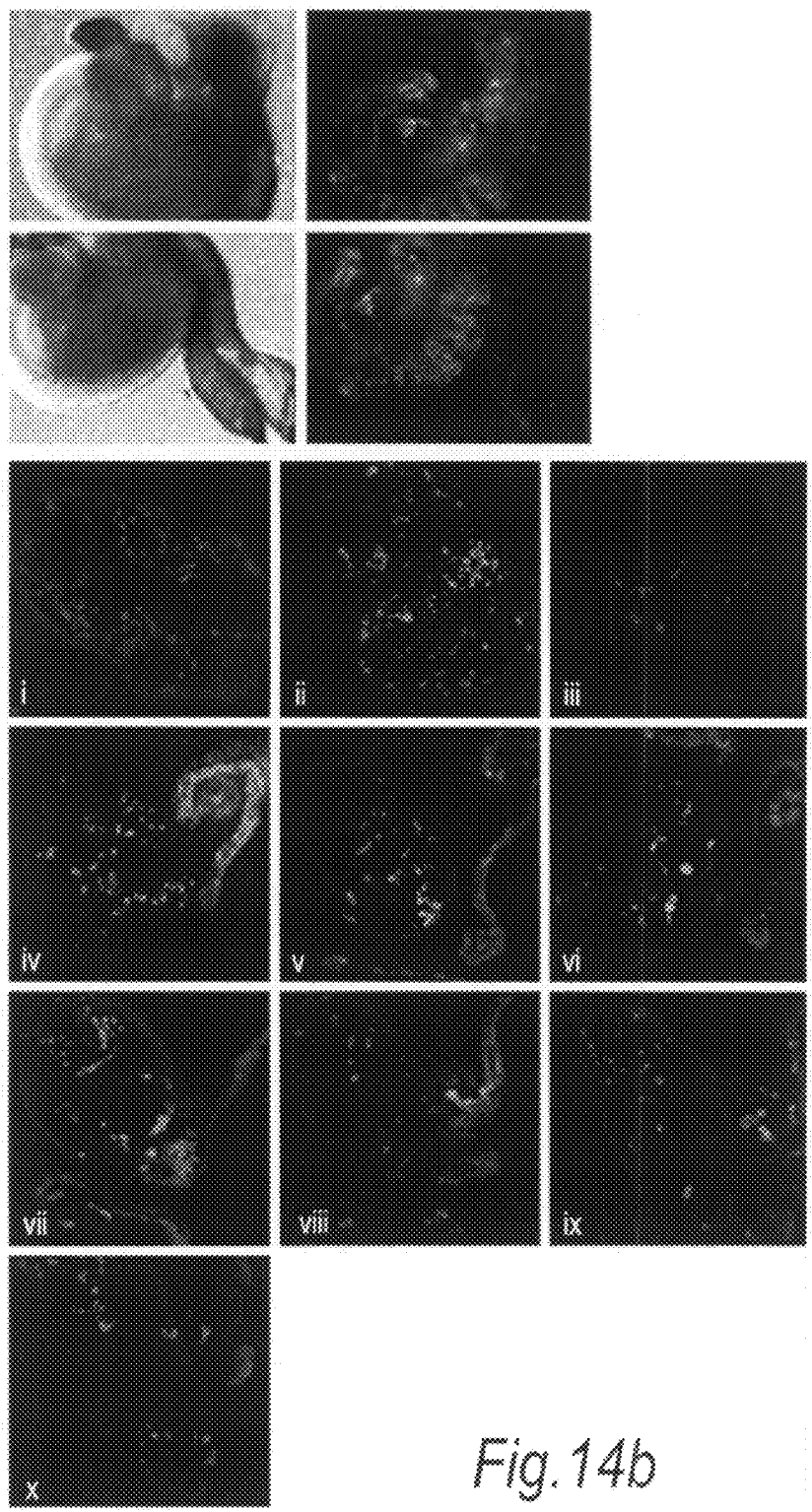
Figure 14C:
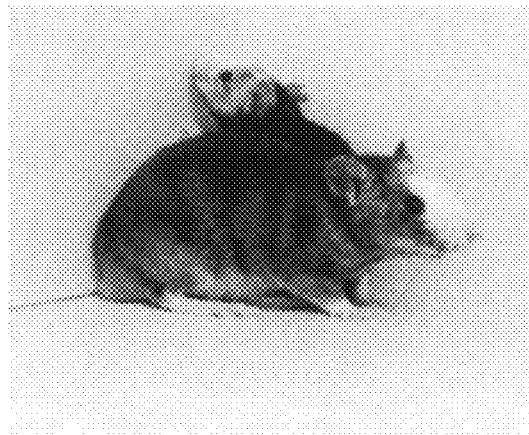

The defining feature of authentic ES cells is their capacity to colonise host embryos and contribute differentiated progeny to all three germlayers of chimaeric animals. Following lipofection and selection in puromycin we derived a pool of cells that express green fluorescent protein (GFP) constitutively from integrated plasmid. These cells were injected into blastocysts to track the contribution to developing embryos. Two out of eight embryos harvested at E10.5 showed widespread contribution of GFP labelled cells (FIG. 14b). Examination of cryosections confirmed incorporation into tissues of all three germ layers.

Figure 14D:
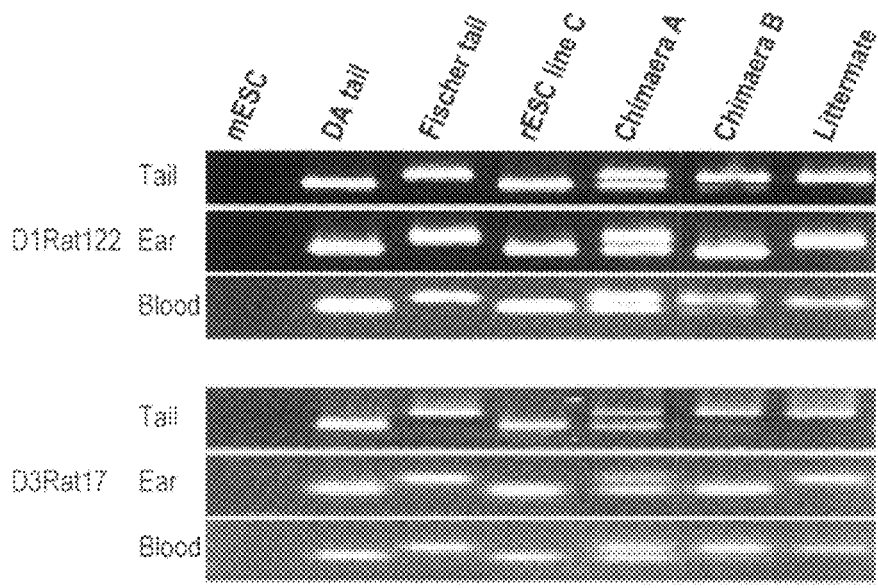
Figure 14E:
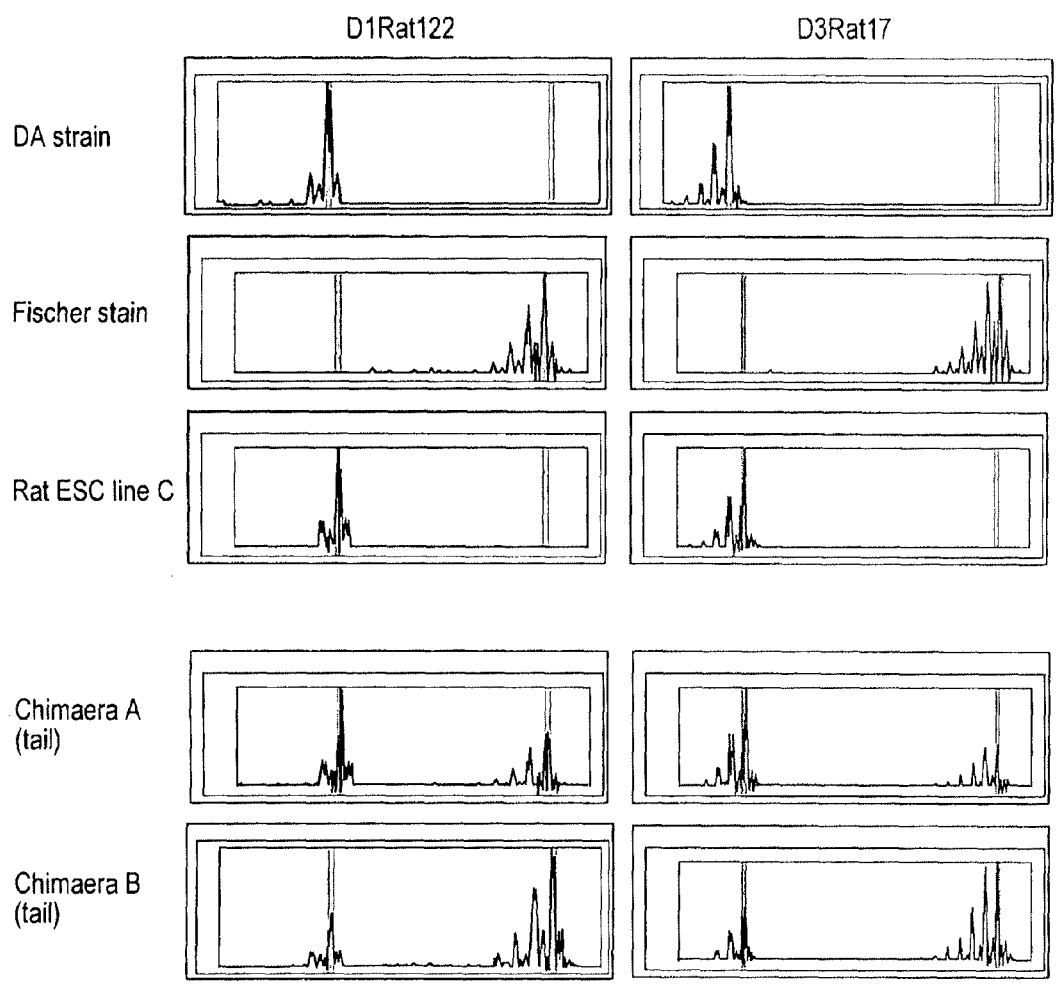
Figure 14F:
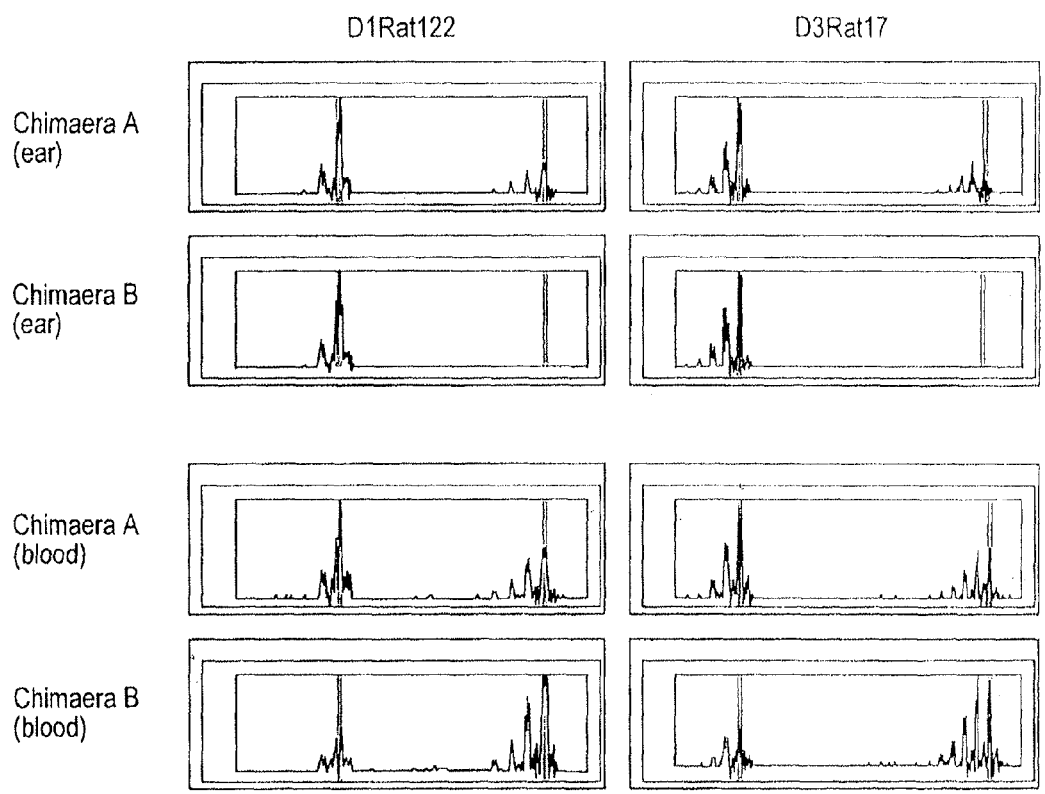

We also injected unmodified 3i rat cells into blastocysts to determine their potential to contribute to post-natal chimaeras. The genetically determined coat colour distinctions between agouti DA and albino Fischer provide a convenient indicator of chimaerism when cells of one strain are introduced into embryos of the other. Out of 15 pups generated from transferred embryos, 2 animals exhibited coat colouring diagnostic of the presence of introduced DA cells in Fischer hosts (FIG. 14b). These animals are heavily pigmented indicating a contribution of DA cells. The albino host contribution is apparent only on the head, a consequence of the presence of the hooded allele in the Fischers. This pattern is characteristic of rat chimaeras between albino hooded and fully pigmented strains[26]. To confirm and quantitate the chimaeric nature of these animals we undertook microsatellite analysis of tail biopsies. This revealed that cells from both contributing genotypes were present in proportions of 25:75 and 75:25 (DA:Fischer), respectively, in the two animals (FIG. 14d to 14f). These chimaeras have developed into healthy fertile adults. Both are male, however, and therefore will not support development of gametes from the introduced cells, retrospectively identified as XX.

Recently the derivation of cell lines from post-implantation egg cylinder stage epiblast has been reported in mice and rats[3, 10]. These so called EpiSCs have multilineage differentiation potential in vitro but exhibit a range of phenotypic, molecular and developmental differences from true ES cells. Most notably they show little or no ability to be reincorporated into the pre-implantation embryo and contribute to chimaeras. In contrast the 3i rat cells do contribute to chimaeras. They also express Rex1, Stella (Dppa3) and alkaline phosphatase, markers of ES cells and early epiblast that are absent in EpiSCs. Furthermore 3i rat cells can readily be propagated after dissociation into single cells whereas maintained cell-cell contact appears critical for EpiSCs. We tested whether the 3i rat cells could be maintained in the specific growth conditions, FGF2 plus activin, that are required to maintain EpiSCs. We found that they behaved like mouse ES cells and differentiated when 3i was replaced with activin plus FGF2, whether on feeders or fibronectin-coated dishes. In addition, the activin receptor inhibitor SB431452, which induces differentiation of EpiSCs[10] but not of mouse ES cells, did not impede propagation of undifferentiated 3i rat cells. A final difference between 3i cells and EpiSCs is that the latter are derived from post-implantation embryos rather than blastocysts. We also tested whether blastocyst-derived rat ExS cells[7] could be maintained in 3i and found that they do not survive. Therefore 3i rat cells are distinct from other cell lines established from cultured rat embryos.

Collectively these findings demonstrate that use of 3i enables the derivation of rat cell lines with cardinal features of ES cells: long-term self-renewal; pluripotency; and capacity for incorporation into the developing embryo. They also express the key molecular markers of the ES cell state, Nanog, Oct4, Sox2 and Rex1. The availability of rat ES cells opens the door to application of gene targeting and related genome engineering technologies in the species of choice for many areas of biomedical research. Availability of 3i rat cells immediately creates opportunities to use more advanced in vivo models for testing the capacity of in vitro stem cell differentiation to produce cells that can integrate and function in adult tissues. For example, evaluation of cognitive repair is considerably more sophisticated in rats than in mice.

The efficient preservation of pluripotency in cultured rat embryo cells using the neutralizing 3i culture system suggests that derivation of ES cells may indeed represent the capture of resident embryo cells rather than a tissue culture creation. Isolation of ES cells therefore may not entail extensive transcriptional or epigenetic reprogramming[5, 6, 27]. Rather ES cells may represent a simple continuation by default of early epiblast proliferation when inductive signals are eliminated (Ying et al, submitted). This raises the possibility that culture formulations based on the 3i principle may be sufficient for derivation of ES cells from other mammals, including livestock species.

Methods

Details of RT-PCR and microsatellite analyses, teratoma generation, and antibodies are provided in the supplementary information.

Immunosurgery. Zonae were removed from 4½ dpc rat blastocysts with acid Tyrodes, and the blastocysts incubated at 37° in 20% anti-rat whole serum (Sigma) for 3 hours. Blastocysts were washed and incubated for 20 minutes in rat serum as a source of complement, and the lysed trophectoderm removed by pipetting Culture procedure. Feeder cells were prepared from gamma-irradiated mouse fibroblasts[7] plated on gelatin in 4-well plates at a density of $1.5 \times 10^4$ cells per well. Isolated ICMs and passaged cell lines were plated on the feeders in N2B27 medium[28] containing Fgf receptor inhibitor SU5402, 2 µM, inhibitor of Mek1/2 activation PD184352, 0.8 µM, and the GSK3 inhibitor CHIR99021, 3 µM (3i; Ying et al., submitted). The 3i cell lines were routinely passaged by aspirating the colonies into fine pipettes and transferring the resultant disaggregated cells and small clumps to fresh plates. For embryoid body formation, samples of approximately 200 dissaggregated cells were transferred into 10 µl hanging drops. These were cultured for 2 days and cell aggregates collected and transferred into bacteriological dishes for a further 5 days.

Transfection protocol. Colonies were dissociated with Accutase (Sigma), pelleted in GMEM containing 10% FCS then resuspended in serum-free 3i culture medium and plated in a final volume of 400 µl. A mixture of 0.25 µg ScaI-linearised pPyCAGgfpIP plasmid[29] DNA, 0.25 µl PLUS reagent and 0.625 µl Lipofectamine LTX (Invitrogen Corporation) was added and cultures incubated overnight. The reagents were removed after 18 hours and replaced with fresh serum-free 3i culture medium. Stable transfectants were selected in 0.5 µg/ml puromycin applied 48 hours after transfection. Polyclonal lines were obtained by pooling several resistant colonies maintained continuously in puromycin.

Chimaera generation. 4.5 dpc rat embryos were collected by noon on the day of injection, and cultured for a further 2-3 hours in KSOM medium to allow maximum cavitation. Cell lines were disaggregated in Accutase and 10-12 cells injected into the blastocyst cavities of recipient embryos. Injected embryos were transferred into the uteri of 3.5 dpc pregnant rats. Due to unavailability of vasectomised male rats we were obliged to use naturally mated recipients for this study, which does reduce the frequency of implantation of transferred embryos.

Vibratome sectioning. Fluorescent embryos were embedded in a 1:1 mixture containing 20% gelatin and 20% albumin in PBS then fixed overnight at 4° C. in 4% paraformaldehyde. The gelatin blocks were then embedded in a 'setting solution' with 10% glutaraldehyde overnight at 4° C. Transverse sections were cut in a Series 1000 Vibratome at 100 µm and then treated with PBS/0.1% Tween20 for 10 minutes prior to mounting under coverslips in Vectashield (Vector Laboratories) containing DAPI nuclear fluorescent stain. Sections were examined by confocal microscopy within 24 hours.

Microsatellite genotyping. Fluorescent-tagged oligos were used to amplify the rat microsatellite regions D1Rat122 (forward oligo, 6-FAM-CTGCTCCACCTGCCTGTATT, reverse oligo, TCCCTTTGCAATAGACAATGG) and D3Rat17 (forward oligo VIC-TCATTTTCCTTC-CTCTCTCTCA, reverse oligo AAGACAAAATGCTG-GAGGGA) from genomic DNA of tail, ear and blood. PCR reactions were amplified on a PTC-200 thermocycler (MJ Research) using GoTaq Flexi DNA Polymerase (Promega Corporation, #M8305) under the following conditions; 95° C. 2 minutes, followed by 35 cycles of 94° C. 30 seconds, 56° C. or 62° C. 30 seconds and 72° C. 30 seconds, with a final extension at 72° C. for 5 minutes. The annealing temperature was 56° C. and 62° C. for D1Rat122 and D3Rat17 respectively. The PCR products were diluted 1 in 100 in sterile, distilled water. 1 µg of this was diluted in 9 µl Hi-Di Formamide (Applied Biosystems, #4311320) containing LIZ-500 internal size standard (Applied Biosystems, #4322682). The resulting products were detected on an ABI capillary 3730 DNA analyzer and visualised on a 4% agarose gel. The D1Rat122 alleles are 230 bp and 255 bp for DA and Fischer rat strains respectively. The D3Rat17 alleles are 140 bp and 178 bp for DA and Fischer strains respectively.

Teratoma generation. Approximately 200-400 cells were injected under kidney capsules of SCID mice (BALB/c JHan Hsd-Prkdc scid.). Tumours were collected at various times, and their weight determined by weighing tumour and kidney, and subtracting the weight of the contralateral uninjected kidney. Tumours were embedded in paraffin wax, sectioned, and stained with Masson's trichrome Antibodies. Plates upon which cells were growing were fixed in 4% PFA in PBS, permeabilised with PBST (0.3% Triton in PBS) and blocked in 1% BSA and 10% goat serum in PBST for 2 hours at room temperature. The primary antibodies were anti-oct-4 C10 (Santa Cruz Biotechnology, 1:200) anti-nanog (Abcam, 1:200) and anti-cdx2 (Abcam, 1:80), which were left on the plates overnight at 4° F. The secondaries were Alexa 488 IgG2b goat anti-mouse (for oct-4) Alexa 568 goat anti-rabbit IgG (for nanog) and Alexa 568 IgG1, goat anti mouse (for cdx2), all at a concentration of 1:1000, left on the plates for 2 hours at RT. Plates were counterstained with DAPI. Omission of the primary antibodies resulted in no fluorescence (nanog, cdx2) or a faint overall background (oct-4). For X chromosome immunostaining, cells were plated onto microscope slides (SuperFrost Plus, VWR international) and then incubated for approximately 3 hours. Cells were then fixed in 4% paraformaldehyde for 15 min at room temperature and permeabilized for 10 min in 0.5% Triton X. Antiserum against H3K27me3 (generous gift from Thomas Jenuwein) was used at 1:500.

RT-PCR. RNA was purified from around 50 colonies using RNeasy Mini Kit (Qiagen, #74104). cDNA was subsequently generated by Oligo-dT priming using SuperScript First-Strand Synthesis System (Invitrogen Corporation, #11904-

018). Typically one tenth of cDNA was PCR amplified on a PTC-200 thermocycler (MJ Research) using GoTaq Flexi DNA Polymerase (Promega Corporation, #M8305) under the following conditions; 94° C. 2 minutes, followed by 30 cycles of 94° C. 20 seconds, 50° C. 20 seconds and 72° C. 1 minute, with a final extension at 72° C. for 5 minutes. The primer sequences used and the product sizes are listed below.

| Rat mRNA | Rat primer sequence | Product size |
|---|---|---|
| β-Actin | For - CACTGGCATTGTGATGGACT<br>Rev - ACGGATGTCAACGTCACACT | 427 bp |
| Brachyury | For - AACTGCGAGTGGGTCTGGAAG<br>Rev - TGGGTCTCGGGAAAGCAGTG | 451 bp |
| Cdx2 | For - CCGAATACCACGCACACCATC<br>Rev - CTTTCCTTGGCTCTGCGGTTC | 394 bp |
| Eras | For - CGAGCGGTGTGGGTAAAAGTG<br>Rev - GGTGTCGGGTCTTCTTGCTTG | 501 bp |
| Errβ | For - TGTGCGGGACATTGCTTCTG<br>Rev - TCCCGATCTGCCAAGTCACAG | 436 bp |
| FGF4 | For - CGGGGTGTGGTGAGCATCTTC<br>Rev - CCTTCTTGGTCCGCCCGTTC | 202 bp |
| GATA-6 | For - TCATCACGACGGCTTGGACTG<br>Rev - GCCAGAGCACACCAAGAATCC | 467 bp |
| Kdr | For - ATACACCTGCACAGCGTACAG<br>Rev - TCCCGCATCTCTTTCACTCAC | 271 bp |
| Nanog | For - GCCCTGAGAAGAAAGAAGAG<br>Rev - CTGACTGCCCCATACTGGAA | 356 bp |
| Nestin | For - AGAGAAGCGCTGGAACAGAG<br>Rev - AGGTGTCTGCAACCGAGAGT | 234 bp |
| Oct-4 | For - GGGATGGCATACTGTGGAC<br>Rev - CTTCCTCCACCCACTTCTC | 412 bp |
| Pax6 | For - GAGACTGGCTCCATCAGACC<br>Rev - CTAGCCAGGTTGCGAAGAAC | 212 bp |
| Rex-1 | For - TTCTTGCCAGGTTCTGGAAGC<br>Rev - TTTCCCACACTCTGCACACAC | 277 bp |
| Sox2 | For - GGCGGCAACCAGAAGAACAG<br>Rev - GTTGCTCCAGCCGTTCATGTG | 414 bp |
| Sox17 | For - AGGAGAGGTGGTGGCGAGTAG<br>Rev - GTTGGGATGGTCCTGCATGTG | 268 bp |
| Stella | For - TCCTACAACCAGAAACACTAG<br>Rev - GTGCAGAGACATCTGAATGG | 304 bp |

| Mouse mRNA | Mouse primer sequence | Product size |
|---|---|---|
| Nanog | For - ATGAAGTGCAAGCGGTGGCAGAAA<br>Rev - CCTGGTGGAGTCACAGAGTAGTTC | 464 bp |

REFERENCES

1. Evans, M. J. & Kaufman, M. H. Establishment in culture of pluripotential cells from mouse embryos. Nature 292, 154-6. (1981).
2. Martin, G. R. Isolation of a pluripotent cell line from early mouse embryos cultured in medium conditioned by teratocarcinoma stem cells. Proc. Natl. Acad. Sci. USA 78, 7634-7638 (1981).
3. Tesar, P. J. et al. New cell lines from mouse epiblast share defining features with human embryonic stem cells. Nature (2007).
4. Gardner, R. L. & Brook, F. A. Reflections on the biology of embryonic stem cells. Int. J. Dev. Biol. 41, 235-243 (1997).
5. Zwaka, T. P. & Thomson, J. A. A germ cell origin of embryonic stem cells? Development 132, 227-33 (2005).
6. Buehr, M. & Smith, A. Genesis of embryonic stem cells. Phil. Trans. R. Soc., B 358, 1397-1402 (2003).
7. Buehr, M. et al. Rapid loss of Oct-4 and pluripotency in cultured rodent blastocysts and derivative cell lines. Biol Reprod 68, 222-9 (2003).
8. Nichols, J. et al. Formation of pluripotent stem cells in the mammalian embryo depends on the POU transcription factor Oct4. Cell 95, 379-91. (1998).
9. Mitsui, K. et al. The homeoprotein Nanog is required for maintenance of pluripotency in mouse epiblast and ES cells. Cell 113, 631-642 (2003).
10. Brons, I. G. et al. Derivation of pluripotent epiblast stem cells from mammalian embryos. Nature (2007).
11. Smith, A. in Stem Cell Biology (ed. Marshak, D. R., Gardner, R. L, Gottlieb, D.) 205-230 (Cold Spring Harbor Laboratory Press, New York, 2001).
12. Ying, Q. L., Nichols, J., Chambers, I. & Smith, A. BMP induction of Id proteins suppresses differentiation and sustains embryonic stem cell self-renewal in collaboration with STAT3. Cell 115, 281-92 (2003).
13. Prelle, K., Vassiliev, I. M., Vassilieva, S. G., Wolf, E. & Wobus, A. M. Establishment of pluripotent cell lines from vertebrate species—present status and future prospects. Cells Tissues Organs 165, 220-36 (1999).
14. Brenin, D. et al. Rat embryonic stem cells: a progress report. Transplant. Proc. 29, 1761-1765 (1997).
15. Vassilieva, S., Guan, K., Pich, U. & Wobus, A. M. Establishment of SSEA-1- and Oct-4-expressing rat embryonic stem-like cell lines and effects of cytokines of the IL-6 family on clonal growth. Exp Cell Res 258, 361-73. (2000).
16. Fandrich, F. et al. Preimplantation-stage stem cells induce long-term allogeneic graft acceptance without supplementary host conditioning. Nat Med 8, 171-8 (2002).
17. Niwa, H. How is pluripotency determined and maintained? Development 134, 635-46 (2007).
18. Nichols, J., Smith, A. & Buehr, M. Rat and mouse epiblasts differ in their capacity to generate extraembryonic endoderm. Reprod Fertil Dev 10, 517-25 (1998).
19. Niwa, H. et al. Interaction between Oct3/4 and Cdx2 determines trophectoderm differentiation. Cell 123, 917-929 (2005).
20. Matsuda, T. et al. STAT3 activation is sufficient to maintain an undifferentiated state of mouse embryonic stem cells. Embo J 18, 4261-4269 (1999).
21. Niwa, H., Burdon, T., Chambers, I. & Smith, A. Self-renewal of pluripotent embryonic stem cells is mediated via activation of STAT3. Genes Dev 12, 2048-60. (1998).
22. Okamoto, I., Otte, A. P., Allis, C. D., Reinberg, D. & Heard, E. Epigenetic dynamics of imprinted X inactivation during early mouse development. Science 303, 644-9 (2004).
23. Mak, W. et al. Reactivation of the paternal X chromosome in early mouse embryos. Science 303, 666-9 (2004).

24. Rastan, S. & Robertson, E. J. X-chromosome deletions in embryo-derived (EK) cell lines associated with lack of X-chromosome inactivation. J Embryol Exp Morphol 90, 379-88 (1985).
25. Silva, J. et al. Establishment of histone h3 methylation on the inactive X chromosome requires transient recruitment of Eed-Enx1 polycomb group complexes. Dev Cell 4, 481-95 (2003).
26. Yamamura, K. & Markert, C. L. The production of chimaeric rats and their use in the analysis of the hooded pigmentation pattern. Dev Genet 2, 131-146 (1981).
27. Smith, A. G. Embryo-derived stem cells: of mice and men. Ann. Rev. Cell Dev. Biol. 17, 435-462 (2001).
28. Ying, Q. L. & Smith, A. G. Defined conditions for neural commitment and differentiation. Methods Enzymol 365, 327-41 (2003).
29. Chambers, I. et al. Functional expression cloning of Nanog, a pluripotency sustaining factor in embryonic stem cells. Cell 113, 643-655 (2003).

Comparative Example 1

EP1726640, which names Teratani and Ochiya as inventors, purports to describe the provision of a rat embryonic stem cell. However, in the following experiments, the present applicant has shown that the culture conditions described by Teratani and Ochiya do not support the survival or proliferation of isolated rat ICMs and hence these conditions are not suitable for the derivation or maintenance of rat ES cells.

I. Culture of Established Rat ES Cells (Derived in 3i Conditions) According to the Teratani and Ochiya Protocol A. Medium was made up as specified in the Teratani and Ochiya protocol (that is: rLIF, KSR and other components as specified in EP1726640, in the concentrations specified, in DMEM)

B. Feeder layers were prepared from gamma-irradiated MEFs (primary cultures of mouse embryonic fibroblasts, passage 3)

C. Colonies from established rat ES cell lines (derived according to the procedures described in Example 4—lines oct-4 1 (passage 12), DA 2 (passage ~10) C (passage 22) and D (passage 20) were disaggregated and transferred to wells of a 4-well plate, in medium as in A and on feeders as in B. This was labelled plate 253. Cultures prepared from the same lines were maintained in parallel in 3i conditions D. Results Day 2. Lines oct-4 1 and DA 2: poor: rounded cells appearing on surface of colonies. Lines C and D: still look undifferentiated Day 6. All poor. Much cell death, much differentiation as cobble-like cells on bottom of the dish, also as detaching rounded cells. Cells do not appear to have proliferated. Medium changed Day 8. All cells differentiated or dead. Cultures consist of large lumps of opaque brown material, with many cells outgrowing on the bottom of the wells Control cultures (in 3i) appear undifferentiated, and have proliferated extensively C. Conclusions. All cells cultured in the conditions specified in the Teratani and Ochiya protocol died or differentiated within 8 days: this protocol, therefore, is incapable of maintaining rat ES cells in a viable, undifferentiated and proliferative state.

II. Attempted Derivation of Rat ES Cell Lines in the Conditions Specified in the Teratani and Ochiya Protocol A. Medium and feeder layers were as described in IA and B, above B. Rat blastocysts (4.5 dpc) were collected and subjected to immunosurgery.

C. 7 isolated inner cell masses (ICMs) were transferred to the medium specified in Teratani and Ochiya (rLIF, KSR, etc.) (plate 258 B)

D. As controls, 6 isolated ICMs were transferred to 3i medium (plate 258 A)

E. Several outgrowths could be seen in the control well (A) but none in the well with the Teratani and Ochiya conditions (B). The cultures were fixed.

F. After DAPI staining, 5/6 ICM outgrowths were identified in the 3i control group. Cells in all had proliferated extensively G. 1/7 outgrowths could be identified in the Teratani/Ochiya group. It was extremely small and identifiable as an outgrowth only after DAPI staining.

H. Conclusions. The Teratani and Ochiya protocol does not support the survival or proliferation of isolated rat ICMs. There is no evidence to support the assertion that rat ES cells can be derived by this method.

Example 5

Derivation and Characterization of Ovine Pluripotent Cells

The following example describes the provision of ovine embryonic stem (ES) cells that can not be obtained by conventional methods. The ovine ES cells have been established and produced by performing a procedure comprising the following steps (A)-(D), using a novel, serum-free culture system:

(A) dissociating an inner cell mass formed by the culture of ovine blastocysts, remaining in a state of cell aggregation, (B) culturing primary embryonic stem cells resulting from the culture of the dissociated inner cell mass until it can be transferred or passaged, (C) dissociating the primary embryonic stem cells, which have become capable of being transferred or passaged, remaining in a state of cell aggregation, followed by passaging and culturing the same, and (D) further transferring or passaging and culturing the cells to establish an embryonic stem cell line.

The methods for ovine ES cell establishment, the method for characterizing the established ovine ES cells and the method for subculturing ovine ES cells are as follows;

1. Ovine.

The methods are suitable for deriving ES cells from any strain of ovine. For example, ES cells can be derived from ovine strains such as Merino strain and the like.

2. Feeder Cells.

It is preferable to use feeder cells for the establishment and the subsequent culture and transfer of ovine ES cells. Feeder cells may be ones derived from any species, and are preferably normal fibroblasts rather than but not to the exclusion of established and/or immortalised lines of feeder cells (e.x., DIAMs (C3H10T1); Rathjen P D, Toth S, Willis A, Heath J K, Smith A G. Differentiation inhibiting activity is produced in matrix-associated and diffusible forms that are generated by alternative promoter usage. Cell 1990: 62:1105-1114), with or without genetic-based selection markers. Specifically, normal mouse embryonic fibroblasts can be mentioned, but not to the exclusion of new born or adult fibroblasts. More specifically, primary cultured cells of normal mouse embryonic fibroblasts between the 12th and 16th days of pregnancy can be used. As the normal fibroblasts, for example, normal fibroblasts of 129 sv fetal mouse at the 12.5th day are exemplified.

The feeder cells can be prepared by a conventional method or commercially available products (mouse fetal fibroblasts; ATCC) can also be utilized. It is preferable to use the feeder cells inactivated by the treatment with mitomycin C, gamma-irradiation and the like. It may also be preferable to pre-coat the intended culture vessel with a matrix such as, but not exclusively, gelatin, fibronectin, laminin and the like.

3. Culture Medium.

For the production, establishment and culture of the ovine ES cells, a substantially serum-free culture medium was used. The specific compositions of the culture media used are detailed below;

a) Culture medium for ovine ES cell establishment.

A culture medium used in the steps from blastocysts to inner cell mass formation is referred to as "culture medium for ovine ES cell establishment". An example of the composition is as described in Dattena M, et al (Dattena M, Mara L, Bin T A A, Cappai P. Lambing rate using vitrified blastocysts is improved by culture with BSA and hyaluronan. Mol Reprod Dev. January 2007; 74(1):42-7).

b) Culture medium for ovine ES cells.

A culture medium used in the culture after inner cell mass formation (including culture of established ovine ES cells) is referred to as "culture medium for ovine ES cells" or hereafter "N2B27+3i". A specific example of composition; 100 mL Dulbecco's modified Eagle medium/F12 with 5 mM L-alanyl-glutamine or 2 mM L-glutamine (Invitrogen/Gibco) (Table II), 1 mL of 100× N2 supplement (Table II; 25 µg/mL insulin, 16 µg/mL putrescine, 100 µg/mL transferrin, 30 nM sodium selenite, 6 ng/mL progesterone, 50 µg/mL bovine or human serum albumin, final concentrations) added to 100 mL (1:1 v/v) Neurobasal medium (Invitrogen/Gibco) (Table II), 2 mL 50× B27 supplement (Table II; 2 mg/L L-alanine, 3.7 mg/L L-glutamate, 441 mg/L 1-glutamine, 7.76 mg/L L-proline, 0.10 mg/L biotin, 0.34 mg/L vitamin B12, 0.02 mg/L corticosterone, 0.0063 mg/L progesterone, 0.1 mg/L vitamin A, 0.1 mg/L retinol acetate, 4 mg/L insulin, 0.002 mg/L triiodo-L-thryonine, 25 mg/L sodium pyruvate, 0.047 mg/L lipoic acid, 1 mg/L vitamin E, 1 mg/mL D,L-α-tocopherol acetate, 2.5 mg/L catalase, 1 mg/L reduced glutathione, 2.5 mg/L superoxide dismutase, 2 mg/L L-carnitine, 1 mg/L ethanolamine, 15 mg/L D(+)-galactose, 2600 mg/L HEPES, 16.1 mg/L putrescine, 0.016 mg/L sodium selenite, 0.194 mg/L zinc sulphate, 1 mg/L linoleic acid, 1 mg/L linolenic acid, 2500 mg/L bovine or human serum albumin, 5 mg/L transferring, final concentrations), 3 µM CHIR99021, 0.8 µM PD184352, 2 µM SU5402 [Antibiotic-Antimicrotics solution (optional)].

4. Culture Conditions.

The temperature of ovine ES cell culture in the production, establishment and culture of ovine ES cells was within the range of 35° C.-37.5° C., and is preferably 37° C. The culture was carried out in a humidified 5% $CO_2$ incubator used for typical cell culture.

5. Method for Ovine ES Cell Establishment.

A specific example of the method for ovine ES cell establishment is described as follows;

a) Oocyte (embryo in blastocyst stage) collection.

An ovine for oocyte collection was selected. Oocyte collection was carried out by a conventional method described in Dattena M, et al (Dattena M, Mara L, Bin T A A, Cappai P. Lambing rate using vitrified blastocysts is improved by culture with BSA and hyaluronan. Mol Reprod Dev. January 2007; 74(1):42-7), although it will be appreciated that other conventional methods of oocyte collection can also be used. Specifically, ovines were naturally crossed, the female ovine for oocyte sampling was sacrificed to excise a uterus after vaginal plug detection. This uterus was perfused with a suitable medium to recover fertilized oocytes (embryos). The development or maturation proceeded from fertilized oocytes (embryos) through moluras to blastocysts (embryos in blastocyst stage) and was confirmed by microscopic observations that the development has proceeded to blastocyst stage. Preferably, the development proceeds up to the late blastocyst stage and where the inner cell masses are present and visible.

b) Formation and isolation of inner cell masses.

The blastocysts obtained in the aforementioned 5a) were confirmed microscopically, and zona pellucidas were removed using, for example, Acidic Tyrode (pH 2.5), hyaluronidase, pronase. Then, feeder cells treated with mitomycin C were seeded onto 0.1% gelatine/PBS-coated culture dishes, 5-10 zona pellucida-removed ovine blastocysts were transferred to each of the dishes, and the culture was started using the aforementioned "N2B27+3i" culture medium for ovine ES cell establishment.

Between the 1st and 8th days of the culture, zona pellucida-removed ovine blastocysts (late stage) adhered to the feeder cells. On 5-10 days after adhesion, the inner cell mass from the blastocysts was mechanically dissociated using a tapered glass Pasteur pipette or the like. The inner cell mass fragments or aggregates of 5-20 cells were transferred to a like culture dishe(s) aforementioned containing the "N2B27+3i" culture medium for ovine ES cell establishment. At the time, the inner cell mass was not dissociated with a protease such as trypsin-EDTA and the like, but mechanically dissociated as described above.

c) Establishment of ovine ES cells.

In the 0.1% gelatin/PBS-coated culture dishes wherein the feeder cells were seeded, inner cell masses dissociated as described above were cultured in the "N2B27+3i" culture medium for ovine ES cells. Primary ES cell colonies appeared between the 4th and 10th days of the culture. The appearance of the primary ES cell colony was confirmed by microscopic observations and the ES cells observed are referred to as "primary ES cells". By continuing the culture for about 5-10 days thereafter, the primary ES cell colony became capable of being further transferred or passaged. The "state capable of being passaged" used herein means a state wherein the number of cells constituting the primary ES cell colony formed has reached approximately 200-600. While microscopically confirming that it has such morphology, the ES cell colony was separated using a tapered glass Pasteur pipette. This separated ES cell colony was transferred to a sterile intermediate culture vessel containing a culture medium for ovine ES cells, and dissociated enzymatically to single cells with a protease such as trypsin-EDTA, preferably in the presence of an apoptosis inhibitor (e.x., Y-27632; Watanabe K et al. A ROCK inhibitor permits survival of dissociated human embryonic stem cells. Nature May 27, 2007, or mechanically into cell aggregates consisting of about 5-20 cells. The dissociated ES cell colony was subjected to a primary culture (cells at passage 1) in a culture medium for ovine ES cells in a 0.1% gelatin/PBS-coated culture dish wherein the feeder cells were seeded. An ES cell colony appeared after about 2-4 days and became in a state capable of being passaged about 5-10 days after the beginning of the culture. The passage of the cells thereafter was performed as above.

6) Presentation of Ovine ES Cells.

The ovine ES cell is expected to be characterised some or all of the following properties (a)-(m), many of which have been experimentally confirmed:

(a) the ES cell colony presenting as compact, near homogenous, (b) expressing Oct3/4 gene, Sox2 gene, Stella gene, Rex1 gene, FGF4 gene and Nanog gene,
(c) positive for alkaline phosphatase activity,
(d) having an embryoid body forming ability,
(e) differentially expressing SSEA (Stage-Specific Embryonic Antigen)-1, -3 and -4,
(f) expressing TRA (Tumour Rejection Antigen)-1-60, -1-81,
(g) having the same number of chromosomes as does a normal ovine cell,
(h) capable of being subcultured and remaining in the undifferentiated state,
(i) having in vitro pluripotency state,
(j) having a potential to differentiate to cells of three embryonic germ lineages,
(k) having in vivo teratoma formation ability,
(l) having an ability to produce a chimaeric ovine and,
(m) ability to be ovine germ-line capable.

The present invention provides an ovine ES cell retaining all the properties of an ES cell shown in the aforementioned (a)-(m) for the first time. The aforementioned attributes (a)-(m) can be analyzed by the following methods that the established ovine ES cell retains the properties as an ES cell, that is the properties as an ES cell maintaining an undifferentiated state.

6.1) Morphology.

The ovine ES cells maintained a compact, near homogenous colony as visualised by microscopy. (FIGS. 15A-D)

6.2) Expression of Gene Markers for Undifferentiated State.

Figure 16:
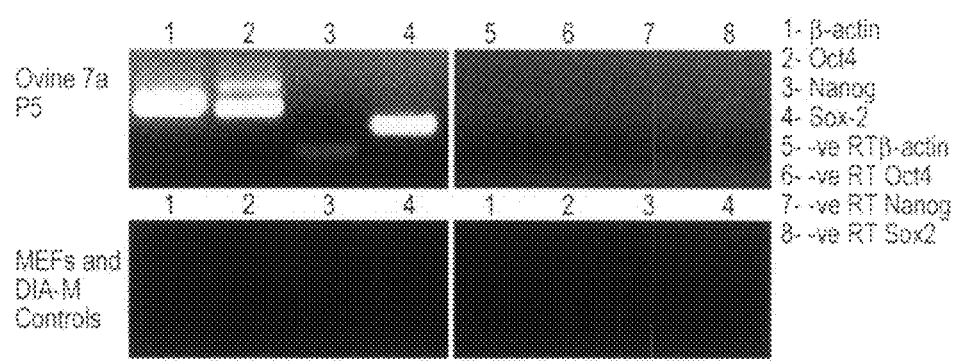
FIG. 16 shows RT-PCR data for a representative ovine ES cell line in the undifferentiated state (7a, passage 5).

The presence or absence of expression of representative undifferentiated state gene markers such as Oct3/4, Nanog, Stella, FGF4, Sox2 and Rex-1 are characteristic of ES cells. Ovine ES cells were analysed by reverse transcriptase polymerase chain reaction (RT-PCR) for the expression of the undifferentiated state gene markers (Table I). The housekeeping gene, β-Actin, was also used to assess the integrity of the cDNA. Commercial kits were used to extract mRNA from the samples and perform the synthesis of cDNA by RT-PCR (TRIzol reagent and SuperScript III First Strand Synthesis System for RT-PCR, Invitrogen) according to the manufacturer's instructions. Briefly, TRIzol extracted mRNA was converted to cDNA by SuperScript III reverse transcription in 20 µL RT reaction volume containing 4 µL 5× First Strand Buffer, 1 µL DTT (0.1M), 1 µL dNTP's (10 mM), 1 µL random primers (10 µM), 1 µL RNA inhibitor, 1 µL Superscript III and 7.5 µL H$_2$O and 3 µL mRNA sample. A corresponding RT negative, without Superscript III, was also prepared to determine genomic contamination. The reaction was then processed in a Thermal Cycler (Perkin Elmer) with the following cycle parameters: 50° C. for 60 mins and 70° C. for 15 mins. The cDNA was then used for PCR with primers of the undifferentiated state gene markers (Table I). A standard 25 µL PCR reaction volume was used containing 2.5 µL 10×PCR buffer, 1.5 µL MgCl$_2$ (25 mM), 0.5 µL dNTPs (10 mM), 1 µL Forward Primer (10 µM), 1 µL Reverse Primer (10 µM), 0.2 µL recombinant Taq DNA Polymerase, 17.3 µL H$_2$O and 1 µl RT sample. A reaction sample was then cycled using the following parameters: 94° C. for 5 mins, 35 cycles of (94° C. for 45 s, 55° C. for 45 sec and 72° C. for 45 sec), and 72° C. for 5 mins. Expression of Oct3/4, Nanog and Sox2 was visualised after a small volume of the final reaction aforementioned was electrophoresed on a 2.5% agarose gel, stained with ethidium bromide and photographed under UV illumination (FIG. 16).

6.3) Alkaline Phosphatase Activity.

Figure 15:
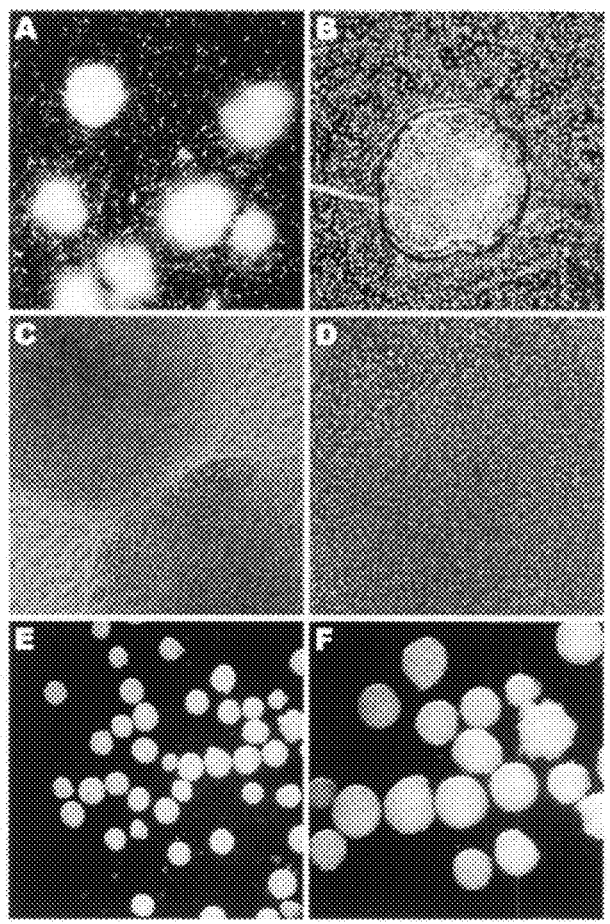
FIGS. 15A-F show the in vitro undifferentiated and differentiated states of a representative ovine ES cell line (7a, passage 5 or greater).

Undifferentiated ovine ES cell were observed to expresses an alkaline phosphatase in large amounts. The expression of the alkaline phosphatase can be easily determined using various commercially available alkaline phosphatase detection kits. In the present example the ALP tissue staining kit (Sigma) was used according to the manufacturer's instructions. (FIG. 15B).

6.4) Embryoid Body Forming Ability.

Embryoid body formation by culturing ES cell and/or aggregates using a non-coated culture dish under conditions without feeder cells. The embryoid body formation was confirmed by microscopic observations of the appearance of regular or irregular spheroid-like body formed by cell aggregation after ovine ES cells were cultured using a culture medium for ovine ES cells without 3 µM CHIR99021, 0.8 µM PD184352, 2 µM SU5402 ('3i') in a non-coated culture dish for about 2 days to 14 days. (FIGS. 15E and 15F).

6.5) Expression of Nuclear or Cell Surface Antigens.

One of the characteristics used in identifying the undifferentiated state of stem cells, including ES cell, is the detection of nuclear Oct3/4 and Nanog, and cell surface antigens (SSEA (stage-specific embryonic antigen)-1, -3, -4; TRA (Tumour Rejection Antigen)-1-60, -1-81) whose expression amounts change specifically as a consequence upon their differentiation. The expression of the cell surface markers was evaluated by an immunostaining using ES Cell Characterization Kits (Millipore) according to the manufacturer' instructions (data not shown).

6.5) Chromosome Number.

Normal, expected chromosome number for ovine diploid cells can be confirmed by analyzing the chromosome number by G-banding method (e.x., Sumner, A. T., Cancer Genet Cytogenet. 6: 59-87 (1982)) that the established ovine ES cell is a normal ES cell maintaining the chromosome number (2n=54) of ovine from which it originates.

6.6) Maintenance of Undifferentiated State.

The established ES cell can be subcultured with maintenance of undifferentiated state, characteristically that it can be subcultured until at least 30 passages. The maintenance of undifferentiated state can be confirmed by performing a subculture according to the subculture method of the ovine ES cell (the aforementioned 3), and determining the aforementioned (6) presentation of ovine ES cells.

6.7) Pluripotency.

ES cell spontaneously differentiates into various cells through an embryoid body by culturing it under conditions without feeder cells. This property of ES cell can be observed by forming an embryoid body by the method described in the aforementioned 6.4), then transferring the embryoid body to a gelatin-coated culture dish and culturing for about 7 days to 14 days. The appearance of neuron-like cell, adipose-like cell or epiderm-like cell or the like can be confirmed by the characteristic morphology of the each cell.

6.8) In vitro Differentiation by Culture in the Presence of Serum.

Moreover, the ES cell has a property that it differentiates by culture in the presence of 20% serum. Preferably, the ovine ES cell differentiates by culture in the presence of 2-20% serum. The differentiation of ovine ES cell in vitro can be confirmed by the disappearance of alkaline phosphatase activity, or disappearance of expression of ES cell undifferentiated state marker genes such as Oct3/4, Nanog and the like (aforementioned 6(a)-(f)).

6.9) Differentiation Potential to Cells of Three Embryonic Germ Lineages.

ES cells have a potential of differentiating to cells of three embryonic germ (endoderm, mesoderm, ectoderm) lineages. This property of ES cells can be confirmed by extracting RNA from an embryoid body (aforementioned 6.4), and analyzing the expression of each marker gene for ectodermal cell (e.g., neuron), mesodermal cell (e.g., cardiomyocyte) and endodermal cell (e.g., hepatocyte) by RT-PCR.

6.10) Ability of Teratoma Formation.

The transplantation of ES cells to a homologous or innate immunodeficient heterologous animal can lead to teratoma formation. The teratoma is the designation of a mixed tumor wherein various tissues derived from three embryonic germs, endoderm, mesoderm and ectoderm, are randomly present in a tumor. The formation of the teratoma can be confirmed by transplanting ovine ES cells to the subdermic and the like of a homologous animal or a heterologous animal with a primary immune deficiency, and macroscopically observing the presence of a bulbous growth after several months. It can be confirmed that the teratoma formed has three embryonic germ structures by sectioning the excised teratoma, staining with hematoxylin/eosin and observing the morphology of the tissues and cells microscopically.

6.11) Chimaeric Ovine-Producing Ability.

A chimaeric ovine can be produced by introducing ES cells into a homologous or heterologous ovine. The production of the chimaeric ovine can be carried out by, for example, the following method. To facilitate confirmation of the production of the chimaeric ovine, a marker gene (e.g., GFP, X-gal, luciferase, etc.) may be previously introduced into the ovine ES cell. Specifically, a recombinant ovine ES cell incorporating a vector containing such marker gene in the ES cell chromosome is established by incorporating the aforementioned vector into the ovine ES cell chromosome by an electroporation method and the like, followed by selection in a culture medium supplemented with a drug. The recombinant ovine ES cells are, for example, transplanted into a blastocoele of a ovine blastocyst or into morula stage or 16-cell stage embryo by a microscopic manipulation and developed with an inner cell mass or as a part of an inner cell mass (microinjection method: Gordon J. W. et al., Proc. Natl. Acad. Sci. USA., 77: 7380-7384 (1980)). Alternatively, zona pellucidas are removed from two 8-cell embryos and the embryos are co-cultured with the aforementioned recombinant ovine ES cells to form an aggregate. When the resulting aggregate is cultivated, one blastocyst is obtained (cell aggregate method: Dvorak P. et al., Int. J. Dev. Biol., 39: 645-652 (1995)). The embryo (egg for transplantation) obtained above is transplanted in the uterus of a pseudopregnant female ovine prepared by natural crossbreeding with a male ovine after vasoligation treatment and developed, whereby a chimaeric ovine can be produced.

That the obtained chimaeric ovine has cells and tissues derived from an ES cell, or an established rat ES cell has a chimaeric ovine-producing ability can be confirmed by, for example, genomic PCR using genomic DNA extracted from various tissues of chimaeric ovine as a template and marker gene (marker gene introduced into ES cell)-specific primers. Moreover, differentiation of ES cell to the cell of each tissue lineage can be confirmed, for example, by sectioning each tissue of a chimaeric ovine, and detecting the presence of a marker gene expression product (marker protein) based on the properties of the marker protein used.

TABLE I

Ovine Primer sequences.

| Gene | Forward Primer (5'-3') | Reverse Primer (5'-3') | Expected Product size (base pairs) |
|---|---|---|---|
| β-Actin | ggcacccagcacaa tgaaga | cgactgctgtcacc ttcaccg | 340 |
| Oct4 | agtgagaggcaacc tggagag | gacagacaccgagg gaaagac | 331 |
| Sox2 | catccacagcaaat gacagc | tttctgcaaagctc ctaccg | 251 |
| NANOG | agccccagagtgaa accactgtc | gtgttctcacagac ccagctg | 164 |

TABLE II

| | Type | | | |
|---|---|---|---|---|
| | DMEMF12 | Neurobasal | N2 | B27 |
| | | Concentration | | |
| | 1x | 1x | 1x | 1x |
| | Constituent concentration | | | |
| | mg/L | mg/L | mg/L | mg/L |
| INORGANIC SALTS, METALS | | | | |
| CaCl$_2$ (anhyd) | 116.6 | 200.0 | | |
| CuSO$_4$•5H$_2$O | 0.0013 | | | |
| Fe(NO$_3$)$_3$•9H$_2$O (Iron III) | 0.05 | 0.1 | | |
| FeSO$_4$•7H$_2$O | 0.417 | | | |
| KCl | 311.8 | 400 | | |
| MgCl$_2$ (anhydrous) | 28.64 | 77.3 | | |
| MgSO$_4$ (anhydrous) | 48.84 | | | |
| NaCl | 6995.5 | 3000 | | |
| NaHCO$_3$ | 2438 | 2200 | | |
| NaH$_2$PO$_4$•H$_2$O | 62.5 | 125 | | |
| Na$_2$HPO$_4$•H$_2$O | 71.02 | | | |
| ZnSO$_4$•7H$_2$O | 0.432 | | | |
| OTHER COMPONENTS | | | | |
| D-(+)-Galactose | | | | 15 |
| D-(+)-Glucose (Dextrose) | 3151 | 4500 | | |

TABLE II-continued

| | Type | | | |
|---|---|---|---|---|
| | DMEMF12 | Neurobasal | N2 | B27 |
| | | Concentration | | |
| | 1x | 1x | 1x | 1x |
| | | Constituent concentration | | |
| | mg/L | mg/L | mg/L | mg/L |
| Phenol Red | 8.1 | 8.1 | | |
| HEPES | | 2600 | | 2600 |
| Hypoxanthine•Na | 2.39 | | | |
| Linolenic acid | | | | 1 |
| Linoleic acid | 0.042 | | | 1 |
| Lipoic acid | 0.105 | | | 0.047 |
| Sodium Putrescine•2HCl | 0.081 | | 16.11 | 16.11 |
| Sodium Selenite (Na$_2$SeO$_3$•XH$_2$O) | | | 0.0052 | 0.016 |
| Sodium Pyruvate | 55 | | | 25 |
| AMINO ACIDS | | | | |
| L-Alanine | 4.45 | | | 2 |
| L-alanyl-L-glutamine | 542 | | | |
| L-Arginine•HCl | 147.5 | | | |
| L-Asparagine•H$_2$O | 7.5 | | | |
| L-Aspartic acid | 6.65 | | | |
| L-Cysteine•H$_2$O | 17.56 | | | |
| L-Cystine•2HCl | 31.29 | | | |
| L-Glutamic acid | 7.35 | | | 3.7 |
| L-Glutamine | | 441 | | |
| L-Glycine | 18.75 | | | |
| L-Histidine•HCl•H$_2$O | 31.48 | | | |
| L-Isoleucine | 54.47 | | | |
| L-Leucine | 59.05 | | | |
| L-Lysine•HCl | 91.25 | | | |
| L-Methionine | 17.24 | | | |
| L-Phenylalanine | 35.48 | | | |
| L-Proline | 17.25 | | | 7.76 |
| L-Serine | 26.25 | | | |
| L-Threonine | 53.45 | | | |
| L-Tryptophan | 9.02 | | | |
| L-Tyrosine•2Na•2H$_2$O | 55.79 | | | |
| L-Valine | 52.85 | | | |
| VITAMINS | | | | |
| D,L-a-tocopherol (Vit E) | | | | 1 |
| D,L-a-tocopherol acetate (Vit E) | | | | 1 |
| Biotin (Vit B27/H) | 0.0035 | | | 0.1 |
| L-Carnitine•HCl (Vit Bt) | | | | 2 |
| D-Ca panthenate (Vit B5) | 2.24 | 4 | | |
| Folic acid (Vit M) | 2.65 | 4 | | |
| (myo) i-Inositol (Vit Bh) | 12.6 | 7.2 | | |
| Niacinamide (Vit B3) | 2.02 | 4 | | |
| Pyridoxine•HCl (Vit B6) | 2.031 | 4 | | |
| all trans Retinol | | | | 0.1 |
| Retinyl acetate (Retinol, Vit A) | | | | 0.1 |
| Riboflavine (Vit B2) | 0.219 | 0.4 | | |
| Thiamine•HCl (Vit B1) | 2.17 | 4 | | |
| Thymidine (deoxy ribonucleoside) | 0.365 | | | |
| Vitamin B12 (Cobalamin) | 0.68 | 0.34 | | 0.34 |
| PROTEINS | | | | |
| Albumin (Bovine or Human serum) | | | 50 | 2500 |
| Cortisone | | | | 0.02 |
| Insulin (Full Chain) | | | 5, 25 | 4 |
| Transferrin | | | 100 | 5 |
| Progesterone | | | 0.0063 | 0.0063 |
| T3 (Triiodothyronine) | | | | 0.002 |
| OTHER | | | | |
| Catalase | | | | 2.5 |
| Choline chloride | 8.98 | 4 | | |
| Ethanolamine•HCl | | | | 1 |
| L-Glutathione (reduced) | | | | 1 |
| Superoxide dismutase (SOD) | | | | 2.5 |
| pH | 7.0-7.4 | ND | ND | ND |
| Osmolarity (mOsm/kg H$_2$O) | 290-330 | ND | ND | ND |

Example 6

Derivation and Characterisation of Bovine Pluripotent Cells

Aim

To assess the efficacy of 3i media to isolate bovine ES cells and to maintain bovine ES cell lines.

Materials and Methods

Experimental Design

To assess ES cells isolation, Day 7 or 8 blastocysts that were produced in vitro (n=105) were randomly allocated to each of four treatments:
1. Control (N2B27)
2. 3i medium (with hLIF)
3. 3i medium (without hLIF)
4. Millipore-Chemicon ESGRO Complete When the putative ES cells expanded they were passaged, and at this time samples were collected to characterize gene expression. After 30 days of culture, ES cell cultures and treatments were evaluated and treatments that did not yield ES cell lines were discontinued. ES cell lines were cultured for a further 60 days, for a total of 90 days. The proportion of blastocysts in each treatment that formed embryonal outgrowths, and were cultured to Passage 1, Passage 3 and Passage 6 was used to compare the treatments. Morphology and expression of pluripotency genes (i.e. oct4, rex1, sox2, ssea1, alkaline phosphatase, nanog) were also used to compare bovine ES cells in different treatments. All primers generate bands in cultured bovine ES cells except Nanog, which to date has only generated bands in blastocysts.

To assess maintenance of established bovine ES cell lines, established lines (n=3) were passaged to the same four treatments used in the ES cell isolation experiments, i.e. media 1-4 as described above. These established cell lines were cultured for up to 6 passages (~60 days). Morphology and expression of pluripotency genes (i.e. oct4, rex1, nanog, ssea1) were used to compare established bovine ES cell lines cultured in different treatments.

In Vitro Production of Embryos

Oocytes were collected one day a week to generate blastocysts in vitro for 4 consecutive weeks. Cumulus-oocyte-complexes (COCs) were aspirated from ovaries obtained from an abattoir, and bovine blastocysts were produced in vitro using previously described methods (1, 2). Briefly, COCs aspirated from ovaries were cultured for 24 hours in TCM-199 supplemented with β-estradiol, luteinising hormone and fetal bovine serum to trigger oocyte maturation. COCs with expanded cumulus were presumed to contain mature oocytes, and were co-cultured for 24 hours with bovine spermatozoa in IVF-TALP medium, containing heparin, penicillamine, epinephrine and hypotaurine. Putative zygotes were then cultured for 6-7 days in SOF medium (3) supplemented with essential and non-essential amino acids, tri-sodium citrate dehydrate, myo-inositol and bovine serum albumin. Gametes were cultured at 39° C. in a humidified gas environment of 5% $CO_2$ in air, and embryos were cultured at 39° C. in a humidified gas environment of 5% $CO_2$/5% $O_2$/90% $N_2$. From the total set of blastocysts, some blastocysts (n=15) were processed for characterization (positive control for RT-PCR) and the rest (n=105) were used for ES CELLS isolation.

ES Cell Isolation and Culture

Zonae pellucidae were mechanically removed from the blastocysts and the blastocyst was pressed onto a feeder layer of mouse embryonic fibroblasts (MEFs) that had been inactivated by mitomycin C treatment. Different batches of MEF feeders were used during the study, but each batch was used for all treatments. The pressed blastocysts on MEFs were cultured with a complex medium (α-MEM) supplemented with serum, non-essential amino acids and growth factors (human LIF, βFGF, EGF) at 39° C. in a humidified gas environment of 5% $CO_2$ in air. After 7-9 days the embryos formed embryonal outgrowths containing putative bovine ES CELLSs, which were mechanically cut from the primary culture (Passage 0) and pressed to fresh feeder layers (Passage 1). When the putative ES CELLSs had expanded (range: 6-26 days), they were passaged to fresh feeder layers. At the time of passage, samples of putative ES CELLSs were placed in lysis buffer (500 μl Lysis Buffer: 458.5 μl DEPC Water, 25 μl DTT (0.1 M), 4 μl IPEGAL and 12.5 μl RNA inhibitor) and stored at −80° C. for subsequent analysis of pluripotency gene transcripts. Culture media were changed every 2-3 days during culture. The nomenclature used to refer to the passage number of the cell lines isolated in this study was $P_x$, where x=the number of passages in this study.

Established bovine ES cell lines (BES-1: $P_{19}$, 183 days; BES-3: $P_{18}$, 206 days; BES-4: $P_{23}$, 210 days) were passaged to each of the four treatments. These established lines were cultured as described above. The nomenclature used to refer to the passage number of the established cell lines after they had been allocated to this study was $P_{x+y}$, where x=passage number before this study and y=the number of passages in this study.

RT-PCR Analysis of Gene Expression

Blastocysts (positive control) and putative bovine ES cells from recently isolated or established bovine ES cell lines were analysed by reverse transcriptase polymerase chain reaction (RT-PCR) for the expression of the pluripotency genes oct4, rex1, sox2, ssea1, alkaline phosphatase (AP) and nanog. The housekeeping gene, β-Actin, was used to assess the quality of cDNA. A commercial kit was used to extract mRNA from the samples (Dynabeads® mRNA DIRECT™ Micro Kit, Invitrogen). The standard protocol recommended by the manufacturer was used to extract the mRNA. Briefly, mRNA was converted to cDNA by Reverse Transcription. A 20 μl RT system was used: 4 μl 5*First Strand Buffer, 1 μl DTT (0.1 M), 1 μl dNTP Mixture (10 mM), 1 μl random primers (10 μM), 1 μl RNA inhibitor, 1 μl Superscript III and 7.5 μl $H_2O$ and 3 μl sample. A corresponding RT negative, without Superscript III, was prepared to check for genomic contamination. All reagents were purchased from Invitrogen. The prepared solution was processed in a Mycycler Thermal Cycler (Bio-rad) with the following program: 50° C. for 60 mins and 70° C. for 15 mins. cDNA quality was checked by PCR with β-Actin primers. Proved cDNA was then used for PCR with primers of the pluripotency markers. A standard 25 μl PCR system was used: 2.5 μl 10*PCR buffer, 1.5 μl $MgCl_2$ (25 mM), 0.5 μl dNTP Mixture (10 mM), 1 μl primer Forward (10 μM), 1 μL primer Reverse (10 μM) 0.2 μl Taq DNA Polymerase, recombinant, 17.3 μl $H_2O$ and 1 μl sample. All reagents were purchased from Fisher Biotec. The prepared solution was processed in a Mycycler Thermal Cycler (Bio-rad) with the following program: 94° C. for 5 mins, 35 cycles of (94° C. for 45 s, 55° C. for 45 s and 72° C. 45 s), and 72° C. for 5 mins.

The PCR products for OCT4 and Rex1 have been confirmed by sequencing. The PCR products for SSEA1, Sox2, Alkaline Phosphatase and Nanog have not yet been sequenced, but the size of the product is the same as that of the target genes.

The primers used for this study were as follows:

| Markers | Primer F | Primer R | Size |
|---|---|---|---|
| β-Actin | ggcacccagcacaatgaaga | cgactgctgtcaccttcaccg | 340 |
| Oct4 | agtgagaggcaacctggagag | gacagacaccgagggaaagac | 331 |
| Rex1 | gcagaatgtgggaaagcct | gactgaataaacttcttgc | 220 |
| SSEA1 | gagtcaatacgtgaccgtggac | ctgaagtagccgcgatagacag | 330 |
| SOX2 | catccacagcaaatgacagc | tttctgcaaagctcctaccg | 251 |
| NANOG | tgtgctcaatgacagatttcag | tagaagcctgggattctgc | 210 |
| AP | ggacccaggaaaccaaagtc | gaatgagggagtgagcaaacc | 378 |

Differentiation In Vitro

Explants excised from bovine ES cell colonies were placed in conditions to promote random differentiation (i.e. low-adhesion culture vessel, no feeder layer, no LIF, no growth factors), and cultured at 39° C. in a humidified gas environment of 5% $CO_2$ in air. Culture medium was changed every 3-4 days during culture.

Data Analysis

Continuous data (days in culture) are reported as arithmetic mean±standard error of the mean (S.E.M.). These data were limited and therefore not analysed statistically. Category data were analysed by a chi square analysis of contingency tables (4, 5). If the analysis returned a significant difference in the data set (i.e. $p \leq 0.05$), standardized residuals and percentage deviations were used to determine which observed chi square frequencies differed most from the expected frequencies, based on the null hypothesis (5). These differences are reported as positive or negative associations between the observation and the treatment.

Results
Growth in Culture
Isolation and Passage of Bovine ES Cells

Figure 3:
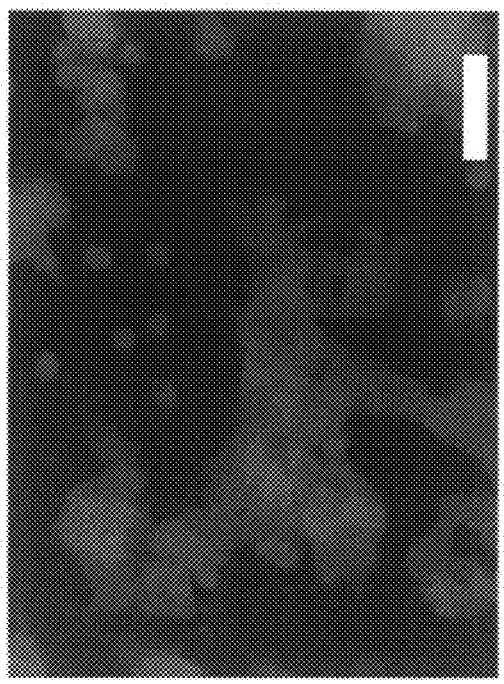
FIG. 3 shows that mouse ES cells grown in accordance with the invention, are Oct4 positive.
Figure 3:
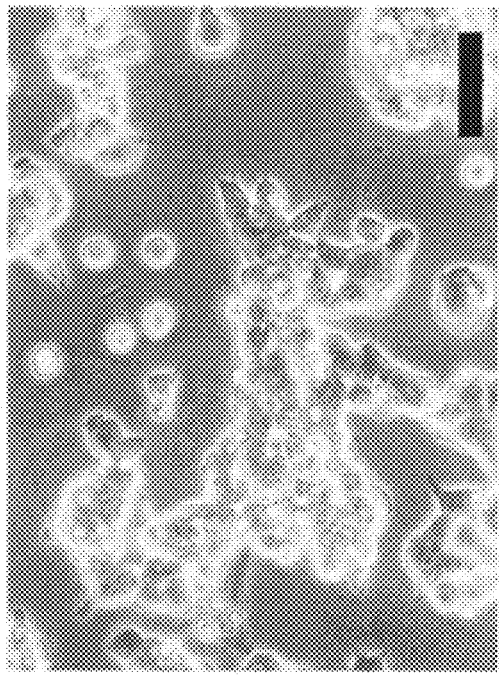
Figure 17:
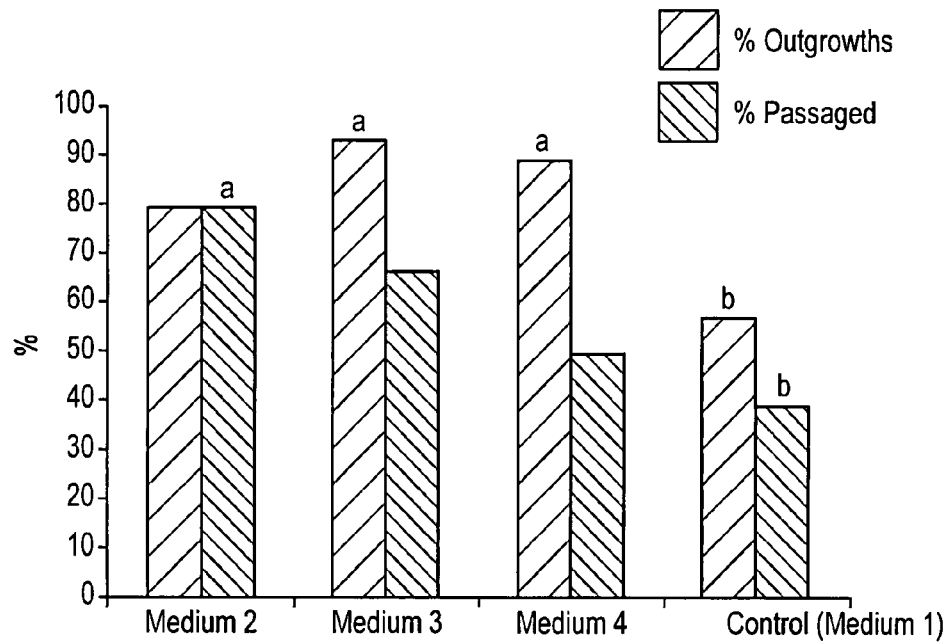
FIG. 17 shows a comparison of the percentage of bovine embryos that formed embryonal outgrowths and were taken to passage 1 among embryos cultured with media 1-4. % outgrowths: $\chi^2_3=12.49$, p=0.0059;% passaged $\chi^2_3=9.96$, p=0.0189. a There is a positive interaction between the observation (i.e. % outgrowths, % passaged) and the treatment. b There is a negative association between the observation and the treatment.
Figure 18:
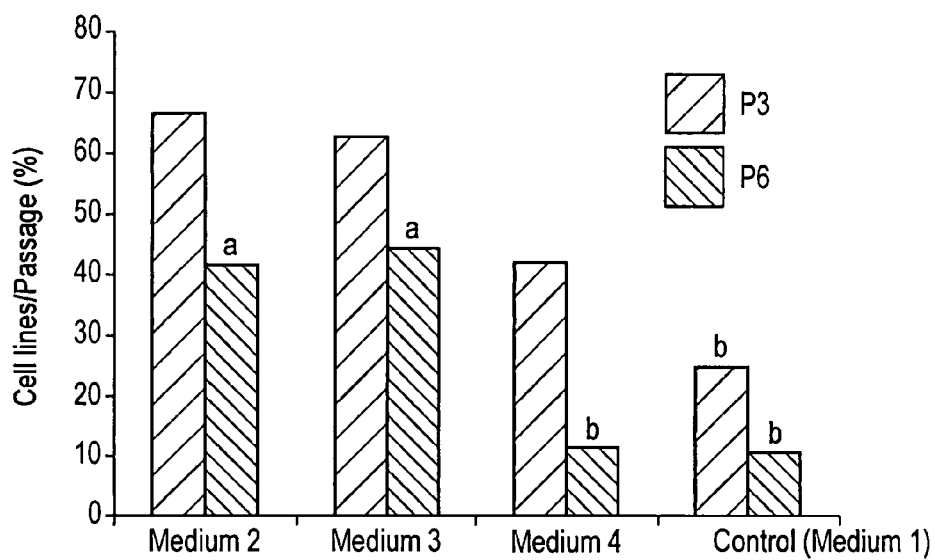
FIG. 18 shows a comparison of the percentage of embryos that formed embryonic stem cell lines by Passage 3 ($P_3$) or Passage 6 ($P_6$) among embryos cultured with media 1-4. $P_3$: $\chi^2_3=12.02$, p=0.0073; $P_6$: $\chi^2_3=13.81$, p=0.0032. a There is a positive association between the observation (i.e. % cell lines at $P_3$ or $P_6$) and the treatment. b There is a negative association between the observation and the treatment.
Figure 19:
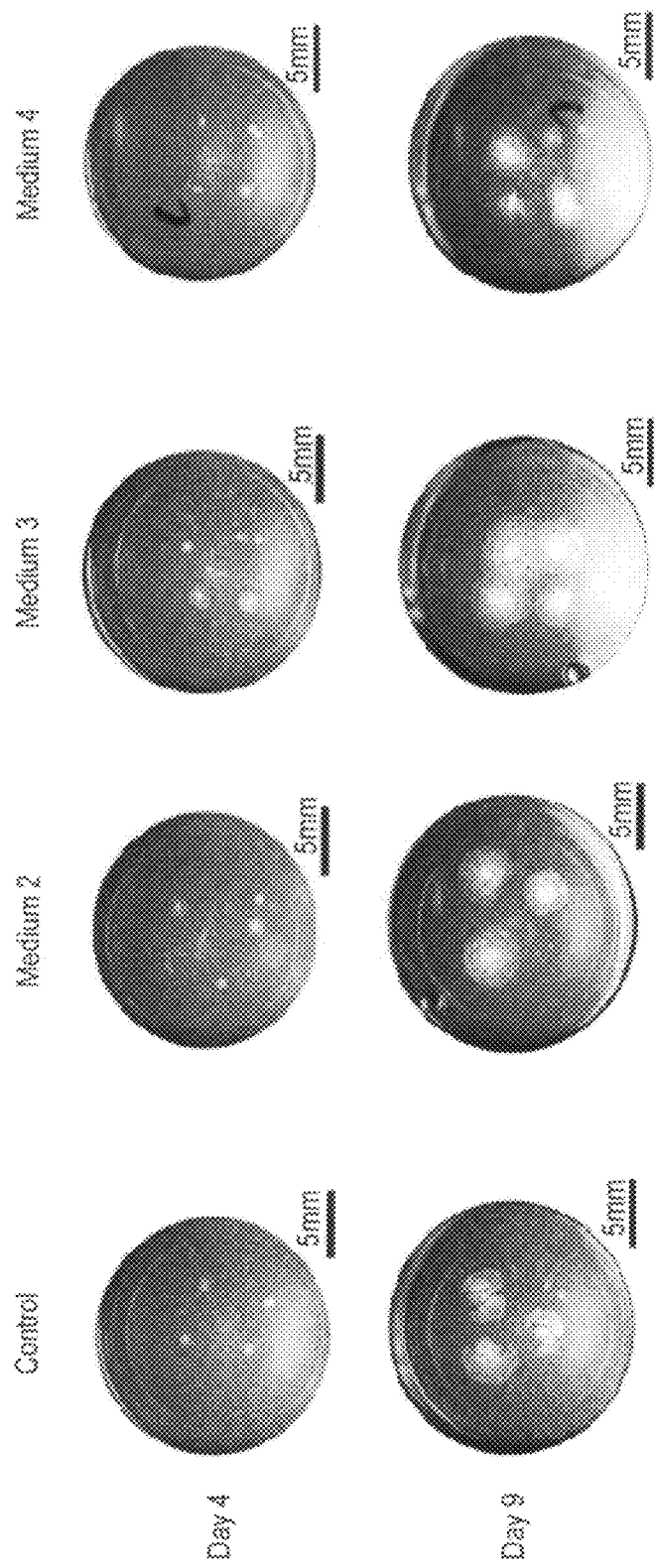
FIG. 19 shows a comparison of colony expansion at Passage 0 of bovine embryonic stem cell colonies from embryos cultured with media 1-4.

The proportion of embryos that formed embryonal outgrowths varied significantly between treatments ($\chi^2_3=12.49$, p=0.0059), and 80% or more of the embryos cultured with media 2-4 formed outgrowths (FIG. 17). There was a negative association between the % outgrowths and Control group, so that fewer embryos formed outgrowths when cultured with Control medium. The proportion of embryonal outgrowths that were passaged varied significantly between treatments ($\chi^2_3=9.96$, p=0.0189), with 65% or more of the blastocysts cultured with SCS1 or SCS2 being passaged (FIG. 17). There was a positive association between % Passaged and medium 2 (3i plus hLIF), and a negative association between % Passaged and Control group. The proportion of bovine ES cell lines at Passage 3 ($\chi^2_3=12.02$, p=0.0073) and Passage 6 ($\chi^2_3=13.81$, p=0.0032) varied significantly between treatments (FIG. 18). More than 60% of blastocysts cultured with media 2 and 3 (3i with or without hLIF) were passaged to Passage 3, and there was a negative association between the % Cell lines at P3 and Control group. More than 40% of blastocysts cultured with medium 2 or 3 were passaged to Passage 6, and there was a positive association between the % Cell lines at P6 and medium 2 and 3 groups and a negative association between the % Cell lines at P6 and medium 4 and Control groups. During isolation at Passage 0, ES cell colonies expanded at a similar rate when cultured with any of the four media (FIG. 3). After 50 days of culture, all cell lines isolated with medium 2 (52.8±0.56 days) or medium 3 (54.0±1.13 days) had progressed to P6 or later, while some cell lines isolated with Control (n=2) or medium 4 (n=3) had not yet been passaged to Passage 6 (i.e. still in Passage 5).

Culture of Established Bovine ES Cell Lines

Figure 20:
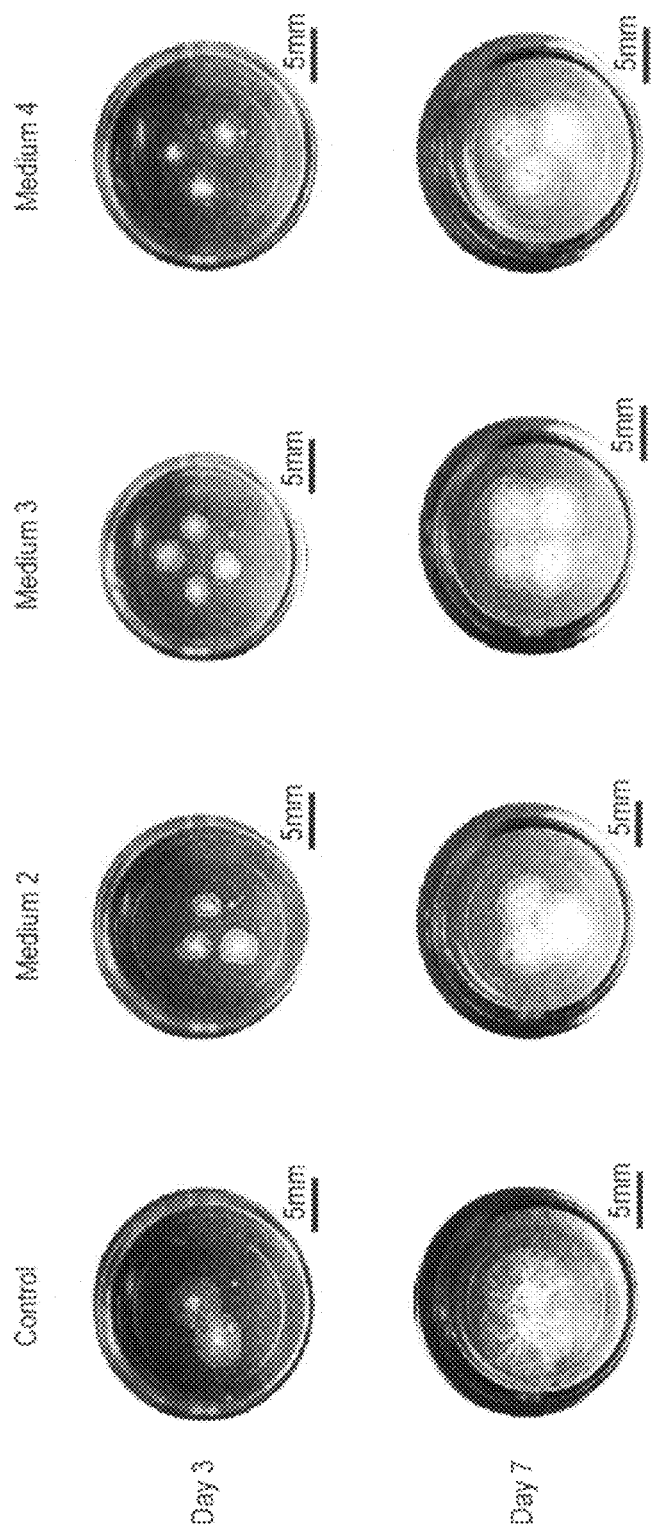
FIG. 20 shows a comparison of colony expansion during the first passage (i.e. $P_{23+1}$) of an established bovine ES cell line, BES-4, cultured with media 1-4.

Growth of one of the established bovine ES cell lines, BES-1, was retarded by MEF feeders that were not completely inactivated (see Results: General Morphology in Culture). This cell line was only cultured in the treatments for three passages and the data were not analysed, but explants from BES-1 were tested for their potential to differentiate in vitro after culture in the treatments (see below). The other two established bovine ES cell lines, BES-3 and BES-4, were cultured for 8 passages in each of the four media. There were no apparent differences among treatments or between cell lines in explant survival, number of passages supported, or the number of days to complete 8 passages (Table 3). During culture with each of media 1-4, ES cell colonies from established bovine ES cell lines expanded at a similar rate (FIG. 20).

TABLE 3

Comparison of explant survival, number of completed passages and days in culture to end of Passage 8 of established bovine ES cell lines, BES-3 and BES-4, cultured with media 1-4.

| | BES-3 | | | | BES-4 | | | |
|---|---|---|---|---|---|---|---|---|
| Medium | 1 | 2 | 3 | 4 | 1 | 2 | 3 | 4 |
| Explant Survival | 36/37 | 23/23 | 12/12 | 13/13 | 25/27 | 31/31 | 31/31 | 18/18 |
| Completed Passages | 8 | 8 | 8 | 8 | 8 | 8 | 8 | 8 |
| Days in Culture to Complete 8 Passages | 74 | 80 | 80 | 80 | 81 | 76 | 76 | 76 |

General Morphology in Culture

Figure 21:
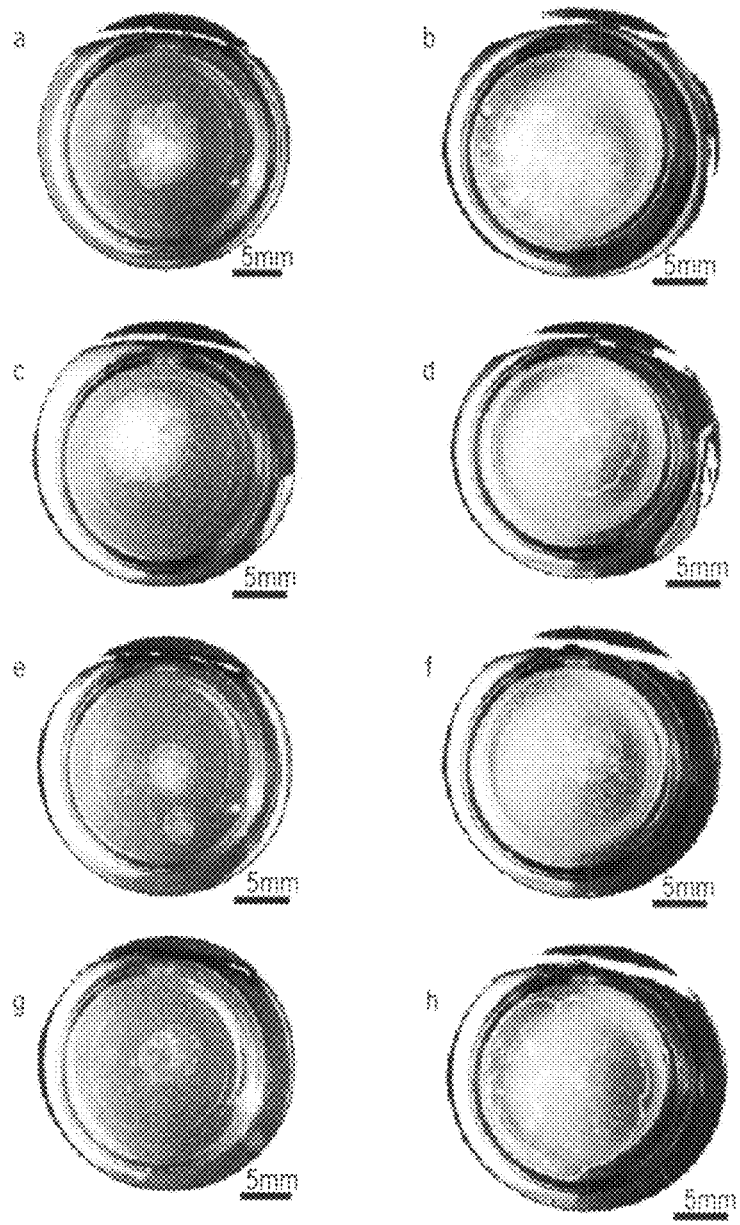
FIGS. 21A-21H show a comparison of the morphology of bovine embryonic stem cell colonies cultured with (a, b) control medium, (c, d) medium 2, (e, f) medium 3 of (g, h) medium 4 for (a, c, e, g) 37 days or (b, d, f, h) 57 days. Cultures were at passages 4, 5 or 6.
Figure 22:
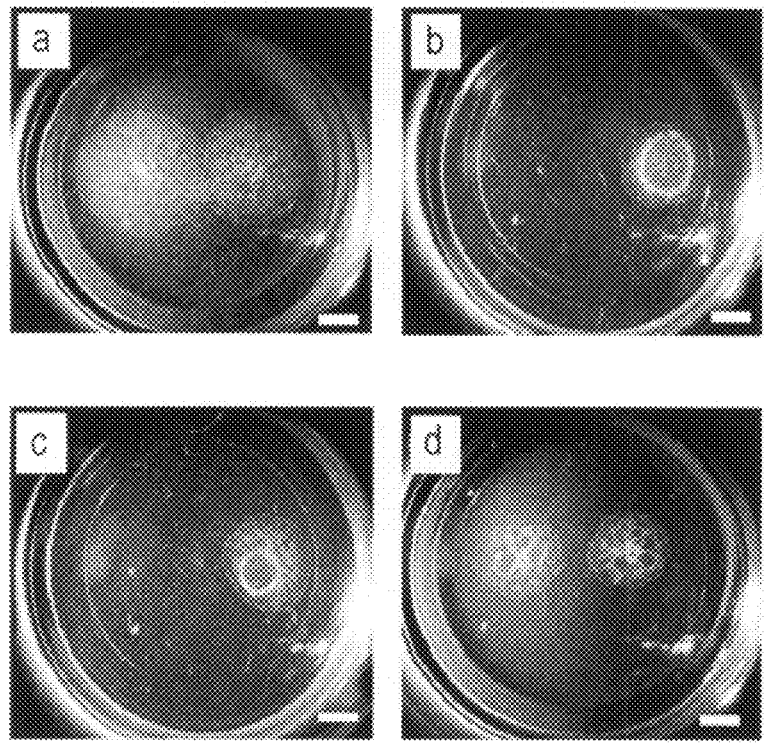
FIGS. 22A-22D show a comparison of the morphology of bovine embryonic stem cell colonies from an established bovine ES cell line, BES-1, cultured with (a) control medium, (b) medium 2, (c) medium 3 or (d) medium 4 for 10 days. Cultures were at $P_{19+1}$. Scale bar=2 mm.
Figure 23:
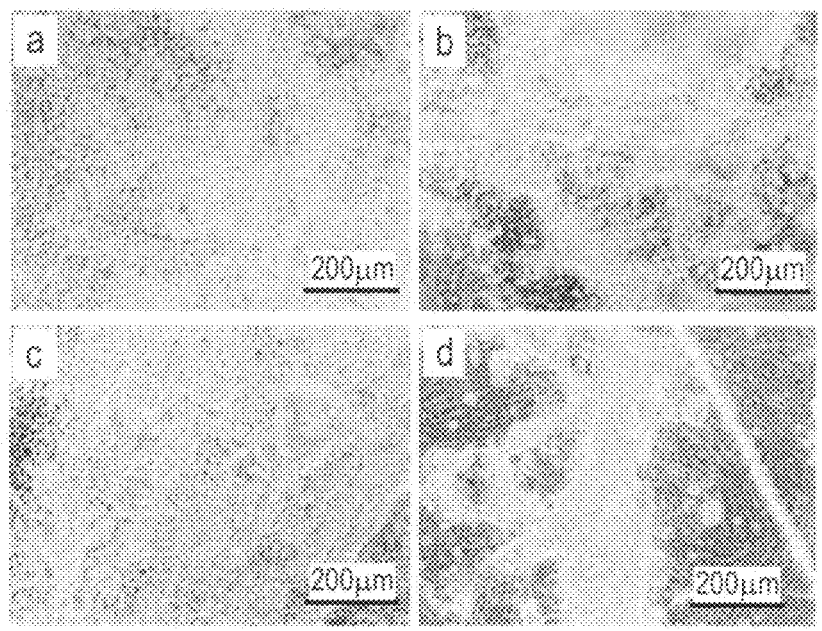
FIGS. 23A-23D show a comparison of the morphology of bovine embryonic stem cells from colonies isolated with (a) control medium, (b) medium 2, (c) medium 3 or (d) medium 4. Cultures were at $P_5$ or $P_7$.
Figure 24:
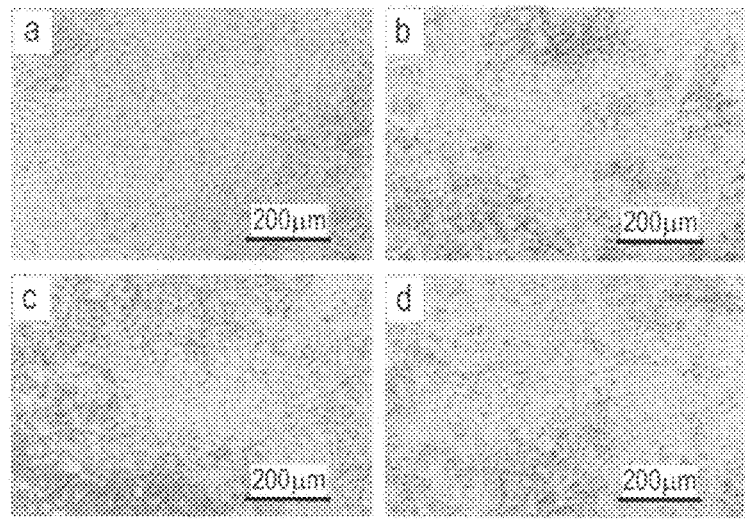
FIGS. 24A-24D show a comparison of the morphology of bovine embryonic stem cells from an established bovine ES cell line, BES-1, cultured with (a) control medium, (b) medium 2, (c) medium 3 or (d) medium 4. Cultures were at $P_{18+1}$.

There were no obvious differences in colony morphology between newly isolated bovine ES cells and those that formed from established cell lines. Bovine ES cell colonies cultured with Control medium were round to oval in shape, with an undulate border (FIGS. 21a, 21b, 22a). The colonies were mostly flat (i.e. two dimensional), with few vertical undulations. Putative stem cells were mostly concentrated toward the centre of the colony, and the outer region of the colony contained no apparent ES cells. In some regions, fluid accumulated between the ES cells and the feeder, lifting the ES cell layer to form dome and spherical structures. ES cell colonies cultured with medium 2 (3i plus hLIF) (FIGS. 21c, 21d, 22b) or medium 3 (3i without hLIF) (FIGS. 21e, 21f, 22c) were round to oval in shape, with a very distinct, undulate border. These colonies were more three dimensional in form than those cultured with Control medium, having a dense centre with many vertical undulations radiating from the centre. Fluid had accumulated under some colonies so that they were convex. Colonies had dense, raised linear structures radiating from the centre. Putative ES cells were concentrated at the base of these linear structures where they elevated from the colony. Less dense regions of putative ES cells were located away from these structures, mostly toward the centre of the colony and some were located near the colony edge. Spherical, fluid-filled structures, resembling embryoid bodies, had formed near the raised linear structures after more than 10 days culture. ES cell colonies cultured with medium 4 were irregular in shape with an undulate, distinct border, similar to colonies cultured with Control medium (FIGS. 21g, 21h, 22d). The colonies were three dimensional, with dense regions of cells forming a fibrous, undulating network throughout the colony that had no regular pattern. In some regions, fluid accumulated between the ES cells and the feeder, forming dome and spherical structures. Cells in the colony were diffuse and patchy, but the centre of the colony was more dense and raised. Individual cells were quite apparent and the putative ES cells were in patches throughout the colony, but not apparent near the colony edge. Although the different treatments triggered differences in colony morphology, they did not appear to promote differences in morphology of putative ES cells (FIGS. 23 and 24).

Some batches of MEF feeders cultured with Control medium had a typical morphology in that they formed a uniform layer on the culture vessel that remained relatively unchanged throughout the passage. When cultured with any of media 2-4, the cells of the feeder began to round up and detach from the feeder layer by Day 3 of the passage, but this response was more acute with medium 4. Other batches of MEF feeders did not behave in a typical manner when cultured with Control medium, in that cloudy regions appeared throughout the layer and the cells seemed to continue to grow. These MEF feeders peeled away from the culture vessel by about Day 12 of the passage. When cultured with medium 2 or 3, these batches of MEFs looked very healthy and had a morphology that was typical of feeders cultured with Control medium. When these MEF batches were cultured with medium 4, the cells of the feeder rounded up and detached from the feeder layer by Day 6-8 of the passage.

Appearance and Behaviour During Passage

Sheets of bovine ES cells (explants) were reasonably easy to excise mechanically using 29 G needles from colonies cultured with Control medium. There was little movement of the entire bovine ES cell colony during mechanical passage. When explants were excised, the ES cell colonies appeared to be a single layer of cells that grew over the top of the MEF feeder layer. Explants from ES cell colonies cultured with medium 2 or 3 were more difficult to excise because the ES cell colonies appeared to be more dense, spongy and pliable. Much of the colony moved when needles were used to cut through the sheet of cells. Explants cultured with medium 2 or 3 were generally more easy to attach to fresh MEF feeder plates at passage, than were explants from colonies cultured with Control medium. ES cell colonies cultured with medium 4 moved significantly during passage, similar to colonies cultured with medium 2 or medium 3. The putative bovine ES cells near the centre of colonies cultured in medium 4 medium were quite friable at passage and readily dispersed to smaller clumps making it difficult to excise explants for passage. Medium 4 explants were quite refractile in appearance.

Expression of Pluripotency Genes

Figure 25:
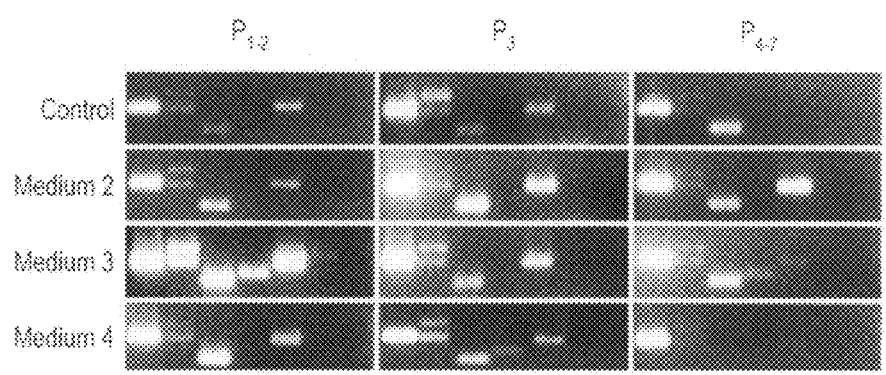
FIG. 25 shows a comparison of gene expression profiles of pluripotency during culture for ES cells from ES cell lines isolated in media 1-4. Control (medium 1) line at $P_1$, $P_3$, $P_7$; medium 2 line at $P_1$, $P_3$, $P_4$; medium 3 line at $P_2$, $P_3$, $P_6$; medium 4 line at $P_1$, $P_3$, $P_6$. Gene order for all gel figures, from Left to Right: β-actin, Oct4, Rex1, Sox2, SSEA1, Alkaline Phosphatase and Nanog.
Figure 26:
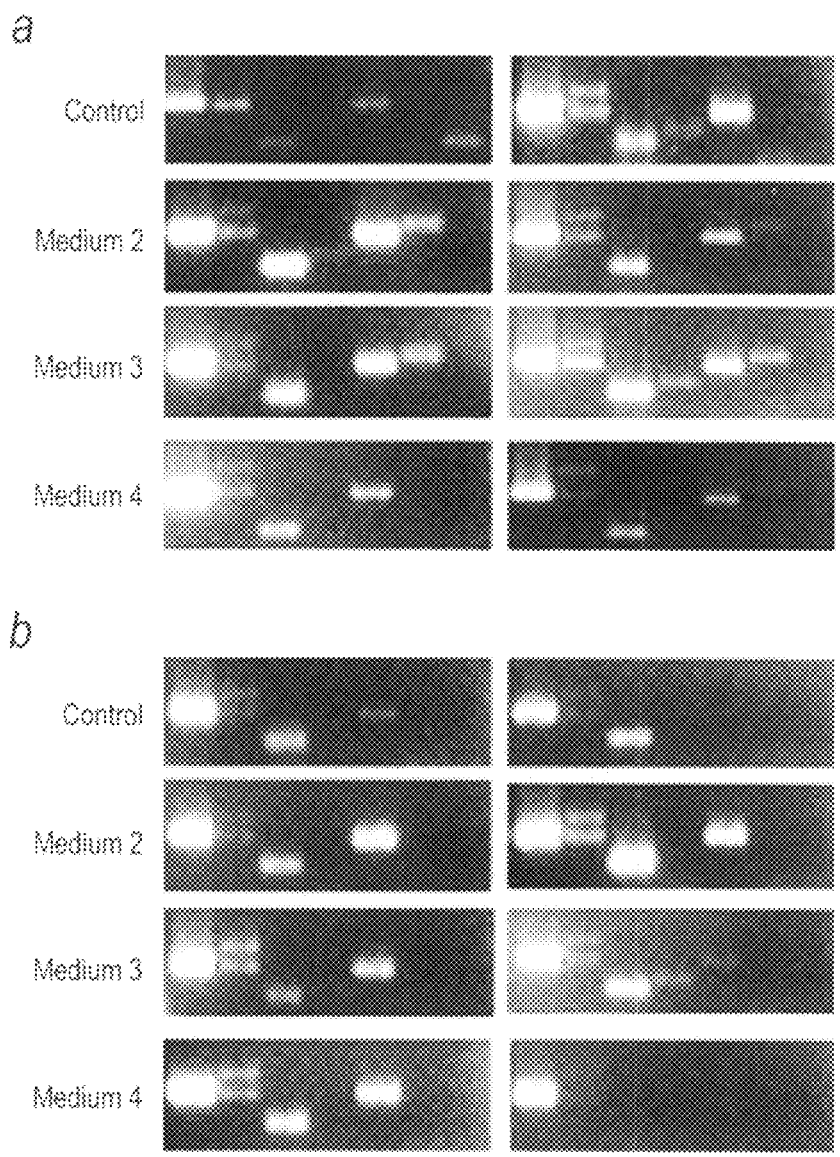
FIGS. 26A-26B show a comparison of the gene expression profiles of pluripotency for bovine ES cells from ES cell lines isolated in media 1-4, demonstrating some of the variation at (a) Passage 1 and (b) later passages, where control examples are from $P_4$ and $P_7$, medium 2 examples are from $P_4$ and $P_6$, medium 3 examples are from $P_5$ and $P_6$ and medium 4 examples are from $P_4$ and $P_6$. Gene order for all gel figures, from Left to Right: β-actin, Oct4, Rex1, Sox2, SSEA1, Alkaline Phosphatase and Nanog.

Oct4 was frequently and commonly expressed in bovine ES cells isolated in any of the four media, and other genes were never expressed without oct4 (FIGS. 25 and 26). Rex1 and ssea1 were also frequently expressed in bovine ES cells isolated in any of the four media, and were almost always expressed concurrently. Occasionally, rex1 was expressed without ssea1 (FIGS. 25 and 26: Control and medium 3: not shown), but ssea1 was never expressed without rex1. Sox2 and AP were less frequently expressed and always concurrently with oct4, rex1 and ssea1. Sox2 and AP were expressed in bovine ES cells isolated in any of the four media, but their expression was more common in earlier passages and in bovine ES cells isolated in 3i media (medium 2 or 3). Nanog was very rarely expressed and, on both occasions (FIG. 26: Control & medium 3), it was expressed concurrently with oct4, rex1 and ssea1. The only population of cells analysed that expressed all six pluripotency genes was bovine ES cells at Passage 1 isolated in medium 3 (3i without hLIF) (FIG. 26).

Figure 27:
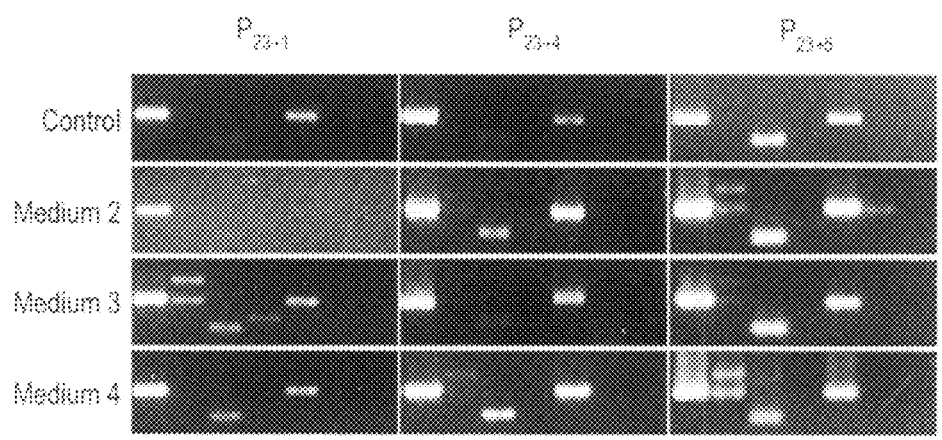
FIG. 27 shows a comparison of gene expression profiles of pluripotency for bovine ES cells from an established ES cell line, BES-4, cultured with media 1-4 for 1, 4 or 5 passages. Gene order for all gel figures, from Left to Right: β-actin, Oct4, Rex1, Sox2, SSEA1, Alkaline Phosphatase and Nanog.

The gene expression of bovine ES cells from established ES cell lines cultured with each of the four media differed in two aspects (FIG. 27). Firstly, rex1 and ssea1 were expressed in the absence of oct4, and secondly, the most commonly expressed genes were rex1 and ssea1, rather than oct4. More genes were expressed in established cell lines after a number of passages cultured with media 2-4, including oct4 when it had not been present at earlier passages.

Ability to Differentiate In Vitro

Figure 28:
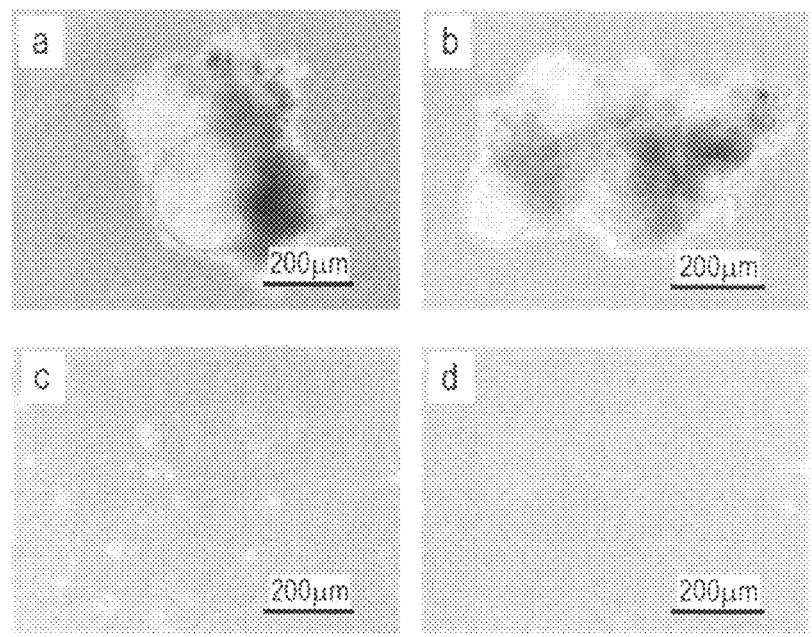
FIGS. 28A-28D show a comparison of the responses of explants from an established bovine ES cell line, when placed in conditions that promote in vitro differentiation. (a) Embryoid body formed from explants cultured with medium 2. (b) Embryoid body formed from explants cultured with medium 3. (c) and (d) Cells from explants cultured with medium 4 had attached to the culture vessel and begun to differentiate.

Within 3 days explants of one of the established lines (BES-1) excised from colonies cultured with medium 2 or 3 had formed fluid-filled, spherical structures and cell aggregates typical of embryoid bodies (EBs), when placed into conditions to promote in vitro differentiation (FIGS. 28a, 28b). These EBs were similar in form to those formed by explants excised from colonies cultured with Control medium. One explant in medium 2 had attached to the dish. Within 3 days, 2 explants excised from colonies cultured with medium 4 had attached to the dish. Individual cells had attached to the culture vessel and had begun to differentiate, in that they had numerous, long processes extending from a main cell body (FIGS. 28c, 28d). One explant had formed an aggregate of cells with attached vesicles. The EB cultures from BES-1 became contaminated with bacteria after 10 days culture and were discarded. Explants from colonies isolated in this study also formed EBs and attached colonies when placed into conditions to promote in vitro differentiation.

Discussion

Different media induced varied colony morphology, cell interactions and attachment to the feeder layer, as demonstrated by microscopic observation and behaviour at passage. During mechanical passage bovine ES cell colonies cultured with Control medium moved very little, suggesting that the bovine ES cells were attached to the feeder layer or to the culture vessel. Unlike human or mouse ES cell colonies, bovine ES cell colonies grow over the top of the feeder layer. The dense, spongy, pliable form of bovine ES cell colonies cultured with 3i media indicates these colonies may have been multilayered. During mechanical passage bovine ES cell colonies cultured with media 2-4 moved significantly, suggesting there was little connection to the MEFs or culture vessel. This is not surprising, since these three media had a detrimental effect on MEF feeder cells, causing them to round up and detach from the feeder. Individual cells in putative bovine ES cell regions were quite apparent in colonies cultured with medium 4, possibly indicating there were less connections between cells. While colony morphology varied greatly among media, differences in cell morphology were less apparent. Colony morphology and behaviour at passage was similar for newly isolated bovine ES cells and those that formed form established cell lines.

The 3i media (media 2 and 3) were more efficient for the isolation of bovine ES cells since more blastocysts formed embryonal outgrowths and were taken to Passage 1. These two media were also superior for bovine ES cell expansion and maintenance, since there were more cell lines at Passage 3 and Passage 6. All cell lines in 3i media (media 2 and 3) were at Passage 6 or later, while some cell lines cultured with medium 4 and Control medium remained viable at Passage 5 at the end of this study. This suggests bovine ES cell growth and development was faster in 3i media. In this study, Control medium was least efficient for the isolation and subsequent maintenance of bovine ES cells, since fewer embryos formed outgrowths and were passaged, and there were fewer cell lines at Passage 3 and Passage 6 (i.e. all parameters analysed).

There was a problem with some MEF feeder layers used in this study, in that they continued to grow and were probably not completely inactivated by the mitomycin C treatment. This may have selectively disadvantaged the control group as media 2-4 appeared to be detrimental to the MEF feeders and slowed the growth of any non-inactivated feeder cells, whereas Control medium had no effect on growth of the feeders. However, the same batches of MEF feeders were used in all four treatment groups in this study, so comparisons between treatments are valid. Differences in growth and development of established bovine ES cell lines were not apparent among the four media.

OCT4, Rex1 and SSEA1 are strong, robust pluripotency markers in bovine ES cells, and this was true for recently isolated ES cells and for established bovine ES cell lines. Oct4, Rex1 and ssea1 are usually expressed in bovine ES cells and, in this study, other pluripotency genes were never expressed in their absence. In newly isolated bovine ES cells the expression of rex1 and ssea1 was dependent on the expression of oct4, and the expression of ssea1 was dependent on the expression of rex1. The expression of these three genes was independent of treatment group. The expression of other pluripotency genes was irregular, sporadic and related to culture media, and culture with 3i media induced expression of other pluripotency genes. In established bovine ES cell lines, oct4 was often not expressed in early passages in this study, yet rex1 and ssea1 were expressed. Interestingly, oct4 was expressed in established ES cell lines after culture in media 2-4, even though it had not been detected in earlier passages. This suggests that the media induced expression of other pluripotency genes, which is similar to newly isolated ES cells. The OCT4 primers used in this study produce one clear band in blastocysts and in vivo embryos, but two bands in in vitro isolated ES cells. The smaller band has been sequenced and confirmed as OCT4, and the larger band is not genomic DNA, since the negative controls do not show the presence of this band. Our in vitro culture system may induce a pseudogene or isoform of oct4 to be expressed and to confirm this, the second band is being sequenced.

There were no significant differences in bovine ES cells cultured with medium 2 or 3 (3i medium), which varied only by the presence of hLIF in medium 2. This indicates that hLIF had little additional effect on the bovine ES cells.

Conclusions

Of the four media tested, the two 3i media were most efficient for the isolation of bovine ES cells. Growth and development of bovine ES cells and expression of pluripotency genes were superior in these two media. In addition, bovine ES cells isolated in 3i media showed potential to differentiate in vitro. Such pronounced differences in growth and development were not apparent with the established bovine ES cell lines. However more pluripotency genes were expressed after culture in 3i media, so these media appear to enhance the pluripotency component of bovine ES cell lines.

REFERENCES

1. Lonergan P, O'Kearney-Flynn M, Boland, M. P. (1999) Effect of protein supplementation and presence of an antioxidant on the development of bovine zygotes in synthetic oviduct fluid medium under high or low oxygen tension. Theriogenology 51: 1565-1576
2. Holm P, Booth P J, Schmidt M H, Greve T, Callesen H (1999) High bovine blastocyst development in a static in vitro production system using SOFaa medium supplemented with sodium citrate and myo-inositol with or without serum-proteins. Theriogenology 52: 683-700
3. Tervit H R, Whittingham, D G, Rowson L E A (1972) Successful culture in vitro of sheep and cattle ova. Journal of Reproduction and Fertility 30: 493-497
4. Zar J H (1999) Biostatistical Analysis. IE $4^{th}$ edn, Prentice Hall, Upper Saddle River
5. Fowler J, Cohen L, Jarvis P (1998) Practical Statistics for Field Biology. $2^{nd}$ Edn, John Wiley and Sons, New York

The invention claimed is:

1. A method of deriving a pluripotent rat cell from a blastocyst, comprising:
   (1) culturing a blastocyst in the presence of a MEK1 inhibitor at a concentration ranging from 0.1 μM to 5 μM, a GSK3 inhibitor at a concentration ranging from 0.1 μM to 20 μM, and LIF, to obtain an inner cell mass;
   (2) isolating and dissociating the primary outgrowths of the inner cell mass;
   (3) isolating a cell or cells from the dissociated primary outgrowths of the inner cell mass; and
   (4) culturing the isolated cell or cells in the presence of a MEK1 inhibitor at a concentration ranging from 0.1 μM to 5 μM, a GSK3 inhibitor at a concentration ranging from 0.1 μM to 20 μM, an antagonist of an FGF receptor at a concentration ranging from 0.5 μM to 10 μM, and LIF.

2. The method of claim 1, comprising culturing the blastocyst in the presence of the MEK inhibitor, the GSK3 inhibitor, LIF, and an antagonist of an FGF receptor.

3. The method of claim 1, wherein the pluripotent cell expresses one or more of Nanog, Oct4, FGF4, Sox-2 and alkaline phosphatase.

4. The method of claim 1, wherein the pluripotent cell expresses any two or more of Nanog, Oct4, FGF4, Sox-2 and alkaline phosphatase.

5. The method of claim 1, wherein the pluripotent cell expresses Nanog, Oct4 and Sox-2.

6. The method of claim 5, wherein the pluripotent cell further expresses alkaline phosphatase.

7. The method of claim 1, wherein the pluripotent cell expresses Rex 1, Stella, FGF4 and Sox-2.

8. The method of claim 1, wherein the pluripotent cell does not express FGF5.

9. The method of claim 1, wherein the pluripotent cell is morphologically undifferentiated in culture.

10. The method of claim 1, wherein the pluripotent cell is capable of being maintained in culture for at least two weeks.

11. The method of claim 10, wherein the progeny of the pluripotent cell retain the characteristics of the original pluripotent cell after being maintained in culture.

12. The method of claim 1, wherein the pluripotent cell is capable of contributing to a chimera.

13. The method of claim 12, wherein all cells of the chimera are cells of the same species as the pluripotent cell.

14. The method of claim 12, wherein the pluripotent cell is capable of contributing to the germ line of a chimera.

15. The method of claim 1, wherein the pluripotent cell is capable of forming a teratoma or teratocarcinoma in which differentiated cells from all three germ layers are present.

16. The method of claim 1, wherein the pluripotent cell is capable of growth and/or proliferation as a single cell in culture.

17. The method of claim 1, wherein the pluripotent cell is induced to differentiate or fails to grow in the presence of activin and/or FGF.

18. The method of claim 1, wherein differentiation of the pluripotent cell is not induced by activin receptor blockade.

19. The method of claim 1, wherein growth or proliferation of the pluripotent cell is supported by the presence of a MEK1 inhibitor at a concentration ranging from 0.1 µM to 5 µM, a GSK3 inhibitor at a concentration ranging from 0.1 µM to 20 µM and an antagonist of an FGF receptor at a concentration ranging from 0.5 µM to 10 µM.

20. The method of claim 1, wherein the pluripotent cell is an ES cell.

21. The method of claim 1, wherein the GSK3 inhibitor is a GSK3β inhibitor.

22. The method of claim 1, wherein the antagonist of an FGF receptor is an antagonist of FGFR1.

23. The method of claim 1, wherein the MEK1 inhibitor is present at a concentration ranging from 0.2 µM to 2 µM.

24. The method of claim 1, wherein the GSK3 inhibitor is present at a concentration ranging from 0.3 µM to 10 µM.

25. The method of claim 1, wherein the antagonist of an FGF receptor is present at a concentration ranging from 1 µM to 5 µM.

26. The method of claim 1, wherein the MEK1 inhibitor is selected from the group consisting of PD184362, PD98059, U0126, and SL327.

27. The method of claim 1, wherein the GSK3 inhibitor is selected from the group consisting of CHIR98014, CHIR99021, AR-AO144-18, TDZ-8, SB216763, and SB415286.

28. The method of claim 1, wherein the antagonist of an FGF receptor is selected from the group consisting of SU5402, and PD173074.

29. The method of claim 1, wherein the MEK1 inhibitor is PD184632, the GSK3 inhibitor is CHIR99021 and the antagonist of an FGF receptor is SU5402.

30. The method of claim 19, wherein the GSK3 inhibitor is a GSK3β inhibitor.

31. The method of claim 19, wherein the antagonist of an FGF receptor is an antagonist of FGFR1.

32. The method of claim 19, wherein the MEK1 inhibitor is present at a concentration ranging from 0.2 µM to 2 µM.

33. The method of claim 19, wherein the GSK3 inhibitor is present at a concentration ranging from 0.3 µM to 10 µM.

34. The method of claim 19, wherein the antagonist of an FGF receptor is present at a concentration ranging from 1 µM to 5 µM.

35. The method of claim 19, wherein the MEK1 inhibitor is selected from the group consisting of PD184362, PD98059, U0126, and SL327.

36. The method of claim 19, wherein the GSK3 inhibitor is selected from the group consisting of CHIR98014, CHIR99021, AR-AO144-18, TDZ-8, SB216763, and SB415286.

37. The method of claim 19, wherein the antagonist of an FGF receptor is selected from the group consisting of SU5402, and PD173074.

38. The method of claim 19, wherein the MEK1 inhibitor is PD184632, the GSK3 inhibitor is CHIR99021 and the antagonist of an FGF receptor is SU5402.

39. A method of deriving a pluripotent rat cell from a blastocyst, comprising:
   (1) culturing the blastocyst in the presence of PD184352 at a concentration of 0.8 µM, CHIR99021 at a concentration of 3 µM, and LIF in N2B27 medium, to obtain an inner cell mass;
   (2) isolating and dissociating the primary outgrowths of the inner cell mass;
   (3) isolating a cell or cells from the dissociated primary outgrowths of the inner cell mass; and
   (4) culturing the isolated cell or cells in the presence of PD184352 at a concentration of 0.8 µM, CHIR99021 at a concentration of 3 µM, SU5402 at a concentration of 2 µM, and LIF in N2B27 medium.

* * * * *

SEQUENCE LISTING

```
<160> NUMBER OF SEQ ID NOS: 60

<210> SEQ ID NO 1
<211> LENGTH: 20
<212> TYPE: DNA
<213> ORGANISM: Artificial
<220> FEATURE:
<223> OTHER INFORMATION: synthetic oligonucleotide

<400> SEQUENCE: 1
ctgctccacc tgcctgtatt                                            20

<210> SEQ ID NO 2
<211> LENGTH: 21
<212> TYPE: DNA
<213> ORGANISM: Artificial
<220> FEATURE:
<223> OTHER INFORMATION: synthetic oligonucleotide

<400> SEQUENCE: 2
tccctttgca atagacaatg g                                          21

<210> SEQ ID NO 3
```

```
<211> LENGTH: 22
<212> TYPE: DNA
<213> ORGANISM: Artificial
<220> FEATURE:
<223> OTHER INFORMATION: synthetic oligonucleotide

<400> SEQUENCE: 3 tcatttttcct tcctctctct ca                                            22

<210> SEQ ID NO 4
<211> LENGTH: 20
<212> TYPE: DNA
<213> ORGANISM: Artificial
<220> FEATURE:
<223> OTHER INFORMATION: synthetic oligonucleotide

<400> SEQUENCE: 4
aagacaaaat gctggaggga                                                20

<210> SEQ ID NO 5
<211> LENGTH: 20
<212> TYPE: DNA
<213> ORGANISM: Artificial
<220> FEATURE:
<223> OTHER INFORMATION: synthetic oligonucleotide

<400> SEQUENCE: 5
cactggcatt gtgatggact                                                20

<210> SEQ ID NO 6
<211> LENGTH: 20
<212> TYPE: DNA
<213> ORGANISM: Artificial
<220> FEATURE:
<223> OTHER INFORMATION: synthetic oligonucleotide

<400> SEQUENCE: 6
acggatgtca acgtcacact                                                20

<210> SEQ ID NO 7
<211> LENGTH: 21
<212> TYPE: DNA
<213> ORGANISM: Artificial
<220> FEATURE:
<223> OTHER INFORMATION: synthetic oligonucleotide

<400> SEQUENCE: 7
aactgcgagt gggtctggaa g                                              21

<210> SEQ ID NO 8
<211> LENGTH: 20
<212> TYPE: DNA
<213> ORGANISM: Artificial
<220> FEATURE:
<223> OTHER INFORMATION: synthetic oligonucleotide

<400> SEQUENCE: 8
tgggtctcgg gaaagcagtg                                                20

<210> SEQ ID NO 9
<211> LENGTH: 21
<212> TYPE: DNA
<213> ORGANISM: Artificial
<220> FEATURE:
<223> OTHER INFORMATION: synthetic oligonucleotide

<400> SEQUENCE: 9
```

```
ccgaatacca cgcacaccat c                                              21

<210> SEQ ID NO 10
<211> LENGTH: 21
<212> TYPE: DNA
<213> ORGANISM: Artificial
<220> FEATURE:
<223> OTHER INFORMATION: synthetic oligonucleotide

<400> SEQUENCE: 10
ctttccttgg ctctgcggtt c                                              21

<210> SEQ ID NO 11
<211> LENGTH: 21
<212> TYPE: DNA
<213> ORGANISM: Artificial
<220> FEATURE:
<223> OTHER INFORMATION: synthetic oligonucleotide

<400> SEQUENCE: 11
cgagcggtgt gggtaaaagt g                                              21

<210> SEQ ID NO 12
<211> LENGTH: 21
<212> TYPE: DNA
<213> ORGANISM: Artificial
<220> FEATURE:
<223> OTHER INFORMATION: synthetic oligonucleotide

<400> SEQUENCE: 12
ggtgtcgggt cttcttgctt g                                              21

<210> SEQ ID NO 13
<211> LENGTH: 21
<212> TYPE: DNA
<213> ORGANISM: Artificial
<220> FEATURE:
<223> OTHER INFORMATION: synthetic oligonucleotide

<400> SEQUENCE: 13
tgtgcgggga cattgcttct g                                              21

<210> SEQ ID NO 14
<211> LENGTH: 21
<212> TYPE: DNA
<213> ORGANISM: Artificial
<220> FEATURE:
<223> OTHER INFORMATION: synthetic oligonucleotide

<400> SEQUENCE: 14
tcccgatctg ccaagtcaca g                                              21

<210> SEQ ID NO 15
<211> LENGTH: 21
<212> TYPE: DNA
<213> ORGANISM: Artificial
<220> FEATURE:
<223> OTHER INFORMATION: synthetic oligonucleotide

<400> SEQUENCE: 15
cggggtgtgg tgagcatctt c                                              21

<210> SEQ ID NO 16
<211> LENGTH: 20
<212> TYPE: DNA
<213> ORGANISM: Artificial
<220> FEATURE:
```

-continued

<223> OTHER INFORMATION: synthetic oligonucleotide

<400> SEQUENCE: 16
ccttcttggt ccgcccgttc					20

<210> SEQ ID NO 17
<211> LENGTH: 21
<212> TYPE: DNA
<213> ORGANISM: Artificial
<220> FEATURE:
<223> OTHER INFORMATION: synthetic oligonucleotide

<400> SEQUENCE: 17
tcatcacgac ggcttggact g					21

<210> SEQ ID NO 18
<211> LENGTH: 21
<212> TYPE: DNA
<213> ORGANISM: Artificial
<220> FEATURE:
<223> OTHER INFORMATION: synthetic oligonucleotide

<400> SEQUENCE: 18
gccagagcac accaagaatc c					21

<210> SEQ ID NO 19
<211> LENGTH: 21
<212> TYPE: DNA
<213> ORGANISM: Artificial
<220> FEATURE:
<223> OTHER INFORMATION: synthetic oligonucleotide

<400> SEQUENCE: 19
atacacctgc acagcgtaca g					21

<210> SEQ ID NO 20
<211> LENGTH: 21
<212> TYPE: DNA
<213> ORGANISM: Artificial
<220> FEATURE:
<223> OTHER INFORMATION: synthetic oligonucleotide

<400> SEQUENCE: 20
tcccgcatct ctttcactca c					21

<210> SEQ ID NO 21
<211> LENGTH: 20
<212> TYPE: DNA
<213> ORGANISM: Artificial
<220> FEATURE:
<223> OTHER INFORMATION: synthetic oligonucleotide

<400> SEQUENCE: 21
gccctgagaa gaaagaagag					20

<210> SEQ ID NO 22
<211> LENGTH: 20
<212> TYPE: DNA
<213> ORGANISM: Artificial
<220> FEATURE:
<223> OTHER INFORMATION: synthetic oligonucleotide

<400> SEQUENCE: 22
ctgactgccc catactggaa					20

<210> SEQ ID NO 23

```
<211> LENGTH: 20
<212> TYPE: DNA
<213> ORGANISM: Artificial
<220> FEATURE:
<223> OTHER INFORMATION: synthetic oligonucleotide

<400> SEQUENCE: 23
agagaagcgc tggaacagag                                              20

<210> SEQ ID NO 24
<211> LENGTH: 20
<212> TYPE: DNA
<213> ORGANISM: Artificial
<220> FEATURE:
<223> OTHER INFORMATION: synthetic oligonucleotide

<400> SEQUENCE: 24
aggtgtctgc aaccgagagt                                              20

<210> SEQ ID NO 25
<211> LENGTH: 19
<212> TYPE: DNA
<213> ORGANISM: Artificial
<220> FEATURE:
<223> OTHER INFORMATION: synthetic oligonucleotide

<400> SEQUENCE: 25
gggatggcat actgtggac                                               19

<210> SEQ ID NO 26
<211> LENGTH: 19
<212> TYPE: DNA
<213> ORGANISM: Artificial
<220> FEATURE:
<223> OTHER INFORMATION: synthetic oligonucleotide

<400> SEQUENCE: 26
cttcctccac ccacttctc                                               19

<210> SEQ ID NO 27
<211> LENGTH: 20
<212> TYPE: DNA
<213> ORGANISM: Artificial
<220> FEATURE:
<223> OTHER INFORMATION: synthetic oligonucleotide

<400> SEQUENCE: 27
gagactggct ccatcagacc                                              20

<210> SEQ ID NO 28
<211> LENGTH: 20
<212> TYPE: DNA
<213> ORGANISM: Artificial
<220> FEATURE:
<223> OTHER INFORMATION: synthetic oligonucleotide

<400> SEQUENCE: 28
ctagccaggt tgcgaagaac                                              20

<210> SEQ ID NO 29
<211> LENGTH: 21
<212> TYPE: DNA
<213> ORGANISM: Artificial
<220> FEATURE:
<223> OTHER INFORMATION: synthetic oligonucleotide

<400> SEQUENCE: 29
```

```
ttcttgccag gttctggaag c                                              21

<210> SEQ ID NO 30
<211> LENGTH: 21
<212> TYPE: DNA
<213> ORGANISM: Artificial
<220> FEATURE:
<223> OTHER INFORMATION: synthetic oligonucleotide

<400> SEQUENCE: 30
tttcccacac tctgcacaca c                                              21

<210> SEQ ID NO 31
<211> LENGTH: 20
<212> TYPE: DNA
<213> ORGANISM: Artificial
<220> FEATURE:
<223> OTHER INFORMATION: synthetic oligonucleotide

<400> SEQUENCE: 31
ggcggcaacc agaagaacag                                                20

<210> SEQ ID NO 32
<211> LENGTH: 21
<212> TYPE: DNA
<213> ORGANISM: Artificial
<220> FEATURE:
<223> OTHER INFORMATION: synthetic oligonucleotide

<400> SEQUENCE: 32
gttgctccag ccgttcatgt g                                              21

<210> SEQ ID NO 33
<211> LENGTH: 21
<212> TYPE: DNA
<213> ORGANISM: Artificial
<220> FEATURE:
<223> OTHER INFORMATION: synthetic oligonucleotide

<400> SEQUENCE: 33
aggagaggtg gtggcgagta g                                              21

<210> SEQ ID NO 34
<211> LENGTH: 21
<212> TYPE: DNA
<213> ORGANISM: Artificial
<220> FEATURE:
<223> OTHER INFORMATION: synthetic oligonucleotide

<400> SEQUENCE: 34
gttgggatgg tcctgcatgt g                                              21

<210> SEQ ID NO 35
<211> LENGTH: 21
<212> TYPE: DNA
<213> ORGANISM: Artificial
<220> FEATURE:
<223> OTHER INFORMATION: synthetic oligonucleotide

<400> SEQUENCE: 35
tcctacaacc agaaacacta g                                              21

<210> SEQ ID NO 36
<211> LENGTH: 20
<212> TYPE: DNA
<213> ORGANISM: Artificial
<220> FEATURE:
```

<223> OTHER INFORMATION: synthetic oligonucleotide

<400> SEQUENCE: 36
gtgcagagac atctgaatgg                                               20

<210> SEQ ID NO 37
<211> LENGTH: 24
<212> TYPE: DNA
<213> ORGANISM: Artificial
<220> FEATURE:
<223> OTHER INFORMATION: synthetic oligonucleotide

<400> SEQUENCE: 37
atgaagtgca agcggtggca gaaa                                          24

<210> SEQ ID NO 38
<211> LENGTH: 24
<212> TYPE: DNA
<213> ORGANISM: Artificial
<220> FEATURE:
<223> OTHER INFORMATION: synthetic oligonucleotide

<400> SEQUENCE: 38
cctggtggag tcacagagta gttc                                          24

<210> SEQ ID NO 39
<211> LENGTH: 20
<212> TYPE: DNA
<213> ORGANISM: Artificial
<220> FEATURE:
<223> OTHER INFORMATION: synthetic oligonucleotide

<400> SEQUENCE: 39
ggcacccagc acaatgaaga                                               20

<210> SEQ ID NO 40
<211> LENGTH: 21
<212> TYPE: DNA
<213> ORGANISM: Artificial
<220> FEATURE:
<223> OTHER INFORMATION: synthetic oligonucleotide

<400> SEQUENCE: 40
cgactgctgt caccttcacc g                                             21

<210> SEQ ID NO 41
<211> LENGTH: 21
<212> TYPE: DNA
<213> ORGANISM: Artificial
<220> FEATURE:
<223> OTHER INFORMATION: synthetic oligonucleotide

<400> SEQUENCE: 41
agtgagaggc aacctggaga g                                             21

<210> SEQ ID NO 42
<211> LENGTH: 21
<212> TYPE: DNA
<213> ORGANISM: Artificial
<220> FEATURE:
<223> OTHER INFORMATION: synthetic oligonucleotide

<400> SEQUENCE: 42
gacagacacc gagggaaaga c                                             21

<210> SEQ ID NO 43

```
<211> LENGTH: 20
<212> TYPE: DNA
<213> ORGANISM: Artificial
<220> FEATURE:
<223> OTHER INFORMATION: synthetic oligonucleotide

<400> SEQUENCE: 43
catccacagc aaatgacagc                                              20

<210> SEQ ID NO 44
<211> LENGTH: 20
<212> TYPE: DNA
<213> ORGANISM: Artificial
<220> FEATURE:
<223> OTHER INFORMATION: synthetic oligonucleotide

<400> SEQUENCE: 44
tttctgcaaa gctcctaccg                                              20

<210> SEQ ID NO 45
<211> LENGTH: 23
<212> TYPE: DNA
<213> ORGANISM: Artificial
<220> FEATURE:
<223> OTHER INFORMATION: synthetic oligonucleotide

<400> SEQUENCE: 45
agccccagag tgaaaccact gtc                                          23

<210> SEQ ID NO 46
<211> LENGTH: 21
<212> TYPE: DNA
<213> ORGANISM: Artificial
<220> FEATURE:
<223> OTHER INFORMATION: synthetic oligonucleotide

<400> SEQUENCE: 46
gtgttctcac agacccagct g                                            21

<210> SEQ ID NO 47
<211> LENGTH: 20
<212> TYPE: DNA
<213> ORGANISM: Artificial
<220> FEATURE:
<223> OTHER INFORMATION: synthetic oligonucleotide

<400> SEQUENCE: 47
ggcacccagc acaatgaaga                                              20

<210> SEQ ID NO 48
<211> LENGTH: 21
<212> TYPE: DNA
<213> ORGANISM: Artificial
<220> FEATURE:
<223> OTHER INFORMATION: synthetic oligonucleotide

<400> SEQUENCE: 48
cgactgctgt caccttcacc g                                            21

<210> SEQ ID NO 49
<211> LENGTH: 21
<212> TYPE: DNA
<213> ORGANISM: Artificial
<220> FEATURE:
<223> OTHER INFORMATION: synthetic oligonucleotide

<400> SEQUENCE: 49
```
agtgagaggc aacctggaga g                                              21

<210> SEQ ID NO 50
<211> LENGTH: 21
<212> TYPE: DNA
<213> ORGANISM: Artificial
<220> FEATURE:
<223> OTHER INFORMATION: synthetic oligonucleotide

<400> SEQUENCE: 50
gacagacacc gagggaaaga c                                              21

<210> SEQ ID NO 51
<211> LENGTH: 19
<212> TYPE: DNA
<213> ORGANISM: Artificial
<220> FEATURE:
<223> OTHER INFORMATION: synthetic oligonucleotide

<400> SEQUENCE: 51
gcagaatgtg ggaaagcct                                                 19

<210> SEQ ID NO 52
<211> LENGTH: 19
<212> TYPE: DNA
<213> ORGANISM: Artificial
<220> FEATURE:
<223> OTHER INFORMATION: synthetic oligonucleotide

<400> SEQUENCE: 52
gactgaataa acttcttgc                                                 19

<210> SEQ ID NO 53
<211> LENGTH: 22
<212> TYPE: DNA
<213> ORGANISM: Artificial
<220> FEATURE:
<223> OTHER INFORMATION: synthetic oligonucleotide

<400> SEQUENCE: 53
gagtcaatac gtgaccgtgg ac                                             22

<210> SEQ ID NO 54
<211> LENGTH: 22
<212> TYPE: DNA
<213> ORGANISM: Artificial
<220> FEATURE:
<223> OTHER INFORMATION: synthetic oligonucleotide

<400> SEQUENCE: 54
ctgaagtagc cgcgatagac ag                                             22

<210> SEQ ID NO 55
<211> LENGTH: 20
<212> TYPE: DNA
<213> ORGANISM: Artificial
<220> FEATURE:
<223> OTHER INFORMATION: synthetic oligonucleotide

<400> SEQUENCE: 55
catccacagc aaatgacagc                                                20

<210> SEQ ID NO 56
<211> LENGTH: 20
<212> TYPE: DNA
<213> ORGANISM: Artificial
<220> FEATURE:

```
<223> OTHER INFORMATION: synthetic oligonucleotide

<400> SEQUENCE: 56
tttctgcaaa gctcctaccg                                                    20

<210> SEQ ID NO 57
<211> LENGTH: 22
<212> TYPE: DNA
<213> ORGANISM: Artificial
<220> FEATURE:
<223> OTHER INFORMATION: synthetic oligonucleotide

<400> SEQUENCE: 57
tgtgctcaat gacagatttc ag                                                 22

<210> SEQ ID NO 58
<211> LENGTH: 20
<212> TYPE: DNA
<213> ORGANISM: Artificial
<220> FEATURE:
<223> OTHER INFORMATION: synthetic oligonucleotide

<400> SEQUENCE: 58
tagaagcctg ggtattctgc                                                    20

<210> SEQ ID NO 59
<211> LENGTH: 20
<212> TYPE: DNA
<213> ORGANISM: Artificial
<220> FEATURE:
<223> OTHER INFORMATION: synthetic oligonucleotide

<400> SEQUENCE: 59
ggacccagga aaccaaagtc                                                    20

<210> SEQ ID NO 60
<211> LENGTH: 21
<212> TYPE: DNA
<213> ORGANISM: Artificial
<220> FEATURE:
<223> OTHER INFORMATION: synthetic oligonucleotide

<400> SEQUENCE: 60
gaatgaggga gtgagcaaac c                                                  21
```